US011987640B2

(12) United States Patent
Correnti et al.

(10) Patent No.: US 11,987,640 B2
(45) Date of Patent: May 21, 2024

(54) ANTI-MESOTHELIN ANTIGEN-BINDING MOLECULES AND USES THEREOF

(71) Applicant: Fred Hutchinson Cancer Center, Seattle, WA (US)

(72) Inventors: Colin Correnti, Seattle, WA (US); Ashok Bandaranayake, Lake Stevens, WA (US); Christopher Mehlin, Seattle, WA (US); James M. Olson, Seattle, WA (US); Soheil Meshinchi, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 77 days.

(21) Appl. No.: 17/223,871

(22) Filed: Apr. 6, 2021

(65) Prior Publication Data
US 2021/0309755 A1  Oct. 7, 2021

Related U.S. Application Data

(60) Provisional application No. 63/006,308, filed on Apr. 7, 2020.

(51) Int. Cl.
*C07K 16/30* (2006.01)
*C07K 16/28* (2006.01)
*G01N 33/574* (2006.01)
*A61K 39/00* (2006.01)

(52) U.S. Cl.
CPC .......... *C07K 16/30* (2013.01); *C07K 16/2809* (2013.01); *G01N 33/57488* (2013.01); *A61K 2039/505* (2013.01); *C07K 2317/24* (2013.01); *C07K 2317/31* (2013.01); *C07K 2317/33* (2013.01); *C07K 2317/56* (2013.01); *C07K 2317/565* (2013.01); *C07K 2317/622* (2013.01); *C07K 2317/73* (2013.01); *C07K 2317/74* (2013.01)

(58) Field of Classification Search
CPC .......... C07K 2317/565; C07K 2317/56; C07K 2317/31; A61K 2039/505
USPC .......................................... 424/133.1, 136.1
See application file for complete search history.

(56) References Cited

U.S. PATENT DOCUMENTS 9,334,331 B2 * 5/2016 Igawa ..................... C07K 16/40
10,421,807 B2 * 9/2019 Gonzales ................ A61P 11/00
11,149,094 B2 * 10/2021 Chiu .................... C07K 16/241
2008/0261245 A1  10/2008 Pastan

FOREIGN PATENT DOCUMENTS

WO       2017/020858 A1    2/2017
WO       WO 2020092631    * 10/2019

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Chowdhury et al (J Immunol Methods Mar. 1, 2001;249(1-2):147-54).*
Hatter et al (MABS 2020, vol. 12, No. 1, e1739408 (13 pages)).*
Patent Cooperation Treaty: International Search Report and Written Opinion for PCT/US2021/026013 dated Oct. 1, 2021; 13 pages.

* cited by examiner

*Primary Examiner* — Lynn A Bristol
(74) *Attorney, Agent, or Firm* — Schwabe, Williamson & Wyatt P.C.

(57) ABSTRACT

Mesothelin (MSLN) is expressed on pancreatic cancers, ovarian cancers and mesotheliomas. The present disclosure provides antigen-binding molecules, including anti-MSLN antibodies, and bispecific antigen-binding molecules that bind to both MSLN and a T cell antigen (e.g., CD3) and activate T cells in the presence of MSLN-expressing tumor cells. The antigen-binding molecules of this disclosure are useful for the treatment of diseases and disorders in which a MSLN-targeted immune response is desired and/or therapeutically beneficial. For example, the antigen-binding molecules of the present disclosure are useful for the treatment of various cancers, including pancreatic cancer, ovarian cancer and mesotheliomas.

12 Claims, 55 Drawing Sheets

Specification includes a Sequence Listing.

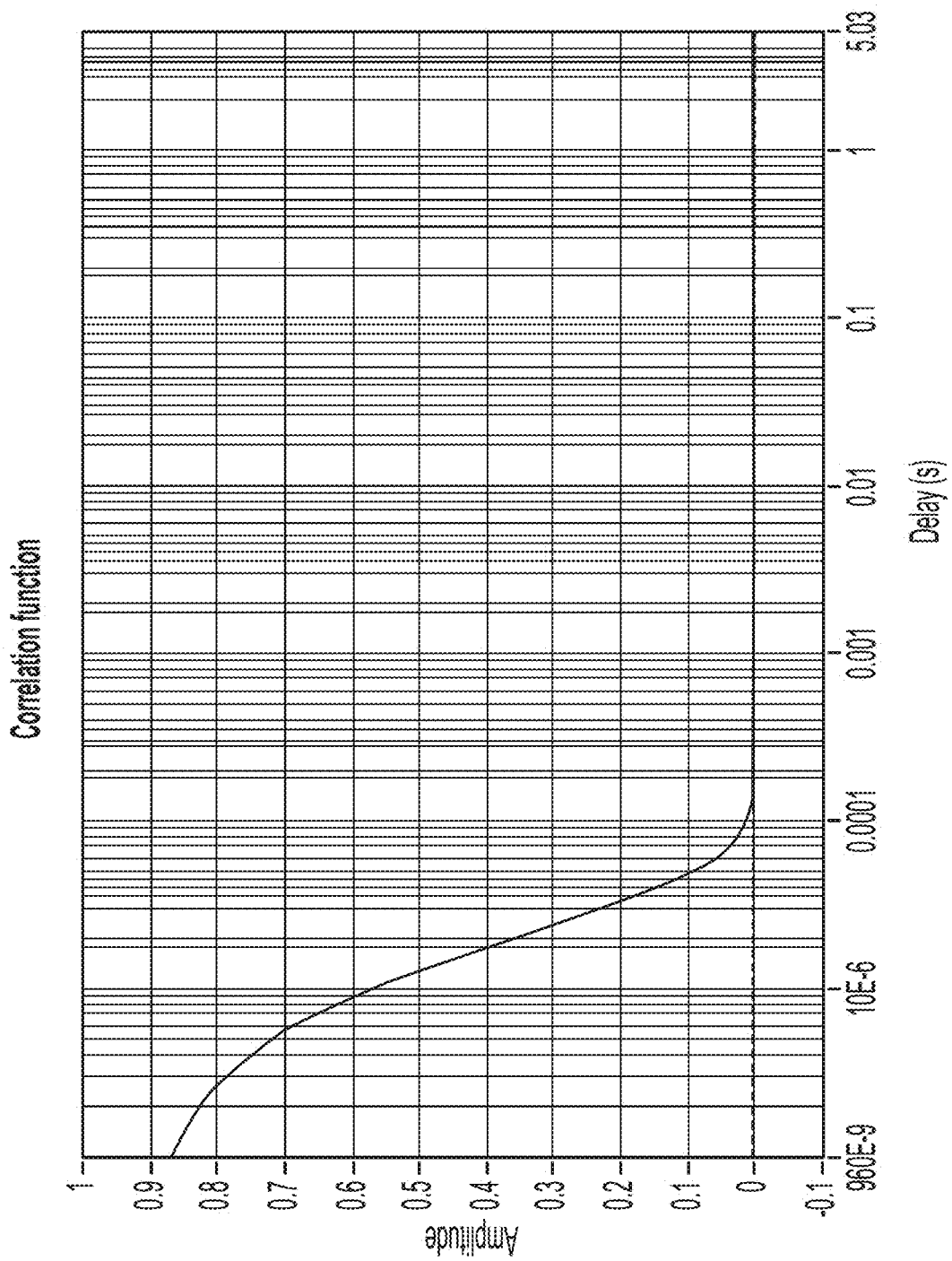
FIG. 2B-Cont.

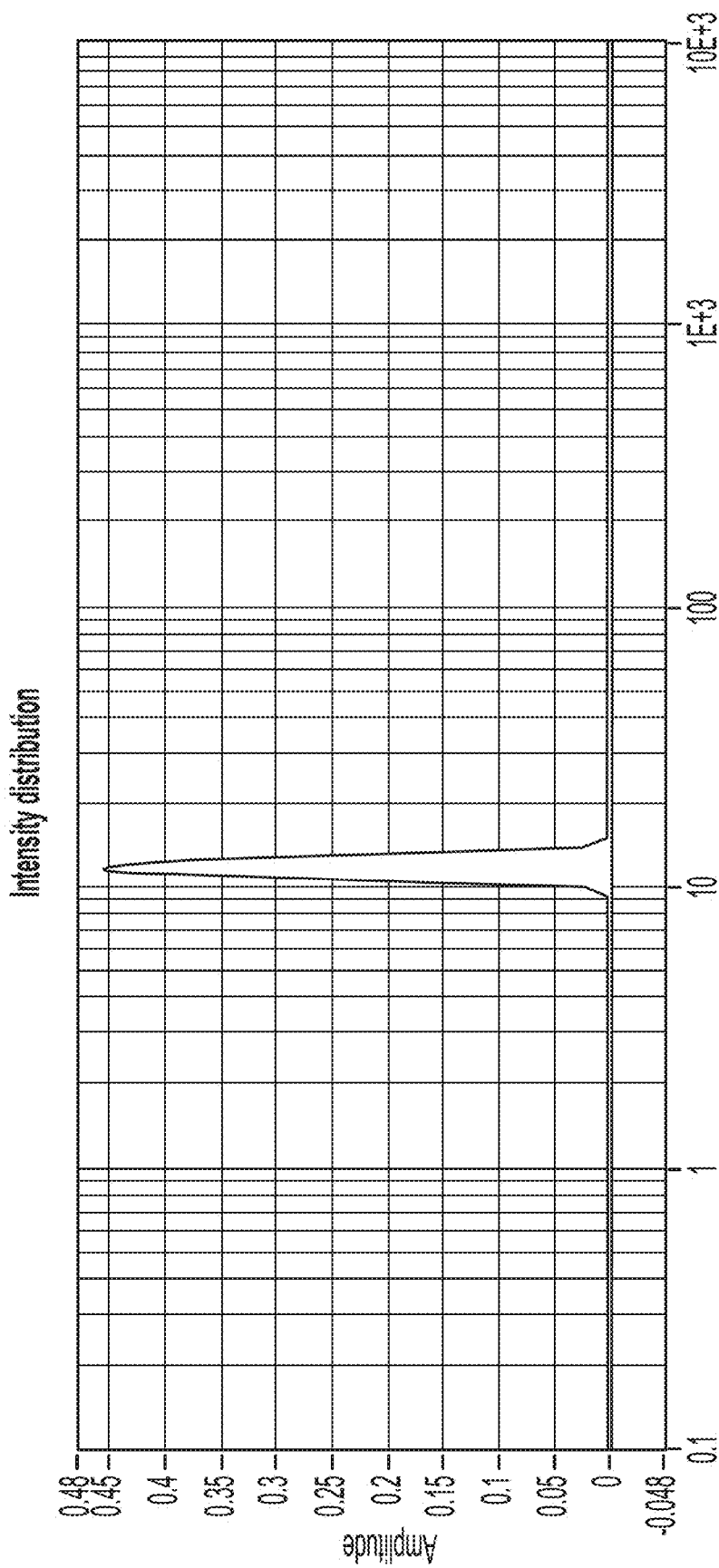
FIG. 2B-Cont.

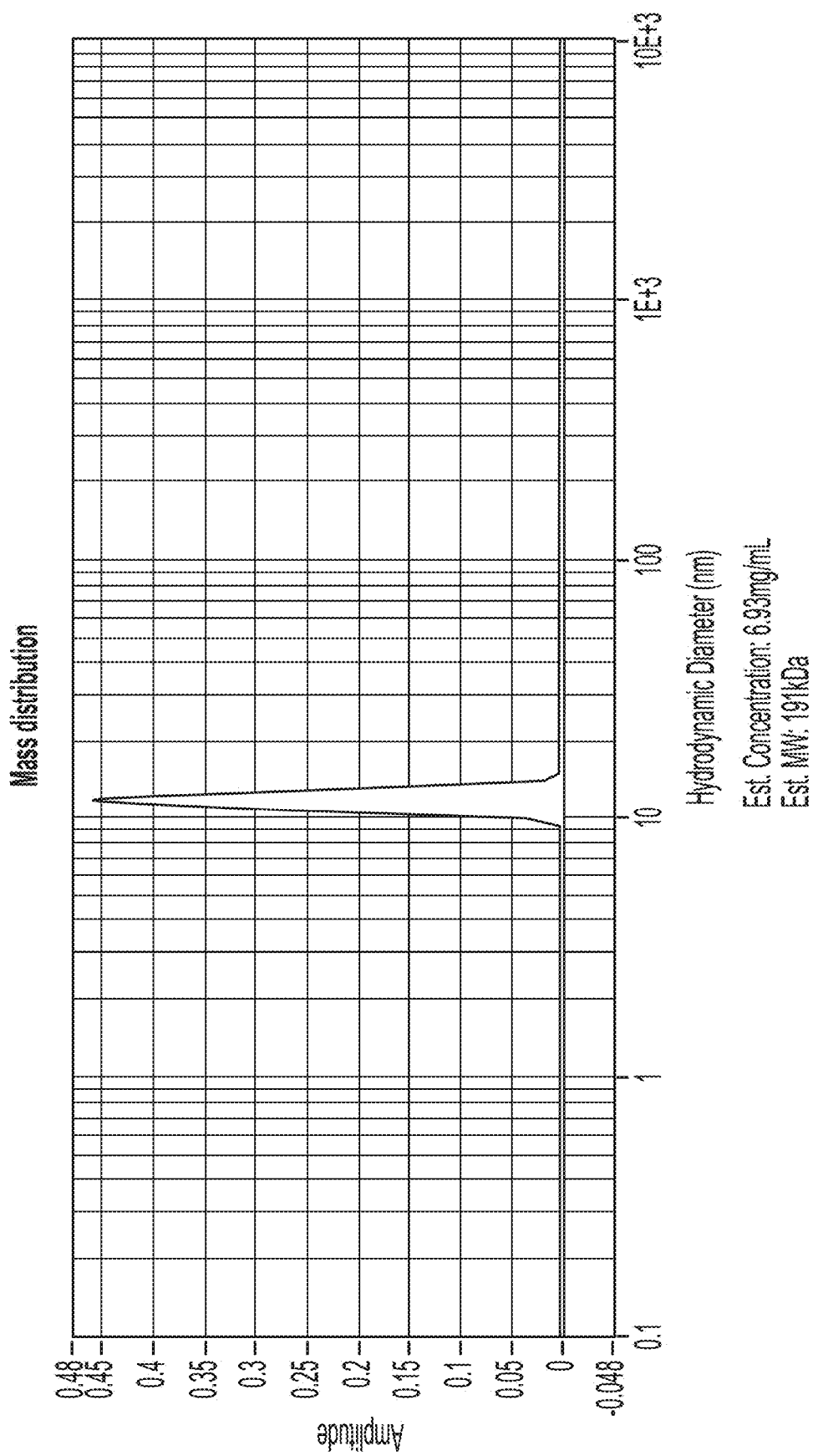
FIG. 2B-Cont.

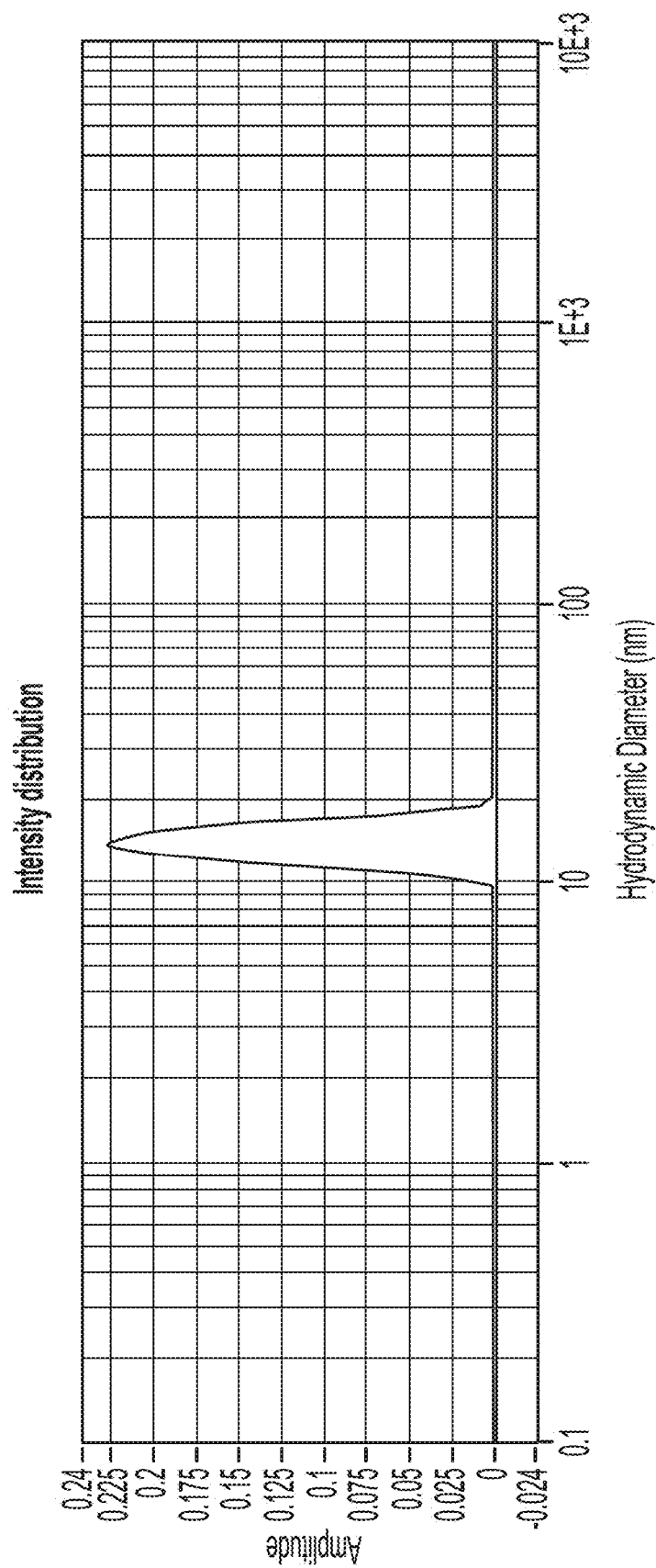
FIG. 4D-Cont.

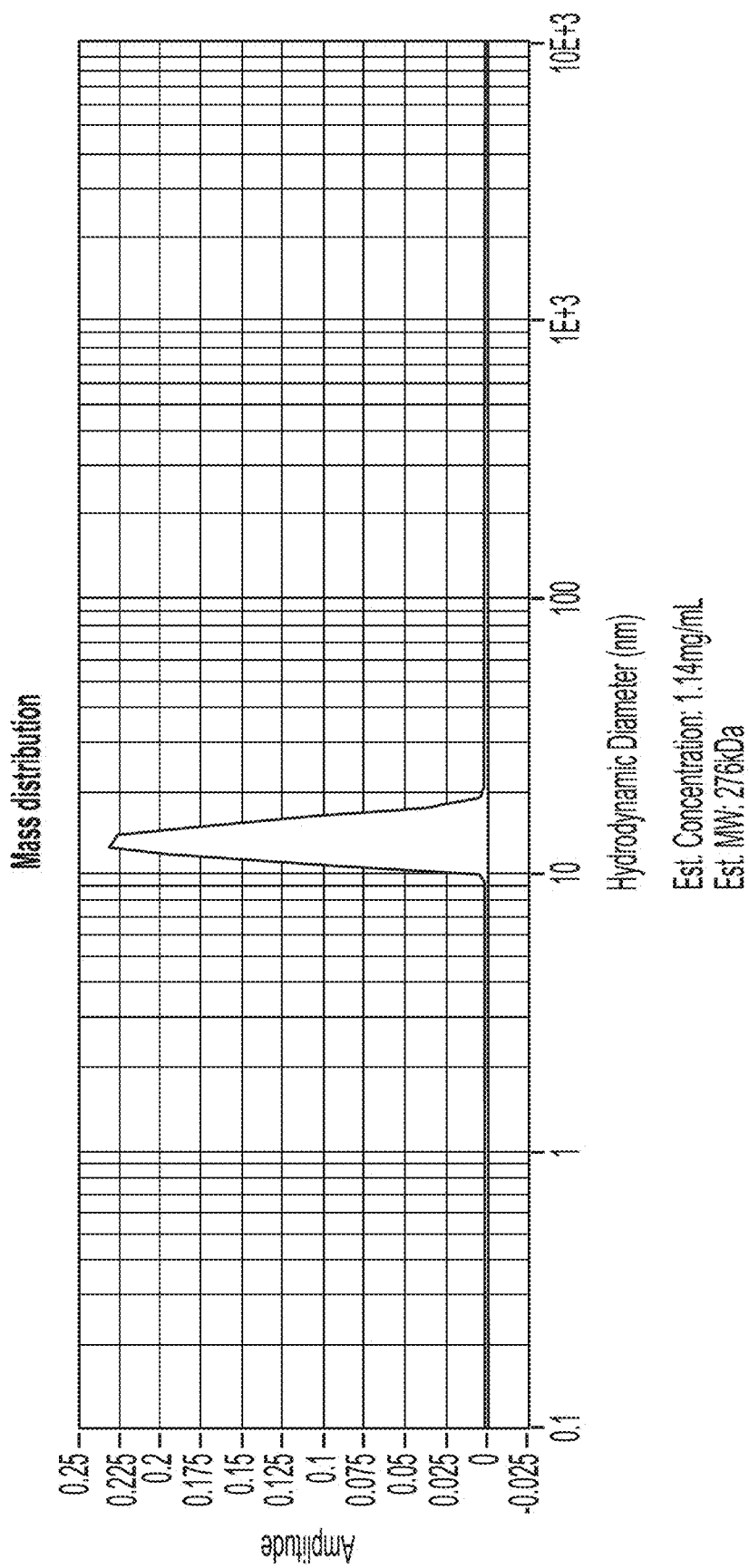
FIG. 4D-Cont.

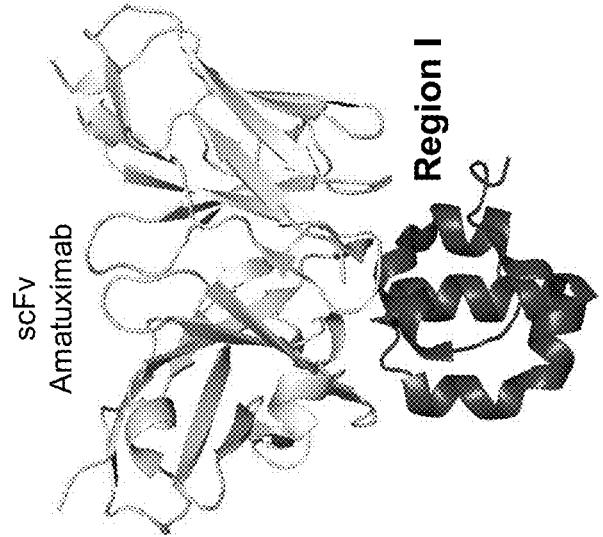
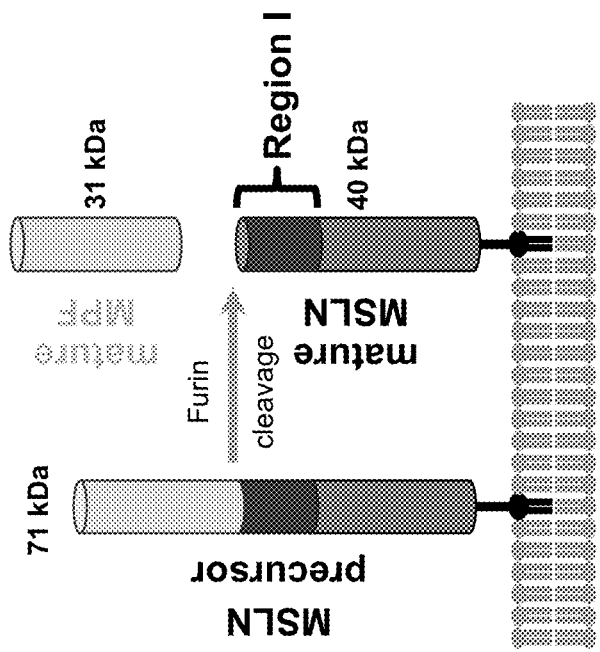
FIG. 5B
FIG. 5A

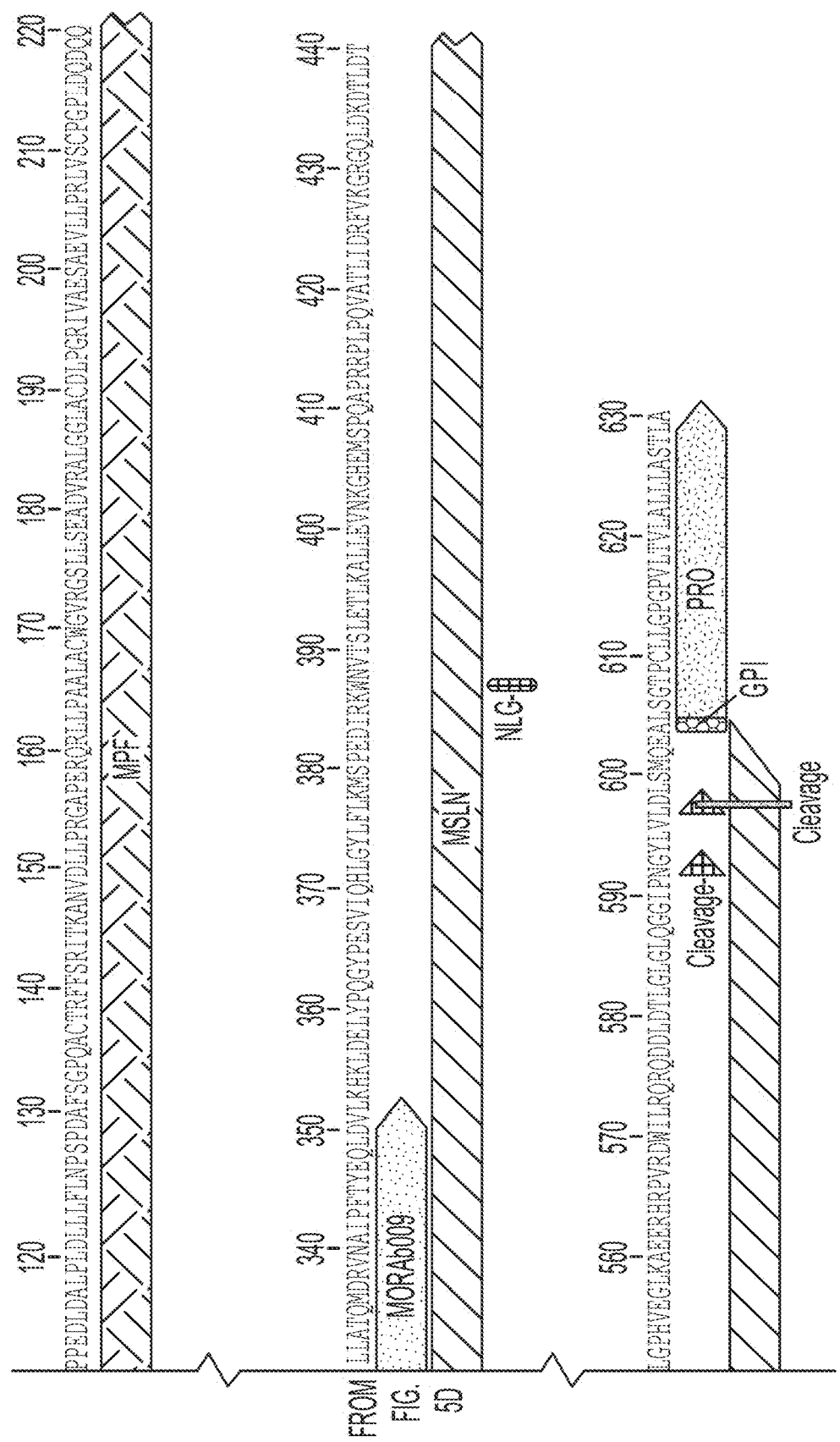
FIG. 5D-Cont.

| CELL LINE | MSLN SURFACE EXPRESSION (MFI) | MSLN TRANSCRIPT EXPRESSION (MSLN/1000 GUSB COPIES) |
|---|---|---|
| MV4;11 | 30.3 | 18.4 |
| MV4;11 (MSLN+) | 31727 | 2519 |
| K562 | 58.7 | 10.4 |
| K562 (MSLN+) | 7701 | 75858 |
| Kasumi-1 | 29.4 | 0.5 |
| Kasumi-1 (MSLN+) | 5892 | 15552 |
| Me-1 | 20 | 1.9 |
| Me-1 (MSLN+) | 781 | 5800 |
| NOMO-1 | 694 | 4117 |
| NOMO-1 (MSLN^KO) | 26.8 | 167* |
| NTPL-146 | 403.8 | 16786 |
| DF-2 | 28.8 | 3.3 |
| *NOMO-1 knock-out engineered using CRISPR. | | |

FIG. 9B

High avidity for cell surface MSLN

Low affinity for soluble MSLN-related proteins

SEQUENCE LISTING

<160> NUMBER OF SEQ ID NOS: 83

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Arg Ser Tyr
            20                  25                  30

Ala Met Thr Trp Val Arg Gln Ala Pro Gly Lys Gly Leu Glu Trp Val
        35                  40                  45

Ser Gly Ile Ser Val Ser Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Ala Ala Val Gly Ser Phe Asp Tyr Trp Gly Gln Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Gly Ser Trp
            20                  25                  30

Leu Ala Trp Tyr Gln Gln Lys Pro Glu Lys Ala Pro Gln Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Leu Thr Phe Arg Ser Tyr Ala Met Thr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ile Ser Val Ser Gly Gly Ile Thr Tyr Tyr Ala Asp Ser Val Lys
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Ala Ala Val Gly Ser Phe Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Ser Gln Gly Ile Gly Ser Trp Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Ser Ser Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Asn Ser Tyr Pro Leu Thr
1               5

<210> SEQ ID NO 9
<211> LENGTH: 119

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Arg Asn Tyr
            20                  25                  30

Ala Met Thr Trp Val Arg Gln Ala Pro Gly Lys Gly Leu Glu Trp Val
        35                  40                  45

Ser Gly Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Val Lys Arg Gly Ala Ala Val Gly Ser Phe Asp Tyr Trp Gly Gln Gly
            100                 105                 110

Thr Leu Val Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Gly Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Ile Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Leu Thr Phe Arg Asn Tyr Ala Met Thr
1               5                   10
```

```
<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ile Ser Val Ser Gly Gly Ser Thr Tyr Tyr Ala Asp Ser Val Lys
1               5                   10                  15

Gly

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Gly Ala Ala Val Gly Ser Phe Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Ser Gln Gly Ile Gly Ser Trp Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Tyr Asn Ser Tyr Pro Leu Thr
1               5

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 17

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Arg Ser Tyr
            20                  25                  30

Ala Met Thr Trp Val Arg Gln Ala Pro Gly Lys Gly Leu Glu Trp Val
        35                  40                  45

Ser Ala Ile Ser Val Ser Gly Gly Asn Thr Tyr Phe Ala Asp Pro Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Ala Ile Gly Ser Phe Asp Tyr Trp Gly Gln Gly
            100                 105                 110

Thr Leu Val Thr Val Ser Ser
            115

<210> SEQ ID NO 18
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Trp
            20                  25                  30

Leu Ala Trp Tyr Gln Leu Lys Ser Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln
            115                 120

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Arg Ser Tyr Ala Met Thr
1               5                   10

<210> SEQ ID NO 20
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ile Ser Val Ser Gly Gly Asn Thr Tyr Phe Ala Asp Pro Val Lys
1               5                   10                  15

Gly

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Thr Ala Ile Gly Ser Phe Asp Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Gln Gly Ile Gly Ser Trp Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ser Ser Leu Gln Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Tyr Asn Ser Tyr Pro Leu Thr
1               5

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25
```

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Val Ser Gly Gly Asn Thr Tyr Phe Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Ala Ala Ile Gly Ser Phe Asp Tyr Trp Gly Gln Gly
            100                 105                 110

Thr Leu Val Thr Val Ser Ser
            115

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Phe Thr Phe Ser Ser Tyr Ala Met Thr
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Ser Val Ser Gly Gly Asn Thr Tyr Phe Ala Asp Pro Val Lys Gly
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Gly Ala Ala Ile Gly Ser Phe Asp Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Gln Gly Ile Gly Ser Trp Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Ser Ser Leu Gln Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Tyr Asn Ser Tyr Pro Leu Thr
1               5

<210> SEQ ID NO 33
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

```
Tyr Trp Ser Trp Ile Arg Gln Pro Pro Gly Lys Gly Leu Glu Trp Ile
            35                  40                  45

Gly Tyr Ile Tyr Tyr Ser Gly Asn Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Asn Leu Thr Ser Val Thr Ala Val Asp Thr Ala Val Tyr Tyr Cys Ala
                 85                  90                  95

Arg Gly Ser Gly Trp Tyr Phe Asp Tyr Trp Gly Gln Gly Thr Leu Val
            100                 105                 110

Thr Val Ser Ser
        115

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gly His Ser Ser Tyr Ala
            20                  25                  30

Ile Ala Trp His Gln Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gln Thr Trp Gly
                 85                  90                  95

Thr Gly Ile Leu Val Phe Gly Gly Gly Thr Lys Leu Thr Val Leu Gly
            100                 105                 110

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Ser Ile Ser Ser Tyr Tyr Trp Ser
 1               5                  10

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ile Tyr Tyr Ser Gly Asn Thr Asn Tyr Asn Pro Ser Leu Lys Ser
 1               5                  10                  15
```

```
<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Gly Trp Tyr Phe Asp Tyr
1               5

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Leu Ser Ser Gly His Ser Ser Tyr Ala Ile Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Asn Ser Asp Gly Ser His
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Thr Trp Gly Thr Gly Ile Leu Val
1               5

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Asp Ser Gly Gly Gly Val Val Gln Pro Gly Arg
1               5                   10                  15

Ser Leu Arg Leu Ser Cys Ala Ala Ser Gly Phe Thr Phe Ser Arg Asn
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95
Ala Arg Asp Thr Ala Ala Gly Tyr Tyr Tyr Tyr Gly Met Asp Val
                100                 105                 110
Trp Gly Gln Gly Thr Thr Val Thr Val Ser
        115                 120
```

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Ile Gln Leu Thr Gln Ser Pro Ser Phe Leu Ser Ala Ser Val Gly
1               5                   10                  15
Asp Arg Val Thr Ile Thr Cys Arg Ala Ser Gln Gly Ile Ser Ser Phe
            20                  25                  30
Leu Ala Trp Tyr Gln Gln Lys Pro Gly Lys Ala Pro Lys Val Leu Ile
        35                  40                  45
Tyr Val Ser Ser Thr Phe Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Leu Asn Ile Phe Pro Leu
                85                  90                  95
Thr Phe Gly Gly Gly Thr Lys Val Glu Ser Lys
                100                 105
```

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gly Phe Thr Phe Ser Arg Asn Gly Met His
1               5                   10
```

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Val Ile Ser Tyr Asp Gly Ser Asn Lys Tyr Tyr Ala Asp Ser Val Lys
1               5                   10                  15
Gly
```

<210> SEQ ID NO 45
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 45

Asp Thr Ala Ala Gly Tyr Tyr Tyr Tyr Gly Met Asp Val
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Ser Gln Gly Ile Ser Ser Phe Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Thr Phe Gln Ser Gly Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Leu Asn Ile Phe Pro Leu Thr
1               5

<210> SEQ ID NO 49
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Leu Pro Thr Ala Arg Pro Leu Leu Gly Ser Cys Gly Ser Pro
1               5                   10                  15

Ile Cys Ser Arg Ser Phe Leu Leu Leu Leu Ser Leu Gly Trp Ile
            20                  25                  30

Pro Arg Leu Gln Thr Gln Thr Thr Lys Thr Ser Gln Glu Ala Thr Leu
        35                  40                  45

Leu His Ala Val Asn Gly Ala Ala Asp Phe Ala Ser Leu Pro Thr Gly
    50                  55                  60

Leu Phe Leu Gly Leu Thr Cys Glu Glu Val Ser Asp Leu Ser Met Glu
65                  70                  75                  80

Gln Ala Lys Gly Leu Ala Met Ala Val Arg Gln Lys Asn Ile Thr Leu
                85                  90                  95

```
Arg Gly His Gln Leu Arg Cys Leu Ala Arg Arg Leu Pro Arg His Leu
            100                 105                 110

Thr Asp Glu Glu Leu Asn Ala Leu Pro Leu Asp Leu Leu Leu Phe Leu
        115                 120                 125

Asn Pro Ala Met Phe Pro Gly Gln Gln Ala Cys Ala His Phe Phe Ser
    130                 135                 140

Leu Ile Ser Lys Ala Asn Val Asp Val Leu Pro Arg Arg Ser Leu Glu
145                 150                 155                 160

Arg Gln Arg Leu Leu Met Glu Ala Leu Lys Cys Gln Gly Val Tyr Gly
                165                 170                 175

Phe Gln Val Ser Glu Ala Asp Val Arg Ala Leu Gly Gly Leu Ala Cys
            180                 185                 190

Asp Leu Pro Gly Lys Phe Val Ala Arg Ser Ser Glu Val Leu Leu Pro
        195                 200                 205

Trp Leu Ala Gly Cys Gln Gly Pro Leu Asp Gln Ser Gln Glu Lys Ala
    210                 215                 220

Val Arg Glu Val Leu Arg Ser Gly Arg Thr Gln Tyr Gly Pro Pro Ser
225                 230                 235                 240

Lys Trp Ser Val Ser Thr Leu Asp Ala Leu Gln Ser Leu Val Ala Val
                245                 250                 255

Leu Asp Glu Ser Ile Val Gln Ser Ile Pro Lys Asp Val Lys Ala Glu
            260                 265                 270

Trp Leu Gln His Ile Ser Arg Asp Pro Ser Arg Leu Gly Ser Lys Leu
        275                 280                 285

Thr Val Ile His Pro Arg Phe Arg Arg Asp Ala Glu Gln Lys Ala Cys
    290                 295                 300

Pro Pro Gly Lys Glu Pro Tyr Lys Val Asp Glu Asp Leu Ile Phe Tyr
305                 310                 315                 320

Gln Asn Trp Glu Leu Glu Ala Cys Val Asp Gly Thr Met Leu Ala Arg
                325                 330                 335

Gln Met Asp Leu Val Asn Glu Ile Pro Phe Thr Tyr Glu Gln Leu Ser
            340                 345                 350

Ile Phe Lys His Lys Leu Asp Lys Thr Tyr Pro Gln Gly Tyr Pro Glu
        355                 360                 365

Ser Leu Ile Gln Gln Leu Gly His Phe Phe Arg Tyr Val Ser Pro Glu
    370                 375                 380

Asp Ile His Gln Trp Asn Val Thr Ser Pro Asp Thr Val Lys Thr Leu
385                 390                 395                 400

Leu Lys Val Ser Lys Gly Gln Lys Met Asn Ala Gln Ala Ile Ala Leu
                405                 410                 415

Val Ala Cys Tyr Leu Arg Gly Gly Gln Leu Asp Glu Asp Met Val
            420                 425                 430

Lys Ala Leu Gly Asp Ile Pro Leu Ser Tyr Leu Cys Asp Phe Ser Pro
        435                 440                 445

Gln Asp Leu His Ser Val Pro Ser Ser Val Met Trp Leu Val Gly Pro
    450                 455                 460

Gln Asp Leu Asp Thr Cys Asp Pro Arg Gln Leu Asp Val Leu Tyr Pro
465                 470                 475                 480

Lys Ala Arg Leu Ala Phe Gln Asn Met Asn Gly Ser Glu Tyr Phe Val
                485                 490                 495

Lys Ile Gln Ser Phe Leu Gly Gly Ala Pro Thr Glu Asp Leu Lys Ala
            500                 505                 510

Leu Ser Gln Gln Asn Val Ser Met Asp Leu Ala Thr Phe Met Lys Leu
```

```
                515                 520                 525

Arg Thr Asp Ala Val Leu Pro Leu Thr Val Ala Glu Val Gln Lys Leu
530                 535                 540

Leu Gly Pro His Val Glu Gly Leu Lys Ala Glu Glu Arg His Arg Pro
545                 550                 555                 560

Val Arg Asp Trp Ile Leu Arg Gln Arg Gln Asp Asp Leu Asp Thr Leu
                565                 570                 575

Gly Leu Gly Leu Gln Gly Gly Ile Pro Asn Gly Tyr Leu Val Leu Asp
            580                 585                 590

Leu Ser Met Gln Glu Ala Leu Ser Gly Thr Pro Cys Leu Leu Gly Pro
        595                 600                 605

Gly Pro Val Leu Thr Val Leu Ala Leu Leu Leu Ala Ser Thr Leu Ala
    610                 615                 620

<210> SEQ ID NO 50
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Pro Gln Asp Leu Asp Thr Cys Asp Pro Arg Gln Leu Asp Val Leu Tyr
1               5                   10                  15

Pro Lys Ala Arg Leu Ala Phe Gln Asn Met Asn Gly Ser Glu Tyr Phe
            20                  25                  30

Val Lys Ile Gln Ser Phe Leu Gly Gly Ala Pro Thr Glu Asp Leu Lys
        35                  40                  45

Ala Leu Ser Gln Gln Asn Val Ser Met Asp Leu Ala Thr Phe Met Lys
    50                  55                  60

Leu Arg Thr Asp Ala Val Leu Pro Leu Thr Val Ala Glu Val Gln Lys
65                  70                  75                  80

Leu Leu Gly Pro His Val Glu Gly Leu Lys Ala Glu Glu Arg His Arg
                85                  90                  95

Pro Val Arg Asp Trp Ile Leu Arg Gln Arg Gln Asp Asp Leu Asp Thr
            100                 105                 110

Leu Gly Leu Gly Leu Gln Gly Gly Ile Pro Asn Gly Tyr Leu Val Leu
        115                 120                 125

Asp Leu Ser Met Gln Glu Ala Leu
    130                 135

<210> SEQ ID NO 51
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Q or E
<220> FEATURE:
<221> NAME/KEY: MOD_RES
<222> LOCATION: (5)..(5)
<223> OTHER INFORMATION: V or L
<220> FEATURE:
<221> NAME/KEY: MOD_RES
<222> LOCATION: (6)..(6)
<223> OTHER INFORMATION: D or E
<220> FEATURE:
```

```
<221> NAME/KEY: MOD_RES
<222> LOCATION: (10)..(10)
<223> OTHER INFORMATION: G or D
<220> FEATURE:
<221> NAME/KEY: MOD_RES
<222> LOCATION: (11)..(11)
<223> OTHER INFORMATION: V or L
<220> FEATURE:
<221> NAME/KEY: MOD_RES
<222> LOCATION: (16)..(16)
<223> OTHER INFORMATION: R, G, or E
<220> FEATURE:
<221> NAME/KEY: MOD_RES
<222> LOCATION: (27)..(27)
<223> OTHER INFORMATION: F or L
<220> FEATURE:
<221> NAME/KEY: MOD_RES
<222> LOCATION: (30)..(30)
<223> OTHER INFORMATION: S or R
<220> FEATURE:
<221> NAME/KEY: MOD_RES
<222> LOCATION: (31)..(31)
<223> OTHER INFORMATION: R, S, or N
<220> FEATURE:
<221> NAME/KEY: MOD_RES
<222> LOCATION: (32)..(32)
<223> OTHER INFORMATION: N or Y
<220> FEATURE:
<221> NAME/KEY: MOD_RES
<222> LOCATION: (33)..(33)
<223> OTHER INFORMATION: G or A
<220> FEATURE:
<221> NAME/KEY: MOD_RES
<222> LOCATION: (35)..(35)
<223> OTHER INFORMATION: H or T
<220> FEATURE:
<221> NAME/KEY: MOD_RES
<222> LOCATION: (49)..(49)
<223> OTHER INFORMATION: A or S
<220> FEATURE:
<221> NAME/KEY: MOD_RES
<222> LOCATION: (50)..(50)
<223> OTHER INFORMATION: V, G, or A
<220> FEATURE:
<221> NAME/KEY: MOD_RES
<222> LOCATION: (53)..(53)
<223> OTHER INFORMATION: Y or V
<220> FEATURE:
<221> NAME/KEY: MOD_RES
<222> LOCATION: (54)..(54)
<223> OTHER INFORMATION: D or S
<220> FEATURE:
<221> NAME/KEY: MOD_RES
<222> LOCATION: (56)..(56)
<223> OTHER INFORMATION: S or G
<220> FEATURE:
<221> NAME/KEY: MOD_RES
<222> LOCATION: (57)..(57)
<223> OTHER INFORMATION: N, I, or S
<220> FEATURE:
<221> NAME/KEY: MOD_RES
<222> LOCATION: (58)..(58)
<223> OTHER INFORMATION: K or T
<220> FEATURE:
<221> NAME/KEY: MOD_RES
<222> LOCATION: (60)..(60)
<223> OTHER INFORMATION: Y or F
<220> FEATURE:
<221> NAME/KEY: MOD_RES
<222> LOCATION: (63)..(63)
<223> OTHER INFORMATION: S or P
<220> FEATURE:
<221> NAME/KEY: MOD_RES
<222> LOCATION: (76)..(76)
<223> OTHER INFORMATION: K or R
<220> FEATURE:
<221> NAME/KEY: MOD_RES
<222> LOCATION: (80)..(80)
<223> OTHER INFORMATION: Y or S
```

```
<220> FEATURE:
<221> NAME/KEY: MOD_RES
<222> LOCATION: (97)..(97)
<223> OTHER INFORMATION: A or V
<220> FEATURE:
<221> NAME/KEY: MOD_RES
<222> LOCATION: (98)..(98)
<223> OTHER INFORMATION: R or K
<220> FEATURE:
<221> NAME/KEY: MOD_RES
<222> LOCATION: (99)..(99)
<223> OTHER INFORMATION: D or R
<220> FEATURE:
<221> NAME/KEY: MOD_RES
<222> LOCATION: (100)..(100)
<223> OTHER INFORMATION: T or G
<220> FEATURE:
<221> NAME/KEY: MOD_RES
<222> LOCATION: (101)..(101)
<223> OTHER INFORMATION: A or T
<220> FEATURE:
<221> NAME/KEY: MOD_RES
<222> LOCATION: (103)..(103)
<223> OTHER INFORMATION: G, V, or I
<220> FEATURE:
<221> NAME/KEY: MOD_RES
<222> LOCATION: (104)..(104)
<223> OTHER INFORMATION: Y or absent
<220> FEATURE:
<221> NAME/KEY: MOD_RES
<222> LOCATION: (105)..(105)
<223> OTHER INFORMATION: Y or absent
<220> FEATURE:
<221> NAME/KEY: MOD_RES
<222> LOCATION: (106)..(106)
<223> OTHER INFORMATION: Y or absent
<220> FEATURE:
<221> NAME/KEY: MOD_RES
<222> LOCATION: (107)..(107)
<223> OTHER INFORMATION: Y or absent
<220> FEATURE:
<221> NAME/KEY: MOD_RES
<222> LOCATION: (108)..(108)
<223> OTHER INFORMATION: Y or G
<220> FEATURE:
<221> NAME/KEY: MOD_RES
<222> LOCATION: (109)..(109)
<223> OTHER INFORMATION: G or S
<220> FEATURE:
<221> NAME/KEY: MOD_RES
<222> LOCATION: (110)..(110)
<223> OTHER INFORMATION: M or F
<220> FEATURE:
<221> NAME/KEY: MOD_RES
<222> LOCATION: (112)..(112)
<223> OTHER INFORMATION: V or Y
<220> FEATURE:
<221> NAME/KEY: MOD_RES
<222> LOCATION: (118)..(118)
<223> OTHER INFORMATION: T or L
<220> FEATURE:
<221> NAME/KEY: MOD_RES
<222> LOCATION: (123)..(123)
<223> OTHER INFORMATION: S or absent

<400> SEQUENCE: 51

Xaa Val Gln Leu Xaa Xaa Ser Gly Gly Xaa Xaa Val Gln Pro Gly Xaa
1               5                   10                  15

Ser Leu Arg Leu Ser Cys Ala Ala Ser Gly Xaa Thr Phe Xaa Xaa Xaa
            20                  25                  30

Xaa Met Xaa Trp Val Arg Gln Ala Pro Gly Lys Gly Leu Glu Trp Val
        35                  40                  45

Xaa Xaa Ile Ser Xaa Xaa Gly Xaa Xaa Xaa Tyr Xaa Ala Asp Xaa Val
    50                  55                  60
```

```
Lys Gly Arg Phe Thr Ile Ser Arg Asp Asn Ser Xaa Asn Thr Leu Xaa
 65                  70                  75                  80

Leu Gln Met Asn Ser Leu Arg Ala Glu Asp Thr Ala Val Tyr Tyr Cys
                 85                  90                  95

Xaa Xaa Xaa Xaa Xaa Ala Xaa Xaa Xaa Xaa Xaa Xaa Xaa Xaa Asp Xaa
            100                 105                 110

Trp Gly Gln Gly Thr Xaa Val Thr Val Ser Xaa
            115                 120
```

```
<210> SEQ ID NO 52
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: L or M
<220> FEATURE:
<221> NAME/KEY: MOD_RES
<222> LOCATION: (10)..(10)
<223> OTHER INFORMATION: F or S
<220> FEATURE:
<221> NAME/KEY: MOD_RES
<222> LOCATION: (25)..(25)
<223> OTHER INFORMATION: A or S
<220> FEATURE:
<221> NAME/KEY: MOD_RES
<222> LOCATION: (30)..(30)
<223> OTHER INFORMATION: S or G
<220> FEATURE:
<221> NAME/KEY: MOD_RES
<222> LOCATION: (32)..(32)
<223> OTHER INFORMATION: F or W
<220> FEATURE:
<221> NAME/KEY: MOD_RES
<222> LOCATION: (38)..(38)
<223> OTHER INFORMATION: Q or L
<220> FEATURE:
<221> NAME/KEY: MOD_RES
<222> LOCATION: (40)..(40)
<223> OTHER INFORMATION: P or S
<220> FEATURE:
<221> NAME/KEY: MOD_RES
<222> LOCATION: (41)..(41)
<223> OTHER INFORMATION: G or E
<220> FEATURE:
<221> NAME/KEY: MOD_RES
<222> LOCATION: (45)..(45)
<223> OTHER INFORMATION: K or Q
<220> FEATURE:
<221> NAME/KEY: MOD_RES
<222> LOCATION: (46)..(46)
<223> OTHER INFORMATION: V or S
<220> FEATURE:
<221> NAME/KEY: MOD_RES
<222> LOCATION: (50)..(50)
<223> OTHER INFORMATION: V or A
<220> FEATURE:
<221> NAME/KEY: MOD_RES
<222> LOCATION: (51)..(51)
<223> OTHER INFORMATION: S or A
<220> FEATURE:
<221> NAME/KEY: MOD_RES
<222> LOCATION: (53)..(53)
<223> OTHER INFORMATION: T or S
<220> FEATURE:
<221> NAME/KEY: MOD_RES
<222> LOCATION: (54)..(54)
<223> OTHER INFORMATION: F or L
<220> FEATURE:
<221> NAME/KEY: MOD_RES
<222> LOCATION: (70)..(70)
```

```
<223> OTHER INFORMATION: E or D
<220> FEATURE:
<221> NAME/KEY: MOD_RES
<222> LOCATION: (74)..(74)
<223> OTHER INFORMATION: T or I
<220> FEATURE:
<221> NAME/KEY: MOD_RES
<222> LOCATION: (77)..(77)
<223> OTHER INFORMATION: S or N
<220> FEATURE:
<221> NAME/KEY: MOD_RES
<222> LOCATION: (91)..(91)
<223> OTHER INFORMATION: L or Y
<220> FEATURE:
<221> NAME/KEY: MOD_RES
<222> LOCATION: (93)..(93)
<223> OTHER INFORMATION: I or S
<220> FEATURE:
<221> NAME/KEY: MOD_RES
<222> LOCATION: (94)..(94)
<223> OTHER INFORMATION: F or Y
<220> FEATURE:
<221> NAME/KEY: MOD_RES
<222> LOCATION: (106)..(106)
<223> OTHER INFORMATION: S or I
<220> FEATURE:
<221> NAME/KEY: MOD_RES
<222> LOCATION: (108)..(108)
<223> OTHER INFORMATION: R or absent
<220> FEATURE:
<221> NAME/KEY: MOD_RES
<222> LOCATION: (109)..(109)
<223> OTHER INFORMATION: A or absent
<220> FEATURE:
<221> NAME/KEY: MOD_RES
<222> LOCATION: (110)..(110)
<223> OTHER INFORMATION: D or absent
<220> FEATURE:
<221> NAME/KEY: MOD_RES
<222> LOCATION: (111)..(111)
<223> OTHER INFORMATION: A or absent
<220> FEATURE:
<221> NAME/KEY: MOD_RES
<222> LOCATION: (112)..(112)
<223> OTHER INFORMATION: A or absent
<220> FEATURE:
<221> NAME/KEY: MOD_RES
<222> LOCATION: (113)..(113)
<223> OTHER INFORMATION: P or absent
<220> FEATURE:
<221> NAME/KEY: MOD_RES
<222> LOCATION: (114)..(114)
<223> OTHER INFORMATION: T or absent
<220> FEATURE:
<221> NAME/KEY: MOD_RES
<222> LOCATION: (115)..(115)
<223> OTHER INFORMATION: V or absent
<220> FEATURE:
<221> NAME/KEY: MOD_RES
<222> LOCATION: (116)..(116)
<223> OTHER INFORMATION: S or absent
<220> FEATURE:
<221> NAME/KEY: MOD_RES
<222> LOCATION: (117)..(117)
<223> OTHER INFORMATION: I or absent
<220> FEATURE:
<221> NAME/KEY: MOD_RES
<222> LOCATION: (118)..(118)
<223> OTHER INFORMATION: F or absent
<220> FEATURE:
<221> NAME/KEY: MOD_RES
<222> LOCATION: (119)..(119)
<223> OTHER INFORMATION: P or absent
<220> FEATURE:
<221> NAME/KEY: MOD_RES
<222> LOCATION: (120)..(120)
<223> OTHER INFORMATION: P or absent
<220> FEATURE:
<221> NAME/KEY: MOD_RES
```

```
<222> LOCATION: (121)..(121)
<223> OTHER INFORMATION: S or absent
<220> FEATURE:
<221> NAME/KEY: MOD_RES
<222> LOCATION: (122)..(122)
<223> OTHER INFORMATION: S or absent
<220> FEATURE:
<221> NAME/KEY: MOD_RES
<222> LOCATION: (123)..(123)
<223> OTHER INFORMATION: E or absent
<220> FEATURE:
<221> NAME/KEY: MOD_RES
<222> LOCATION: (124)..(124)
<223> OTHER INFORMATION: Q or absent

<400> SEQUENCE: 52

Asp Ile Gln Xaa Thr Gln Ser Pro Ser Xaa Leu Ser Ala Ser Val Gly
1               5                   10                  15

Asp Arg Val Thr Ile Thr Cys Arg Xaa Ser Gln Gly Ile Xaa Ser Xaa
            20                  25                  30

Leu Ala Trp Tyr Gln Xaa Lys Xaa Xaa Lys Ala Pro Xaa Xaa Leu Ile
            35                  40                  45

Tyr Xaa Xaa Ser Xaa Xaa Gln Ser Gly Val Pro Ser Arg Phe Ser Gly
    50                  55                  60

Ser Gly Ser Gly Thr Xaa Phe Thr Leu Xaa Ile Ser Xaa Leu Gln Pro
65                  70                  75                  80

Glu Asp Phe Ala Thr Tyr Tyr Cys Gln Gln Xaa Asn Xaa Xaa Pro Leu
                85                  90                  95

Thr Phe Gly Gly Gly Thr Lys Val Glu Xaa Lys Xaa Xaa Xaa Xaa Xaa
            100                 105                 110

Xaa Xaa Xaa Xaa Xaa Xaa Xaa Xaa Xaa Xaa Xaa Xaa
        115                 120

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: G or D
<220> FEATURE:
<221> NAME/KEY: MOD_RES
<222> LOCATION: (16)..(16)
<223> OTHER INFORMATION: G or E
<220> FEATURE:
<221> NAME/KEY: MOD_RES
<222> LOCATION: (27)..(27)
<223> OTHER INFORMATION: L or F
<220> FEATURE:
<221> NAME/KEY: MOD_RES
<222> LOCATION: (30)..(30)
<223> OTHER INFORMATION: R or S
<220> FEATURE:
<221> NAME/KEY: MOD_RES
<222> LOCATION: (31)..(31)
<223> OTHER INFORMATION: S or N
<220> FEATURE:
<221> NAME/KEY: MOD_RES
<222> LOCATION: (50)..(50)
<223> OTHER INFORMATION: G or A
<220> FEATURE:
<221> NAME/KEY: MOD_RES
<222> LOCATION: (57)..(57)
<223> OTHER INFORMATION: I, S, or N
<220> FEATURE:
<221> NAME/KEY: MOD_RES
```

-continued

```
<222> LOCATION: (60)..(60)
<223> OTHER INFORMATION: Y or F
<220> FEATURE:
<221> NAME/KEY: MOD_RES
<222> LOCATION: (63)..(63)
<223> OTHER INFORMATION: S or P
<220> FEATURE:
<221> NAME/KEY: MOD_RES
<222> LOCATION: (76)..(76)
<223> OTHER INFORMATION: K or R
<220> FEATURE:
<221> NAME/KEY: MOD_RES
<222> LOCATION: (80)..(80)
<223> OTHER INFORMATION: Y or S
<220> FEATURE:
<221> NAME/KEY: MOD_RES
<222> LOCATION: (97)..(97)
<223> OTHER INFORMATION: A or V
<220> FEATURE:
<221> NAME/KEY: MOD_RES
<222> LOCATION: (101)..(101)
<223> OTHER INFORMATION: A or T
<220> FEATURE:
<221> NAME/KEY: MOD_RES
<222> LOCATION: (103)..(103)
<223> OTHER INFORMATION: V or I

<400> SEQUENCE: 53

Glu Val Gln Leu Leu Glu Ser Gly Gly Xaa Leu Val Gln Pro Gly Xaa
1               5                   10                  15

Ser Leu Arg Leu Ser Cys Ala Ala Ser Gly Xaa Thr Phe Xaa Xaa Tyr
            20                  25                  30

Ala Met Thr Trp Val Arg Gln Ala Pro Gly Lys Gly Leu Glu Trp Val
        35                  40                  45

Ser Xaa Ile Ser Val Ser Gly Gly Xaa Thr Tyr Xaa Ala Asp Xaa Val
    50                  55                  60

Lys Gly Arg Phe Thr Ile Ser Arg Asp Asn Ser Xaa Asn Thr Leu Xaa
65                  70                  75                  80

Leu Gln Met Asn Ser Leu Arg Ala Glu Asp Thr Ala Val Tyr Tyr Cys
                85                  90                  95

Xaa Lys Arg Gly Xaa Ala Xaa Gly Ser Phe Asp Tyr Trp Gly Gln Gly
            100                 105                 110

Thr Leu Val Thr Val Ser Ser
        115

<210> SEQ ID NO 54
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: S or A
<220> FEATURE:
<221> NAME/KEY: MOD_RES
<222> LOCATION: (38)..(38)
<223> OTHER INFORMATION: Q or L
<220> FEATURE:
<221> NAME/KEY: MOD_RES
<222> LOCATION: (40)..(40)
<223> OTHER INFORMATION: P or S
<220> FEATURE:
<221> NAME/KEY: MOD_RES
<222> LOCATION: (45)..(45)
<223> OTHER INFORMATION: Q or K
<220> FEATURE:
<221> NAME/KEY: MOD_RES
```

```
<222> LOCATION: (74)..(74)
<223> OTHER INFORMATION: T or I
<220> FEATURE:
<221> NAME/KEY: MOD_RES
<222> LOCATION: (77)..(77)
<223> OTHER INFORMATION: N or S
<220> FEATURE:
<221> NAME/KEY: MOD_RES
<222> LOCATION: (108)..(108)
<223> OTHER INFORMATION: R or absent
<220> FEATURE:
<221> NAME/KEY: MOD_RES
<222> LOCATION: (109)..(109)
<223> OTHER INFORMATION: A or absent
<220> FEATURE:
<221> NAME/KEY: MOD_RES
<222> LOCATION: (110)..(110)
<223> OTHER INFORMATION: D or absent
<220> FEATURE:
<221> NAME/KEY: MOD_RES
<222> LOCATION: (111)..(111)
<223> OTHER INFORMATION: A or absent
<220> FEATURE:
<221> NAME/KEY: MOD_RES
<222> LOCATION: (112)..(112)
<223> OTHER INFORMATION: A or absent
<220> FEATURE:
<221> NAME/KEY: MOD_RES
<222> LOCATION: (113)..(113)
<223> OTHER INFORMATION: P or absent
<220> FEATURE:
<221> NAME/KEY: MOD_RES
<222> LOCATION: (114)..(114)
<223> OTHER INFORMATION: T or absent
<220> FEATURE:
<221> NAME/KEY: MOD_RES
<222> LOCATION: (115)..(115)
<223> OTHER INFORMATION: V or absent
<220> FEATURE:
<221> NAME/KEY: MOD_RES
<222> LOCATION: (116)..(116)
<223> OTHER INFORMATION: S or absent
<220> FEATURE:
<221> NAME/KEY: MOD_RES
<222> LOCATION: (117)..(117)
<223> OTHER INFORMATION: I or absent
<220> FEATURE:
<221> NAME/KEY: MOD_RES
<222> LOCATION: (118)..(118)
<223> OTHER INFORMATION: F or absent
<220> FEATURE:
<221> NAME/KEY: MOD_RES
<222> LOCATION: (119)..(119)
<223> OTHER INFORMATION: P or absent
<220> FEATURE:
<221> NAME/KEY: MOD_RES
<222> LOCATION: (120)..(120)
<223> OTHER INFORMATION: P or absent
<220> FEATURE:
<221> NAME/KEY: MOD_RES
<222> LOCATION: (121)..(121)
<223> OTHER INFORMATION: S or absent
<220> FEATURE:
<221> NAME/KEY: MOD_RES
<222> LOCATION: (122)..(122)
<223> OTHER INFORMATION: S or absent
<220> FEATURE:
<221> NAME/KEY: MOD_RES
<222> LOCATION: (123)..(123)
<223> OTHER INFORMATION: E or absent
<220> FEATURE:
<221> NAME/KEY: MOD_RES
<222> LOCATION: (124)..(124)
<223> OTHER INFORMATION: Q or absent

<400> SEQUENCE: 54

Asp Ile Gln Met Thr Gln Ser Pro Ser Ser Leu Ser Ala Ser Val Gly
1               5                   10                  15
```

```
Asp Arg Val Thr Ile Thr Cys Arg Xaa Ser Gln Gly Ile Gly Ser Trp
             20                  25                  30

Leu Ala Trp Tyr Gln Xaa Lys Xaa Glu Lys Ala Pro Xaa Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Xaa Ile Ser Xaa Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys Xaa Xaa Xaa Xaa Xaa
            100                 105                 110

Xaa Xaa Xaa Xaa Xaa Xaa Xaa Xaa Xaa Xaa Xaa Xaa
            115                 120

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: F or L
<220> FEATURE:
<221> NAME/KEY: MOD_RES
<222> LOCATION: (5)..(5)
<223> OTHER INFORMATION: S or R
<220> FEATURE:
<221> NAME/KEY: MOD_RES
<222> LOCATION: (6)..(6)
<223> OTHER INFORMATION: R, S, or N
<220> FEATURE:
<221> NAME/KEY: MOD_RES
<222> LOCATION: (7)..(7)
<223> OTHER INFORMATION: N or Y
<220> FEATURE:
<221> NAME/KEY: MOD_RES
<222> LOCATION: (8)..(8)
<223> OTHER INFORMATION: G or A
<220> FEATURE:
<221> NAME/KEY: MOD_RES
<222> LOCATION: (10)..(10)
<223> OTHER INFORMATION: H or T

<400> SEQUENCE: 55

Gly Xaa Thr Phe Xaa Xaa Xaa Xaa Met Xaa
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V, G, A, or absent
<220> FEATURE:
<221> NAME/KEY: MOD_RES
<222> LOCATION: (4)..(4)
<223> OTHER INFORMATION: Y or V
<220> FEATURE:
<221> NAME/KEY: MOD_RES
<222> LOCATION: (5)..(5)
```

```
<223> OTHER INFORMATION: D or S
<220> FEATURE:
<221> NAME/KEY: MOD_RES
<222> LOCATION: (7)..(7)
<223> OTHER INFORMATION: S or G
<220> FEATURE:
<221> NAME/KEY: MOD_RES
<222> LOCATION: (8)..(8)
<223> OTHER INFORMATION: N, I, or S
<220> FEATURE:
<221> NAME/KEY: MOD_RES
<222> LOCATION: (9)..(9)
<223> OTHER INFORMATION: K or T
<220> FEATURE:
<221> NAME/KEY: MOD_RES
<222> LOCATION: (11)..(11)
<223> OTHER INFORMATION: Y or F
<220> FEATURE:
<221> NAME/KEY: MOD_RES
<222> LOCATION: (14)..(14)
<223> OTHER INFORMATION: S or P

<400> SEQUENCE: 56

Xaa Ile Ser Xaa Xaa Gly Xaa Xaa Xaa Tyr Xaa Ala Asp Xaa Val Lys
1               5                   10                  15

Gly

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R or absent
<220> FEATURE:
<221> NAME/KEY: MOD_RES
<222> LOCATION: (2)..(2)
<223> OTHER INFORMATION: D or G
<220> FEATURE:
<221> NAME/KEY: MOD_RES
<222> LOCATION: (3)..(3)
<223> OTHER INFORMATION: T or A
<220> FEATURE:
<221> NAME/KEY: MOD_RES
<222> LOCATION: (5)..(5)
<223> OTHER INFORMATION: A, I, or V
<220> FEATURE:
<221> NAME/KEY: MOD_RES
<222> LOCATION: (7)..(7)
<223> OTHER INFORMATION: Y or S
<220> FEATURE:
<221> NAME/KEY: MOD_RES
<222> LOCATION: (8)..(8)
<223> OTHER INFORMATION: Y or F
<220> FEATURE:
<221> NAME/KEY: MOD_RES
<222> LOCATION: (9)..(9)
<223> OTHER INFORMATION: Y or D
<220> FEATURE:
<221> NAME/KEY: MOD_RES
<222> LOCATION: (11)..(11)
<223> OTHER INFORMATION: Y or absent
<220> FEATURE:
<221> NAME/KEY: MOD_RES
<222> LOCATION: (12)..(12)
<223> OTHER INFORMATION: G or absent
<220> FEATURE:
<221> NAME/KEY: MOD_RES
<222> LOCATION: (13)..(13)
<223> OTHER INFORMATION: M or absent
<220> FEATURE:
<221> NAME/KEY: MOD_RES
```

```
<222> LOCATION: (14)..(14)
<223> OTHER INFORMATION: D or absent
<220> FEATURE:
<221> NAME/KEY: MOD_RES
<222> LOCATION: (15)..(15)
<223> OTHER INFORMATION: V or absent

<400> SEQUENCE: 57

Xaa Xaa Xaa Ala Xaa Gly Xaa Xaa Xaa Tyr Xaa Xaa Xaa Xaa Xaa
1               5                   10                  15

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A or S
<220> FEATURE:
<221> NAME/KEY: MOD_RES
<222> LOCATION: (7)..(7)
<223> OTHER INFORMATION: S or G
<220> FEATURE:
<221> NAME/KEY: MOD_RES
<222> LOCATION: (9)..(9)
<223> OTHER INFORMATION: F or W

<400> SEQUENCE: 58

Arg Xaa Ser Gln Gly Ile Xaa Ser Xaa Leu Ala
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or absent
<220> FEATURE:
<221> NAME/KEY: MOD_RES
<222> LOCATION: (2)..(2)
<223> OTHER INFORMATION: A or absent
<220> FEATURE:
<221> NAME/KEY: MOD_RES
<222> LOCATION: (4)..(4)
<223> OTHER INFORMATION: S or T
<220> FEATURE:
<221> NAME/KEY: MOD_RES
<222> LOCATION: (5)..(5)
<223> OTHER INFORMATION: L or F
<220> FEATURE:
<221> NAME/KEY: MOD_RES
<222> LOCATION: (8)..(8)
<223> OTHER INFORMATION: G or absent
<220> FEATURE:
<221> NAME/KEY: MOD_RES
<222> LOCATION: (9)..(9)
<223> OTHER INFORMATION: V or absent

<400> SEQUENCE: 59

Xaa Xaa Ser Xaa Xaa Gln Ser Xaa Xaa
1               5

<210> SEQ ID NO 60
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Y or L
<220> FEATURE:
<221> NAME/KEY: MOD_RES
<222> LOCATION: (5)..(5)
<223> OTHER INFORMATION: S or I
<220> FEATURE:
<221> NAME/KEY: MOD_RES
<222> LOCATION: (6)..(6)
<223> OTHER INFORMATION: Y or F

<400> SEQUENCE: 60

Gln Gln Xaa Asn Xaa Xaa Pro Leu Thr
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: F or L
<220> FEATURE:
<221> NAME/KEY: MOD_RES
<222> LOCATION: (5)..(5)
<223> OTHER INFORMATION: S or R
<220> FEATURE:
<221> NAME/KEY: MOD_RES
<222> LOCATION: (6)..(6)
<223> OTHER INFORMATION: S or N

<400> SEQUENCE: 61

Gly Xaa Thr Phe Xaa Xaa Tyr Ala Met Thr
1               5                   10

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, A, or absent
<220> FEATURE:
<221> NAME/KEY: MOD_RES
<222> LOCATION: (8)..(8)
<223> OTHER INFORMATION: I, S, or N
<220> FEATURE:
<221> NAME/KEY: MOD_RES
<222> LOCATION: (11)..(11)
<223> OTHER INFORMATION: Y or F
<220> FEATURE:
<221> NAME/KEY: MOD_RES
<222> LOCATION: (14)..(14)
<223> OTHER INFORMATION: S or P

<400> SEQUENCE: 62

Xaa Ile Ser Val Ser Gly Gly Xaa Thr Tyr Xaa Ala Asp Xaa Val Lys
1               5                   10                  15
```

Gly

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: T or A
<220> FEATURE:
<221> NAME/KEY: MOD_RES
<222> LOCATION: (5)..(5)
<223> OTHER INFORMATION: I or V

<400> SEQUENCE: 63

Arg Gly Xaa Ala Xaa Gly Ser Phe Asp Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: S or A

<400> SEQUENCE: 64

Arg Xaa Ser Gln Gly Ile Gly Ser Trp Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ser Ser Leu Gln Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Tyr Asn Ser Tyr Pro Leu Thr
1               5

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser
        115
```

<210> SEQ ID NO 68
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys
            100                 105
```

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Gly Tyr Ser Phe Thr Gly Tyr Thr Met Asn
1               5                   10
```

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 70

Leu Ile Thr Pro Tyr Asn Gly Ala Ser Ser Tyr Asn Gln
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Tyr Asp Gly Arg Gly Phe Asp Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ala Ser Ser Ser Val Ser Tyr Met His
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Thr Ser Lys Leu Ala Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Trp Ser Lys His Pro Leu Thr
1               5

<210> SEQ ID NO 75
<211> LENGTH: 630
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30
```

```
Pro Ser Arg Thr Leu Ala Gly Glu Thr Gly Gln Glu Ala Ala Pro Leu
        35                  40                  45

Asp Gly Val Leu Ala Asn Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
                100                 105                 110

Glu Asp Leu Asp Ala Leu Pro Leu Asp Leu Leu Leu Phe Leu Asn Pro
                115                 120                 125

Asp Ala Phe Ser Gly Pro Gln Ala Cys Thr Arg Phe Phe Ser Arg Ile
            130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
            195                 200                 205

Val Ser Cys Pro Gly Pro Leu Asp Gln Asp Gln Gln Glu Ala Ala Arg
210                 215                 220

Ala Ala Leu Gln Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
            275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
                355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
    435                 440                 445
```

Leu Cys Ser Leu Ser Pro Glu Glu Leu Ser Ser Val Pro Pro Ser Ser
            450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
            485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
            515                 520                 525

Ala Thr Phe Met Lys Leu Arg Thr Asp Ala Val Leu Pro Leu Thr Val
            530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
            565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
            595                 600                 605

Pro Cys Leu Leu Gly Pro Gly Pro Val Leu Thr Val Leu Ala Leu Leu
            610                 615                 620

Leu Ala Ser Thr Leu Ala
625                 630

<210> SEQ ID NO 76
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Phe
            50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
            85                  90                  95

Ala Arg Tyr Tyr Asp Asp His Tyr Ser Leu Asp Tyr Trp Gly Gln Gly
            100                 105                 110

Thr Pro Val Thr Val Ser Ser
            115

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Tyr Thr Phe Thr Arg Tyr Thr Met His
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Asn Pro Ser Arg Gly Tyr Thr Asn Tyr Asn Gln Lys Phe Lys Asp
1               5                   10                  15

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Tyr Asp Asp His Tyr Ser Leu Asp Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Ala Ser Ser Ser Val Ser Tyr Met Asn
1               5                   10

```
<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Thr Ser Lys Leu Ala Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Gln Trp Ser Ser Asn Pro Phe Thr
1               5
```

ANTI-MESOTHELIN ANTIGEN-BINDING MOLECULES AND USES THEREOF

CROSS REFERENCE TO RELATED APPLICATION

This application claims the benefit under 35 USC § 119(e) of U.S. Provisional Application No. 63/006,308, filed Apr. 7, 2020, which is incorporated herein by reference in its entirety for all purposes.

REFERENCE TO A SEQUENCE LISTING

This application incorporates by reference the Sequence Listing submitted in Computer Readable Form as file 19-157-US-NP_Sequence, created on Apr. 6, 2021 and containing 58,817 bytes.

FIELD OF THE INVENTION

The present disclosure relates to antibodies and antigen-binding molecules that are specific for human mesothelin (MSLN), and methods of use thereof. The present disclosure includes bispecific antigen-binding molecules that bind MSLN and a T cell antigen (e.g., CD3), and methods of use thereof.

BACKGROUND

Mesothelin (MSLN) is a cell surface glycoprotein that is highly expressed in pancreatic cancers, ovarian cancers, mesotheliomas, and some other cancer types. Mesothelin is expressed on normal mesothelial cells lining the pleura, pericardium, and peritoneum, but the limited distribution of mesothelin on normal tissues makes it a promising target for tumor-specific therapy. The mesothelin gene encodes a 69-kDa precursor protein that is processed to a 40-kDa membrane-bound protein termed mesothelin and a 31-kDa shed fragment called megakaryocyte-potentiating factor (MPF) that is released from the cell. A soluble form of mesothelin is also known to exist, and is likely the result of an abnormal splicing event resulting in a frameshift mutation and premature termination, which deletes the amino acids at the C-terminus that are responsible for the protein's association with the cell membrane. Hassan et al., *Clinical Cancer Research*, 10:3937-3942, 2004. Additional evidence suggests that the extracellular domain of membrane-bound mesothelin can also be shed from tumor cells, although the precise mechanism associated with this shedding has not yet been elucidated. Ho and Lively, *Cancer Epidemiol Biomarkers Prev.*, 15(9):1751, 2006. These soluble forms of mesothelin can impede tumor cell-directed immunotherapies by producing an antigen sink that binds anti-MSLN antibodies.

CD3 is a homodimeric or heterodimeric antigen expressed on T cells in association with the T cell receptor complex (TCR) and is required for T cell activation. Functional CD3 is formed from the dimeric association of two of four different chains: epsilon, zeta, delta and gamma. The CD3 dimeric arrangements include gamma/epsilon, delta/epsilon and zeta/zeta. Antibodies against CD3 have been shown to cluster CD3 on T cells, thereby causing T cell activation in a manner similar to the engagement of the TCR by peptide-loaded MHC molecules. Thus, anti-CD3 antibodies have been proposed for therapeutic purposes involving the activation of T cells. In addition, bispecific antibodies that are capable of binding CD3 and a target antigen have been proposed for therapeutic uses involving targeting T cell immune responses to tissues and cells expressing the target antigen.

Antigen-binding molecules that target MSLN, including bispecific antigen-binding molecules that bind both MSLN and a T cell antigen (e.g., CD3) would be useful in therapeutic settings in which specific targeting and T cell-mediated killing of cells that express MSLN is desired.

BRIEF SUMMARY OF THE DISCLOSURE

In one aspect, the present invention provides an antigen-binding molecule comprising an antigen-binding domain that specifically binds human mesothelin (MSLN), wherein the antigen-binding domain comprises: (a) the complementarity determining regions (CDRs) of a heavy chain variable region (HCVR) comprising an amino acid sequence selected from the group consisting of SEQ ID NOs: 1, 9, 17, 25, 33, 41, 51, and 53; and (b) the CDRs of a light chain variable region (LCVR). In some cases, the antigen-binding molecule comprises the CDRs of an LCVR comprising an amino acid sequence selected from the group consisting of SEQ ID NOs: 2, 10, 18, 26, 34, 42, 52 and 54. In some embodiments, the antigen-binding domain comprises heavy and light chain CDRs of a HCVR/LCVR amino acid sequence pair selected from the group consisting of: SEQ ID NOs: 1/2, 9/10, 17/18, 25/26, 33/34, 41/42, 51/52, and 53/54.

In some embodiments, the antigen-binding domain comprises HCDR1-HCDR2-HCDR3-LCDR1-LCDR2-LCDR3 domains, respectively, selected from the group consisting of SEQ ID NOs: 3-4-5-6-7-8, 11-12-13-14-15-16, 19-20-21-22-23-24, 27-28-29-30-31-32, 35-36-37-38-39-40, 43-44-45-46-47-48, 55-56-57-58-59-60, and 61-62-63-64-65-66. In some cases, the antigen-binding domain comprises HCDR1-HCDR2-HCDR3-LCDR1-LCDR2-LCDR3 domains, respectively, comprising SEQ ID NOs: 3-4-5-6-7-8. In some cases, the antigen-binding domain comprises HCDR1-HCDR2-HCDR3-LCDR1-LCDR2-LCDR3 domains, respectively, comprising SEQ ID NOs: 11-12-13-14-15-16. In some cases, the antigen-binding domain comprises HCDR1-HCDR2-HCDR3-LCDR1-LCDR2-LCDR3 domains, respectively, comprising SEQ ID NOs: 19-20-21-22-23-24. In some cases, the antigen-binding domain comprises HCDR1-HCDR2-HCDR3-LCDR1-LCDR2-LCDR3 domains, respectively, comprising SEQ ID NOs: 27-28-29-30-31-32. In some cases, the antigen-binding domain comprises HCDR1-HCDR2-HCDR3-LCDR1-LCDR2-LCDR3 domains, respectively, comprising SEQ ID NOs: 35-36-37-38-39-40. In some cases, the antigen-binding domain comprises HCDR1-HCDR2-HCDR3-LCDR1-LCDR2-LCDR3 domains, respectively, comprising SEQ ID NOs: 43-44-45-46-47-48. In some cases, the antigen-binding domain comprises HCDR1-HCDR2-HCDR3-LCDR1-LCDR2-LCDR3 domains, respectively, comprising SEQ ID NOs: 55-56-57-58-59-60. In some cases, the antigen-binding domain comprises HCDR1-HCDR2-HCDR3-LCDR1-LCDR2-LCDR3 domains, respectively, comprising SEQ ID NOs: 61-62-63-64-65-66.

In some embodiments, the antigen-binding domain comprises a HCVR comprising an amino acid sequence selected from the group consisting of SEQ ID NOs: 1, 9, 17, 25, 33, 41, 51, and 53, and a LCVR comprising an amino acid sequence selected from the group consisting of SEQ ID NOs: 2, 10, 18, 26, 34, 42, 52 and 54. In some cases, the antigen-binding domain comprises a HCVR with at least 90% sequence identity to an amino acid sequence selected from the group consisting of SEQ ID NOs: 1, 9, 17, 25, 33, 41, 51, and 53. In some cases, the HCVR has at least 95% sequence identity to an amino acid sequence selected from the group consisting of SEQ ID NOs: 1, 9, 17, 25, 33, 41, 51, and 53. In some cases, the HCVR has at least 99% sequence identity to an amino acid sequence selected from the group consisting of SEQ ID NOs: 1, 9, 17, 25, 33, 41, 51, and 53. In some cases, the antigen-binding domain comprises a LCVR with at least 90% sequence identity to an amino acid sequence selected from the group consisting of SEQ ID NOs: 2, 10, 18, 26, 34, 42, 52 and 54. In some cases, the antigen-binding domain comprises a LCVR with at least 95% sequence identity to an amino acid sequence selected from the group consisting of SEQ ID NOs: 2, 10, 18, 26, 34, 42, 52 and 54. In some cases, the antigen-binding domain comprises a LCVR with at least 99% sequence identity to an amino acid sequence selected from the group consisting of SEQ ID NOs: 2, 10, 18, 26, 34, 42, 52 and 54. In various embodiments, the antigen-binding molecule comprises the CDRs of a HCVR/LCVR amino acid sequence pair selected from the group consisting of: SEQ ID NOs: 1/2, 9/10, 17/18, 25/26, 33/34, 41/42, 51/52, and 53/54, and an HCVR/LCVR amino acid sequence pair with at least 90%, 95%, or 99% sequence identity to SEQ ID NOs: 1/2, 9/10, 17/18, 25/26, 33/34, 41/42, 51/52, and 53/54, respectively. For example, an antigen-binding molecule comprising the CDRs of an HCVR/LCVR of SEQ ID NOs: 1/2 may have a HCVR with 90%, 95%, or 99% sequence identity to SEQ ID NO: 1, and a LCVR with 90%, 95%, or 99% sequence identity to SEQ ID NO: 2.

In some embodiments, the antigen-binding domain comprises a HCVR/LCVR amino acid sequence pair selected from the group consisting of SEQ ID NOs: 1/2, 9/10, 17/18, 25/26, 33/34, 41/42, 51/52, and 53/54. In some cases, the antigen-binding domain comprises a HCVR comprising the amino acid sequence of SEQ ID NO: 1, and a LCVR comprising the amino acid sequence of SEQ ID NO: 2. In some cases, the antigen-binding domain comprises a HCVR comprising the amino acid sequence of SEQ ID NO: 9, and a LCVR comprising the amino acid sequence of SEQ ID NO: 10. In some cases, the antigen-binding domain comprises a HCVR comprising the amino acid sequence of SEQ ID NO: 17, and a LCVR comprising the amino acid sequence of SEQ ID NO: 18. In some cases, the antigen-binding domain comprises a HCVR comprising the amino acid sequence of SEQ ID NO: 25, and a LCVR comprising the amino acid sequence of SEQ ID NO: 26. In some cases, the antigen-binding domain comprises a HCVR comprising the amino acid sequence of SEQ ID NO: 33, and a LCVR comprising the amino acid sequence of SEQ ID NO: 34. In some cases, the antigen-binding domain comprises a HCVR comprising the amino acid sequence of SEQ ID NO: 41, and a LCVR comprising the amino acid sequence of SEQ ID NO: 42. In some cases, the antigen-binding domain comprises a HCVR comprising the amino acid sequence of SEQ ID NO: 51, and a LCVR comprising the amino acid sequence of SEQ ID NO: 52. In some cases, the antigen-binding domain comprises a HCVR comprising the amino acid sequence of SEQ ID NO: 53, and a LCVR comprising the amino acid sequence of SEQ ID NO: 54.

In any of the various embodiments, the antigen-binding molecule is a monoclonal antibody or antigen-binding fragment thereof. In any of the various embodiments, the antigen-binding molecule is a bispecific antibody or antigen-binding fragment thereof comprising a second antigen-binding domain.

In any of the various embodiments, the antigen-binding molecule is a bispecific antigen-binding molecule comprising a second antigen-binding domain. In some cases, the bispecific antigen-binding molecule comprises two Fab domains covalently attached, respectively, to two immunoglobulin Fc domains, and two scFv domains covalently attached, respectively, to the two Fab domains. In some cases, the two Fab domains each comprise an antigen-binding domain that specifically binds human MSLN, and the two scFv domains each comprise a second antigen-binding domain. In some cases, the scFv domains are covalently attached, respectively, via a linker between the heavy chain portion of each of the two scFv domains and the C-terminus of the light chain portion of each of the two Fab domains. In some cases, the antigen-binding domain and the second antigen-binding domain each comprise a scFv domain, and the two scFv domains are covalently attached to two immunoglobulin Fc domains.

In any of the various embodiments, the bispecific antigen-binding molecule comprises a second antigen-binding domain that specifically binds a T cell antigen. In some cases, the T cell antigen is selected from CD3, CD27, CD28, 4-1BB, OX40 or CD2. In some cases, the T cell antigen is CD3.

In any of the various embodiments, the antigen-binding molecule comprises an immunoglobulin Fc domain or Fc domains that have reduced binding to Fcγ receptors relative to a wild-type Fc domain of the same isotype.

In any of the various embodiments, the antigen-binding molecule comprises an immunoglobulin Fc domain or Fc domains that are human immunoglobulin Fc domains of isotype IgG1, IgG2, IgG3 or IgG4.

In any of the various embodiments, the antigen-binding molecule comprises an antigen-binding domain that specifically binds human mesothelin at an epitope within SEQ ID NO: 50. In any of the various embodiments, the antigen-binding molecule comprises an antigen-binding domain that specifically binds human mesothelin at an epitope on the mature human mesothelin protein that is destroyed by a cleavage event that forms soluble mesothelin.

In one aspect, the present invention provides a pharmaceutical composition comprising an antigen-binding molecule as discussed above or herein, and a pharmaceutically acceptable carrier or diluent.

In one aspect, the present invention provides an isolated polynucleotide molecule comprising a polynucleotide sequence that encodes a HCVR or a LCVR of an antigen-binding molecule as discussed above or herein. The present invention also provides a pair of isolated polynucleotide molecules that encode a HCVR and a LCVR of an antigen-binding molecule as discussed above or herein.

In one aspect, the present invention provides an expression vector comprising the polynucleotide or polynucleotides discussed above or herein.

In one aspect, the present invention provides a host cell comprising the polynucleotide(s), or the expression vector discussed above or herein.

In one aspect, the present invention provides a method for treating a MSLN-positive cancer in a subject, wherein the method comprises administering to the subject an antigen-binding molecule as discussed above or herein, or a pharmaceutical composition as discussed above or herein. In some cases, the MSLN-positive cancer is ovarian cancer, pancreatic cancer or a mesothelioma.

In one aspect, the present invention provides for use of an antigen-binding molecule as discussed above or herein, or a pharmaceutical composition as discussed above or herein, in the treatment of a disease or disorder associated with expression of MSLN. In some cases, the disease or disorder is a MSLN-positive cancer. The present invention also provides an antigen-binding molecule as discussed above or herein for use in medicine, or for use in the treatment of a disease or disorder associated with expression of MSLN, or for use in the treatment of a MSLN-positive cancer. In some cases, the MSLN-positive cancer is ovarian cancer, pancreatic cancer or a mesothelioma.

In one aspect, the present invention provides a compound comprising an antigen-binding molecule as discussed above or herein for use in medicine, or a compound comprising an antigen-binding molecule as discussed above or herein for use in the treatment of cancer.

In one aspect, the present invention provides for use of an antigen-binding molecule as discussed above or herein in the manufacture of a medicament for use in the treatment of a MSLN-positive cancer. In some cases, the MSLN-positive cancer is ovarian cancer, pancreatic cancer or a mesothelioma.

In one aspect, the present invention provides a method of detecting MSLN in a biological sample, wherein the method comprises: obtaining a biological sample from a subject, and detecting whether MSLN is present in the biological sample by contacting the biological sample with an anti-MSLN antibody or antigen-binding fragment thereof and detecting binding between MSLN and the anti-MSLN antibody or antigen-binding fragment. In some cases, the biological sample is a tissue sample or a fluid sample. In some cases, the anti-MSLN antibody or antigen-binding fragment is a monoclonal antibody or antigen-binding fragment with anti-MSLN antigen binding domains as discussed above or herein.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

BRIEF DESCRIPTION OF THE DRAWINGS

FIGS. 5A, 5B, 5C and 5D illustrate the MSLN architecture and post-translational modifications (FIG. 5A), a crystal structure of an amatuximab/MSLN complex (PDB ID: 4F3F) confirming that amatuximab binds at a membrane distal epitope (FIG. 5B), a schematic showing antibodies binding to epitopes that can discriminate between membrane-bound MSLN and shed MSLN (FIG. 5C), and the primary sequence of MSLN annotated with the amatuximab epitope. The sequence illustrated in FIG. 5D is set forth in SEQ ID NO: 75.

FIGS. 9B and 9C illustrate a summary of flow cytometry data and transcript expression, as determined by quantitative polymerase chain reaction (qPCR), quantifying MSLN expression in various cell lines.

Figure 3B:
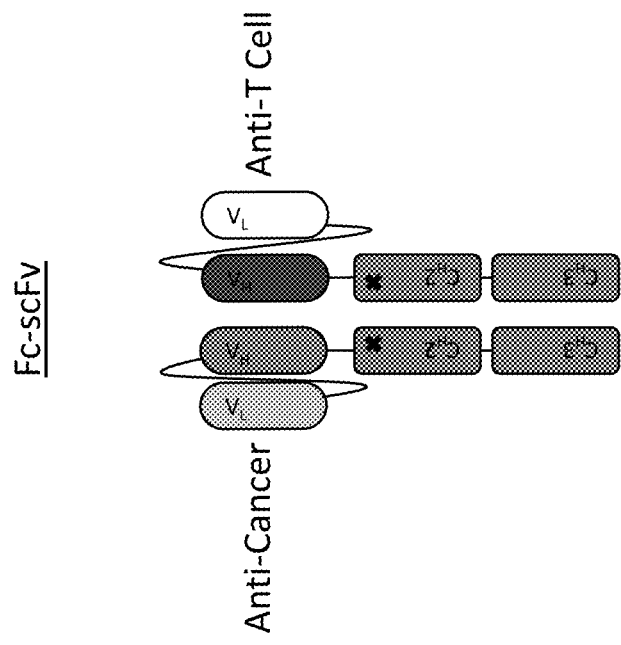
FIGS. 3A and 3B illustrate two different bispecific formats combining cancer antigen-binding domains with a T cell antigen-binding domain. In the IgG-scFv format illustrated in FIG. 3A, traditional Fab domains (e.g., anti-cancer domains) are linked to scFv domains (e.g., anti-T cell domains) and an immunoglobulin Fc domain, while in the Fc-scFv format illustrated in FIG. 3B, scFv domains comprising anti-cancer and anti-T cell antigen-binding domains are linked to an immunoglobulin Fc domain. The crosses shown in the CH2 domains represent optional mutations at a glycosylation site to disrupt interaction with an Fc receptor.
Figure 3A:
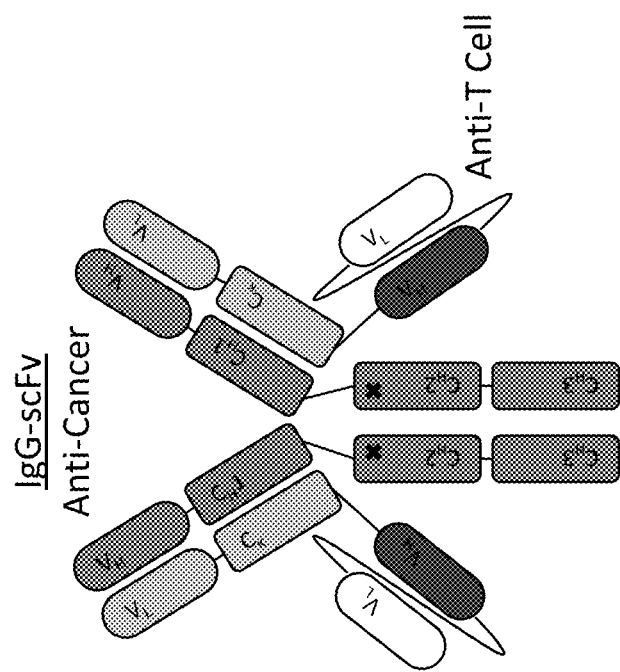
Figures 4A, 4B:
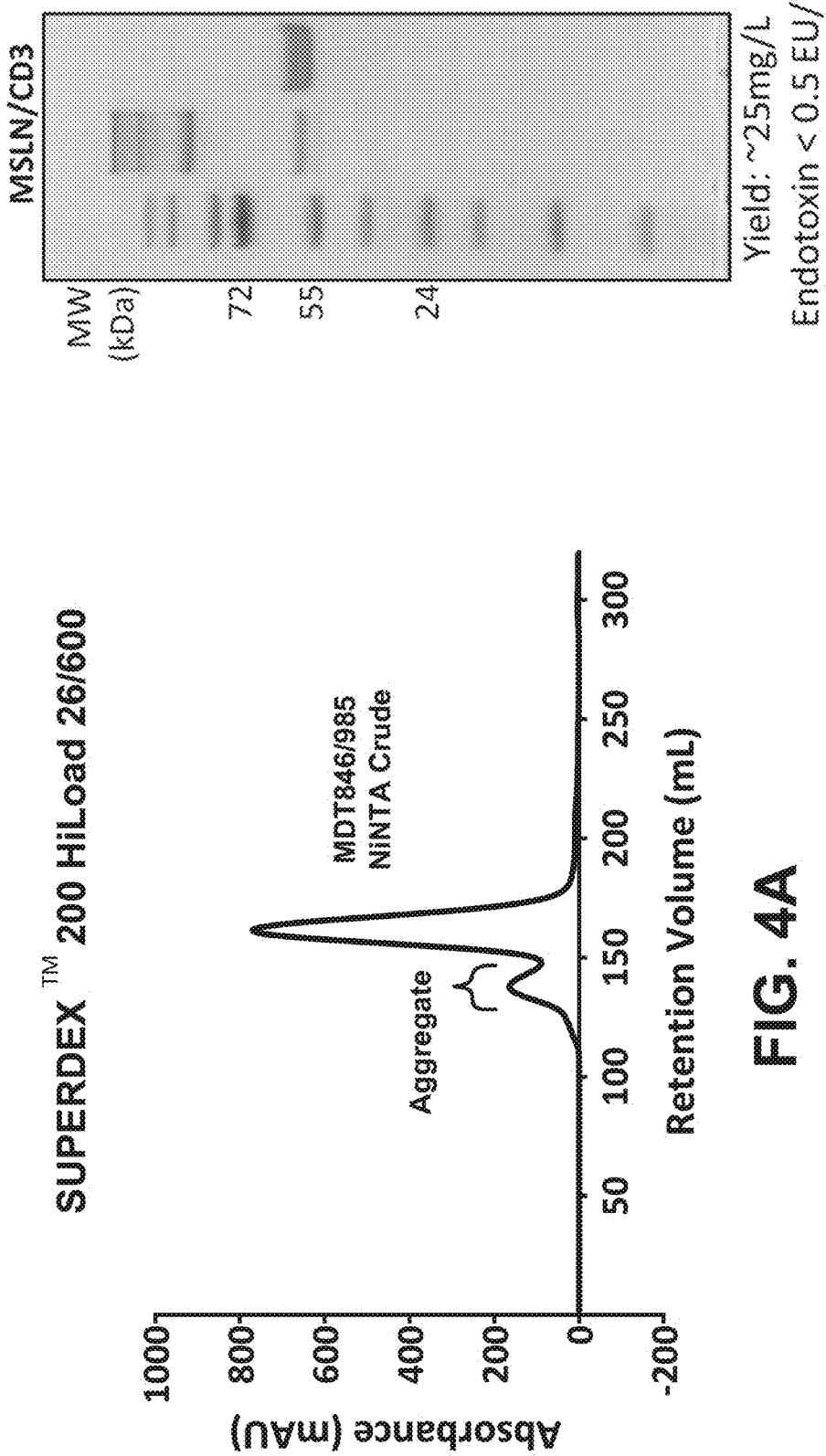
FIGS. 4A and 4B illustrate a size exclusion chromatogram showing the protein behavior post NiNTA purification and highlighting the low degree of aggregation of a bispecific molecule having the structure of FIG. 3A (FIG. 4A), and an SDS-PAGE gel showing the purified protein under non-reducing and reducing conditions (FIG. 4B).
Figure 4C:
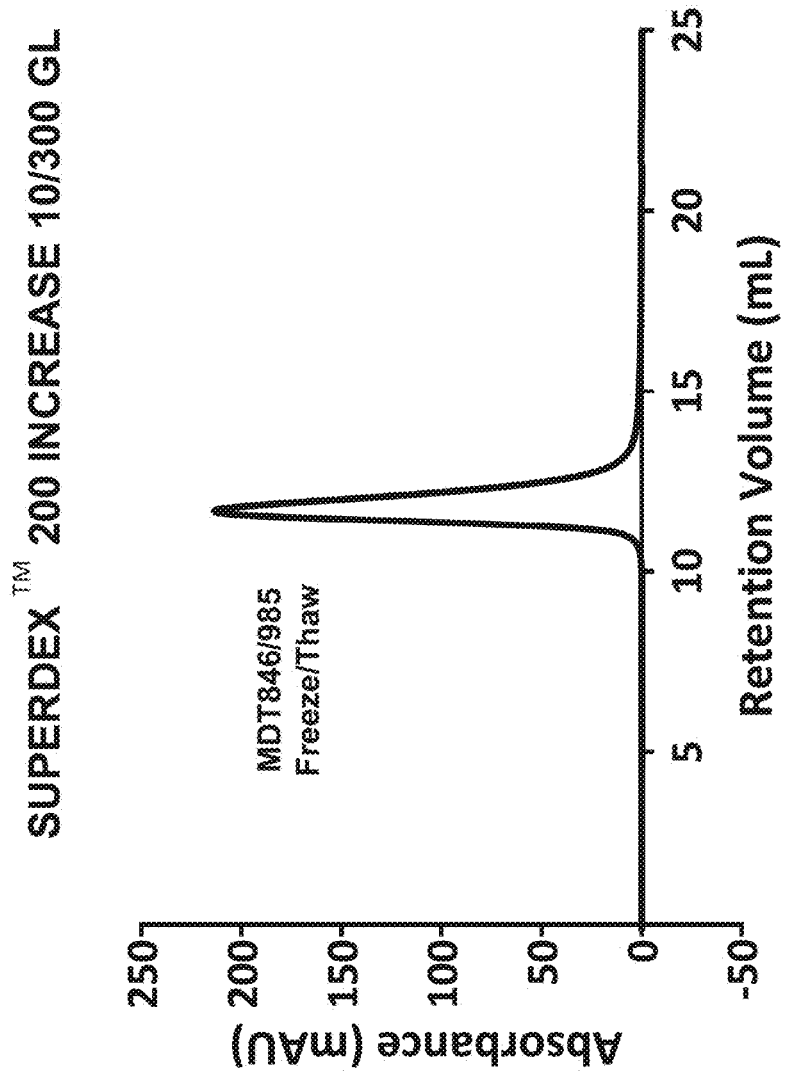
FIGS. 4C and 4D illustrate a size exclusion chromatogram showing the final protein product (structure of FIG. 3A) following a freeze/thaw cycle (FIG. 4C), and a UV/Vis quantitation and dynamic light scattering analysis of the final protein product free of higher order aggregates (FIG. 4D).
Figure 4D:
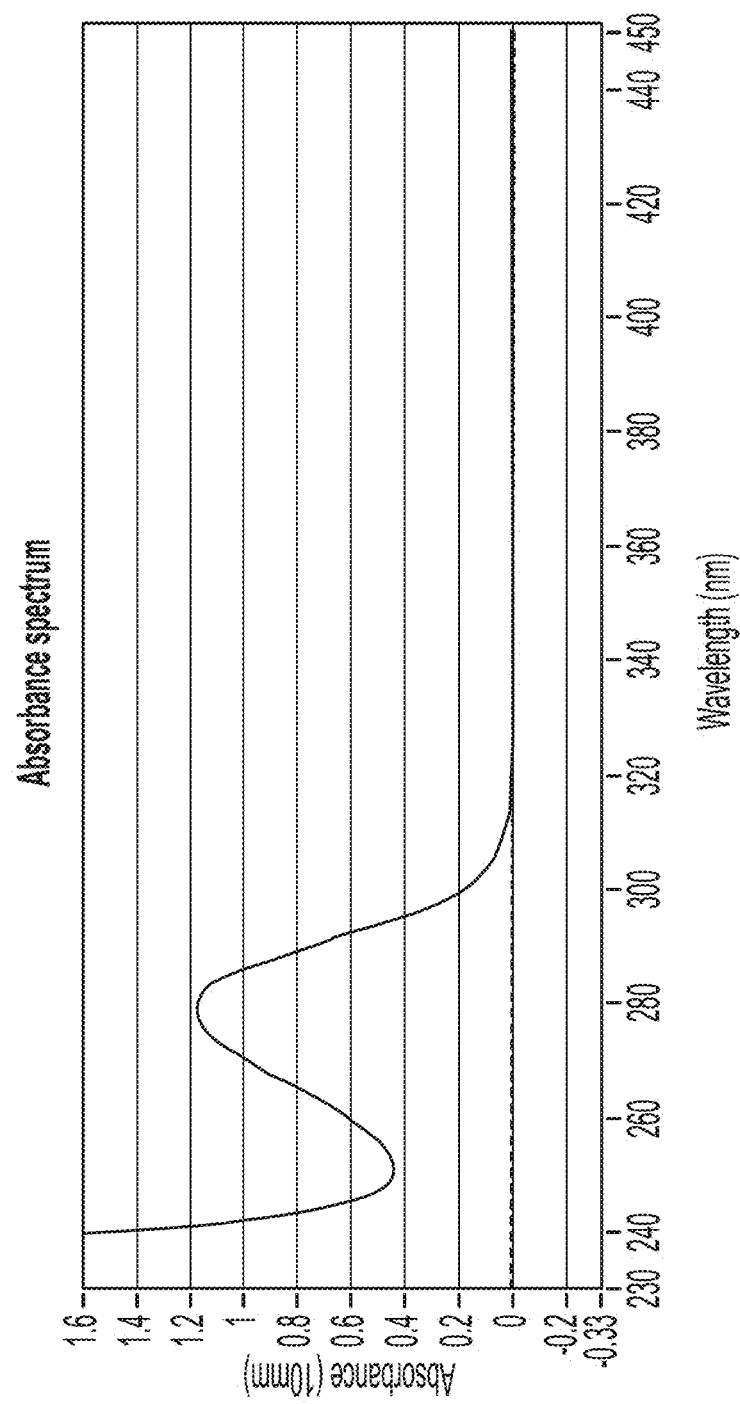
Figure 13:
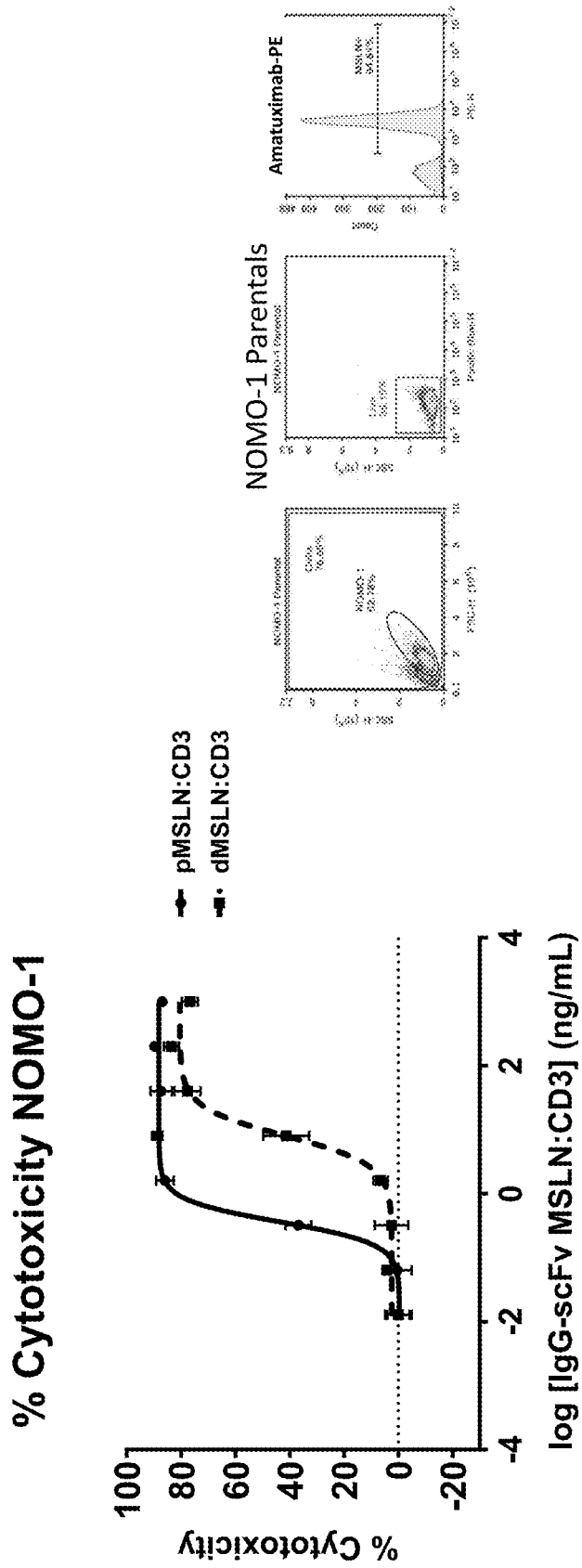

FIG. 13 illustrates the results of a cytotoxicity assay comparing the cytotoxic potency of the IgG-scFv molecule having the structure of FIG. 3A (pMSLN:CD3) and anti-MSLN antigen-binding domains derived from the 1A12 anti-MSLN antibody and humanized OKT3 antigen-binding domains in the scFv portion of the molecule, relative to the same molecule comprising anti-MSLN antigen-binding domains derived from amatuximab (dMSLN:CD3). As shown, the IgG-scFv molecule with binding domain derived from the 1A12 antibody is much more potent relative to the amatuximab version of the molecule even though amatuximab has higher affinity for MSLN.

Figure 14:
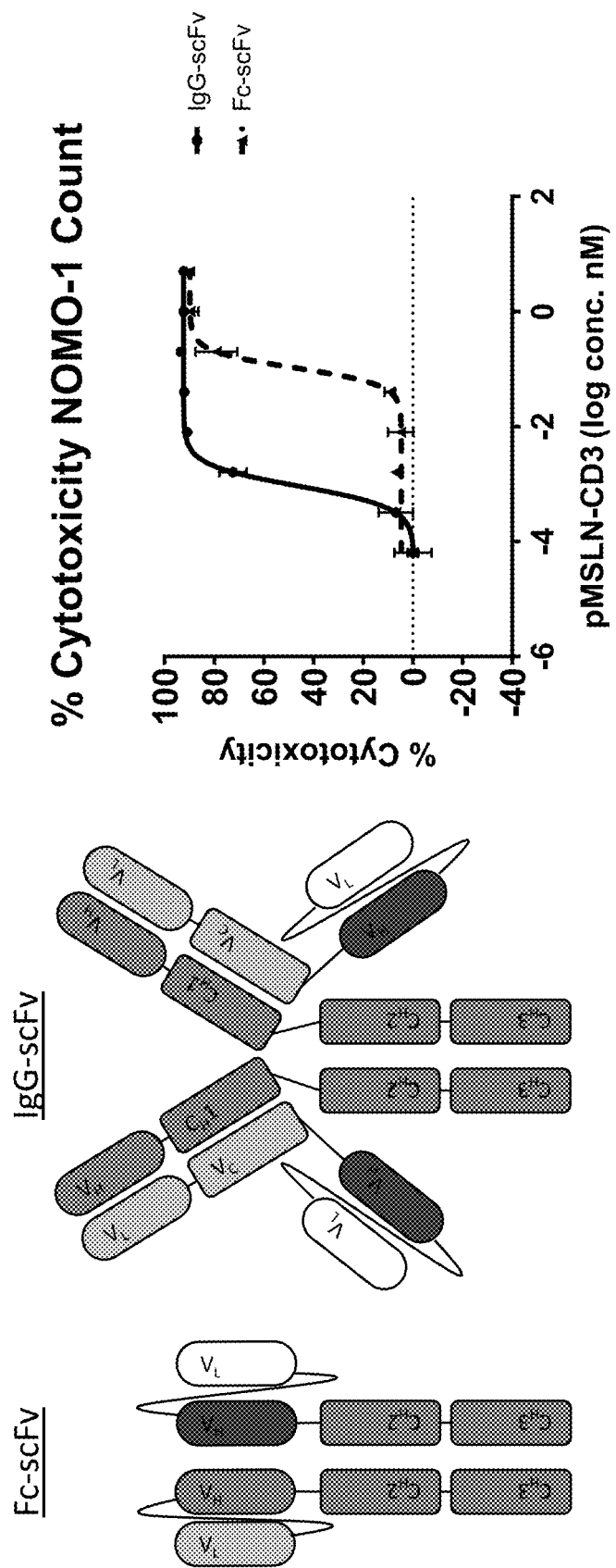

FIG. 14 illustrates the results of a T cell-mediated cytotoxicity comparison between bispecific molecules having the structures of FIGS. 3A and 3B.

Figure 15:
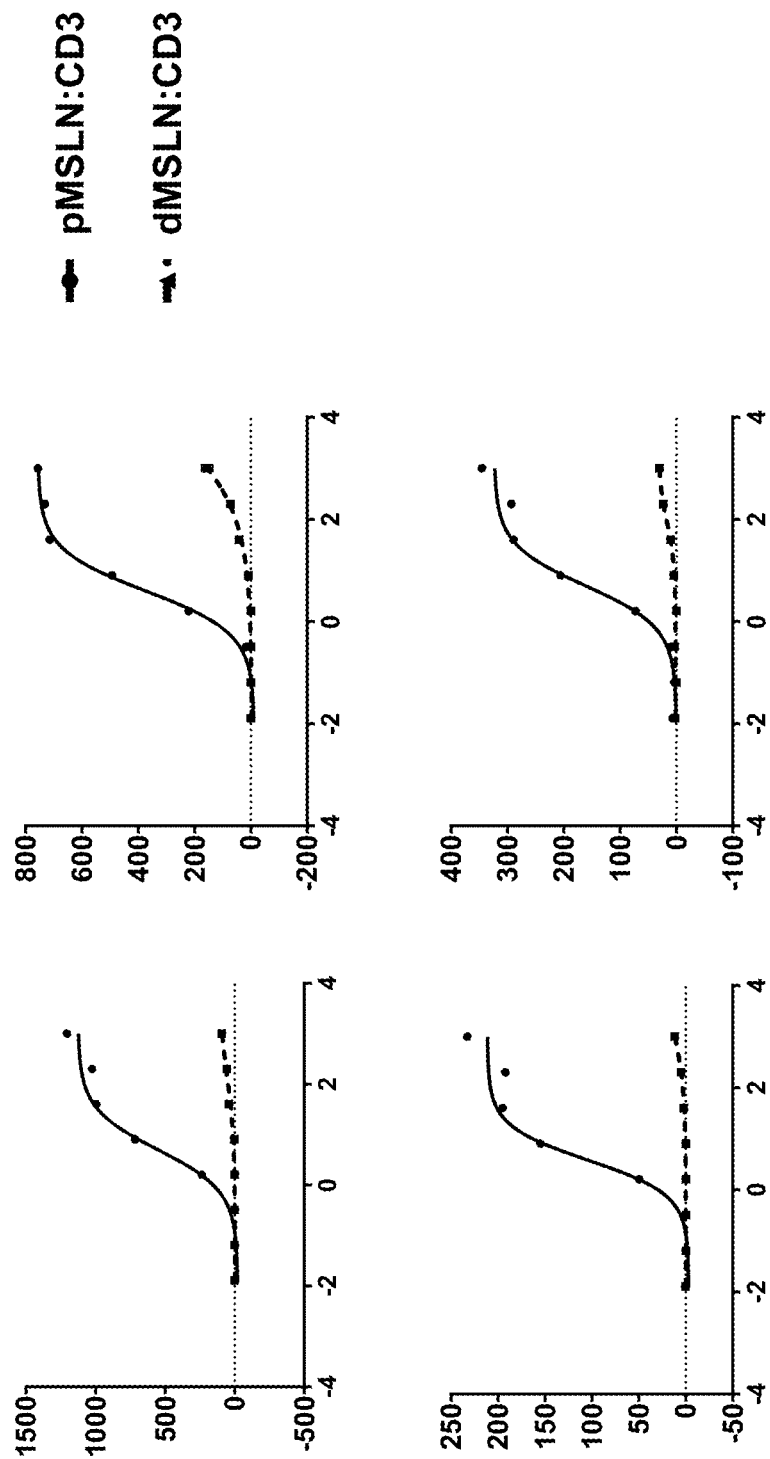
Figure 15:
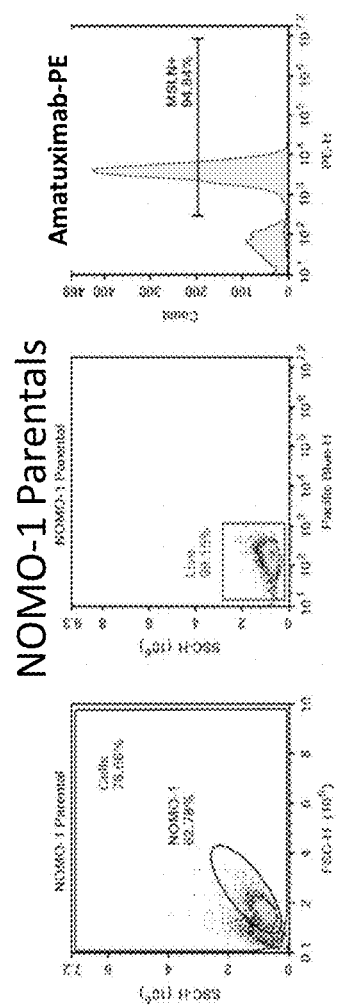

FIG. 15 illustrates dose dependent cytokine concentrations produced from the two IgG-scFv molecules discussed above in connection with FIG. 13, which confirms much more potent T cell activation with the IgG-scFv molecule with the anti-MSLN binding domains derived from the 1A12 antibody relative to the version of the molecule with antigen-binding domains derived from amatuximab.

Figure 16:
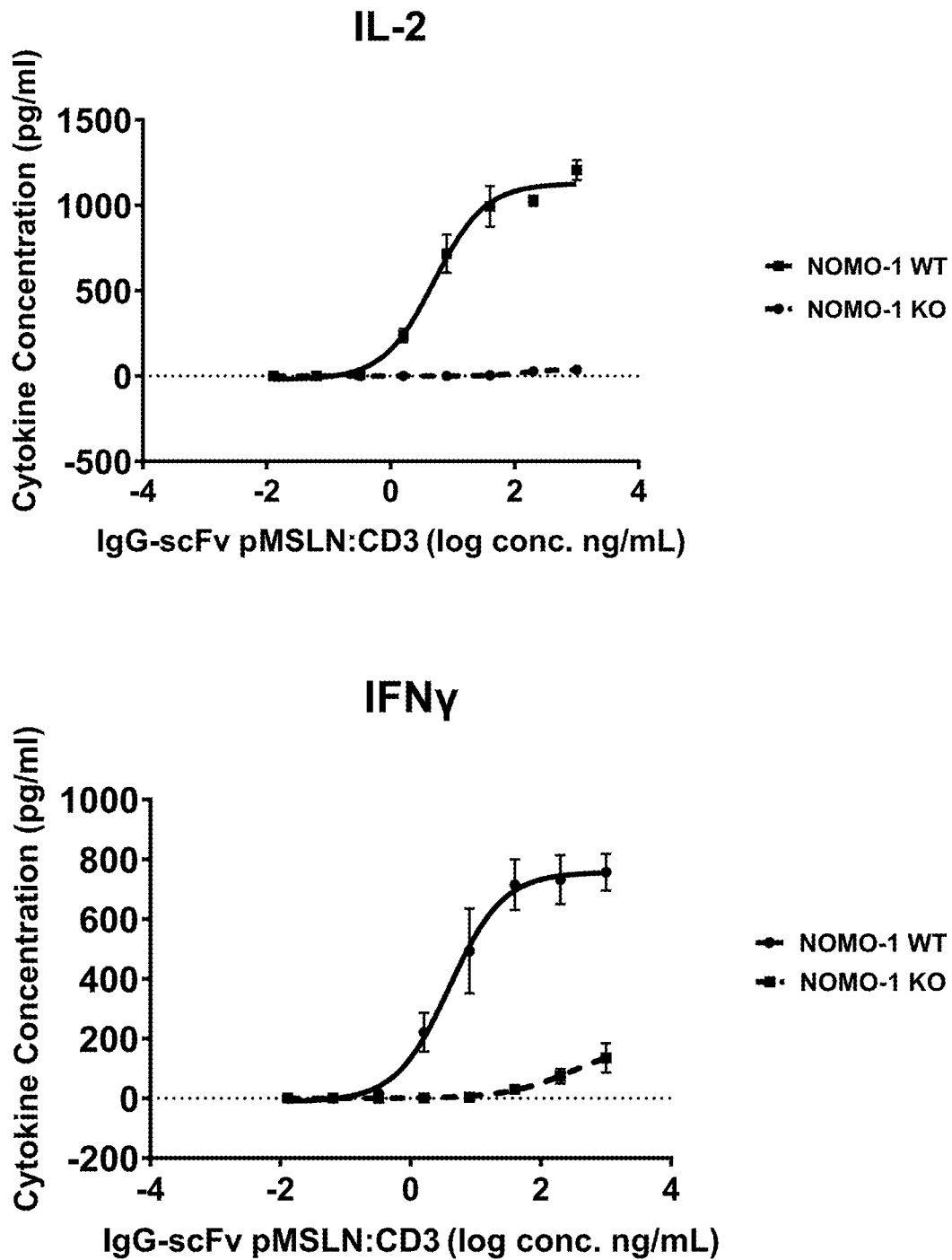

FIG. 16 illustrates cytokine production from the IgG-scFv molecule with the anti-MSLN binding domains derived from the 1A12 antibody in connection with both wild-type and MSLN knock-out NOMO-1 cell lines. As shown, cytokine production (and T cell activation) is reduced or eliminated in the absence of MSLN-expressing cells.

Figure 17A:
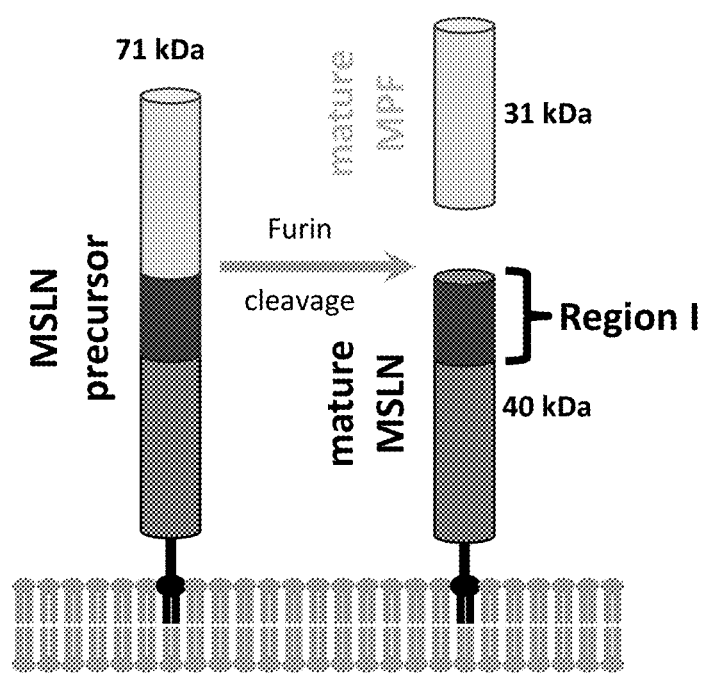

FIG. 17A illustrates physiologic processing of MSLN, as shown in FIG. 5A.

Figure 17B:
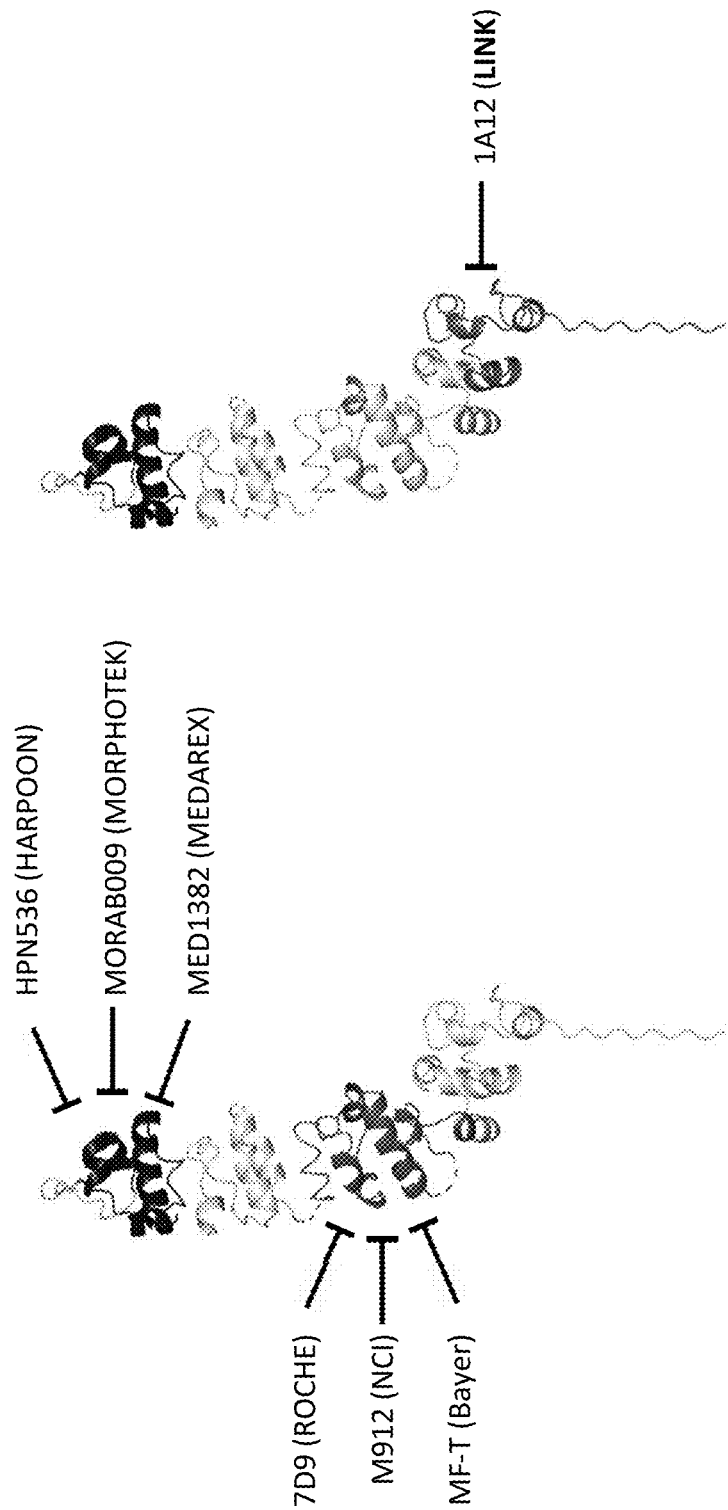

FIG. 17B illustrates MSLN epitopes recognized by various other antibodies as depicted.

FIGS. 18A, 18B, 18C, 18D, 19A, 19B, 19C, 19D, 20A, 20B, 20C and 20D depict MSLN epitope mapping data of the amatuximab antibody (FIGS. 18A, 18B, 18C and 18D), a fully human mAb against MSLN (M912) (FIGS. 19A, 19B, 19C and 19D), and the IgG-scFv molecule having the structure of FIG. 3A (pMSLN:CD3) (FIGS. 20A, 20B, 20C and 20D). Binding kinetics of the antibodies to various epitopes was assessed by surface plasmon resonance spectroscopy.

Figure 19A:
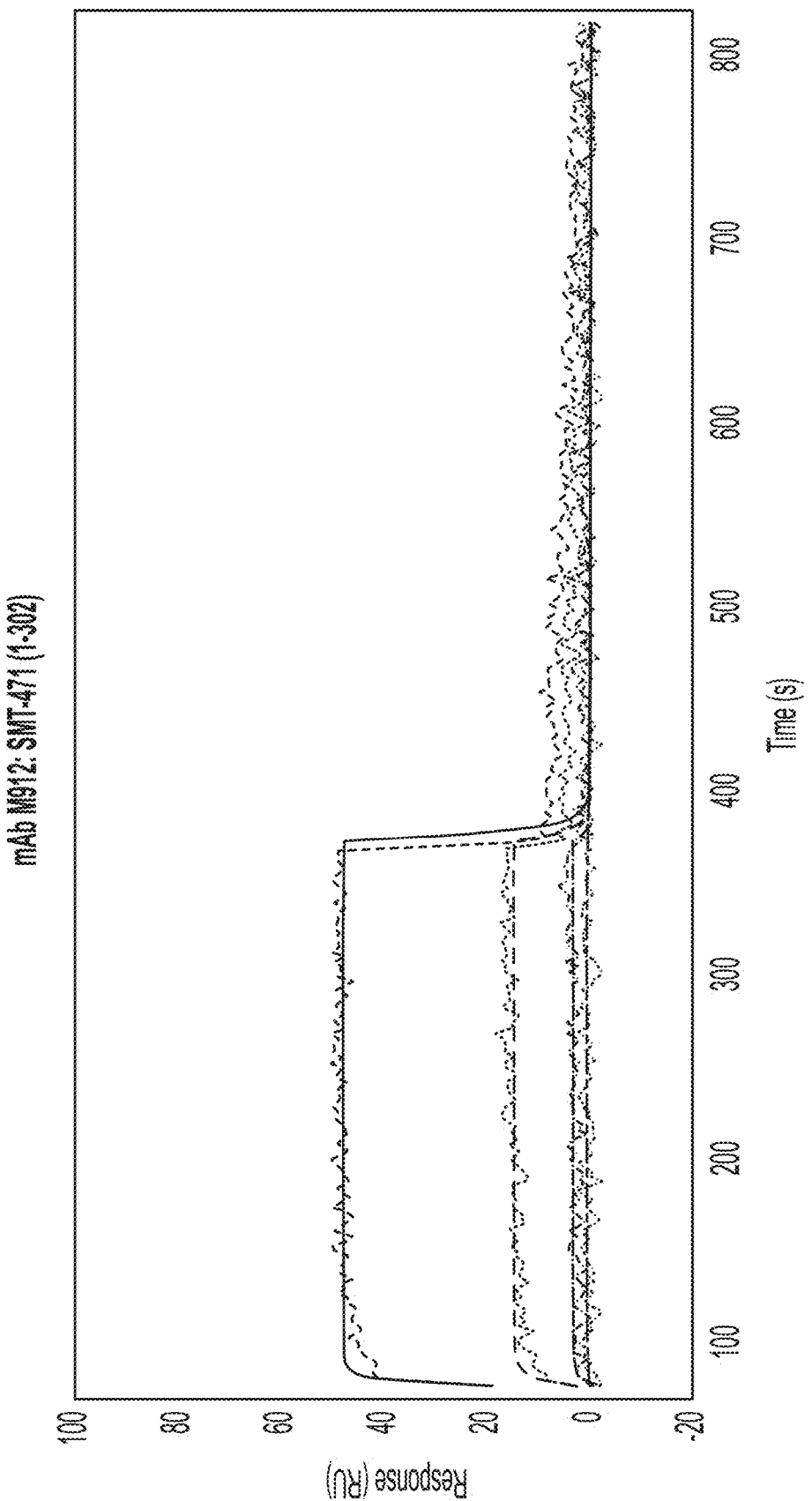
Figure 19B:
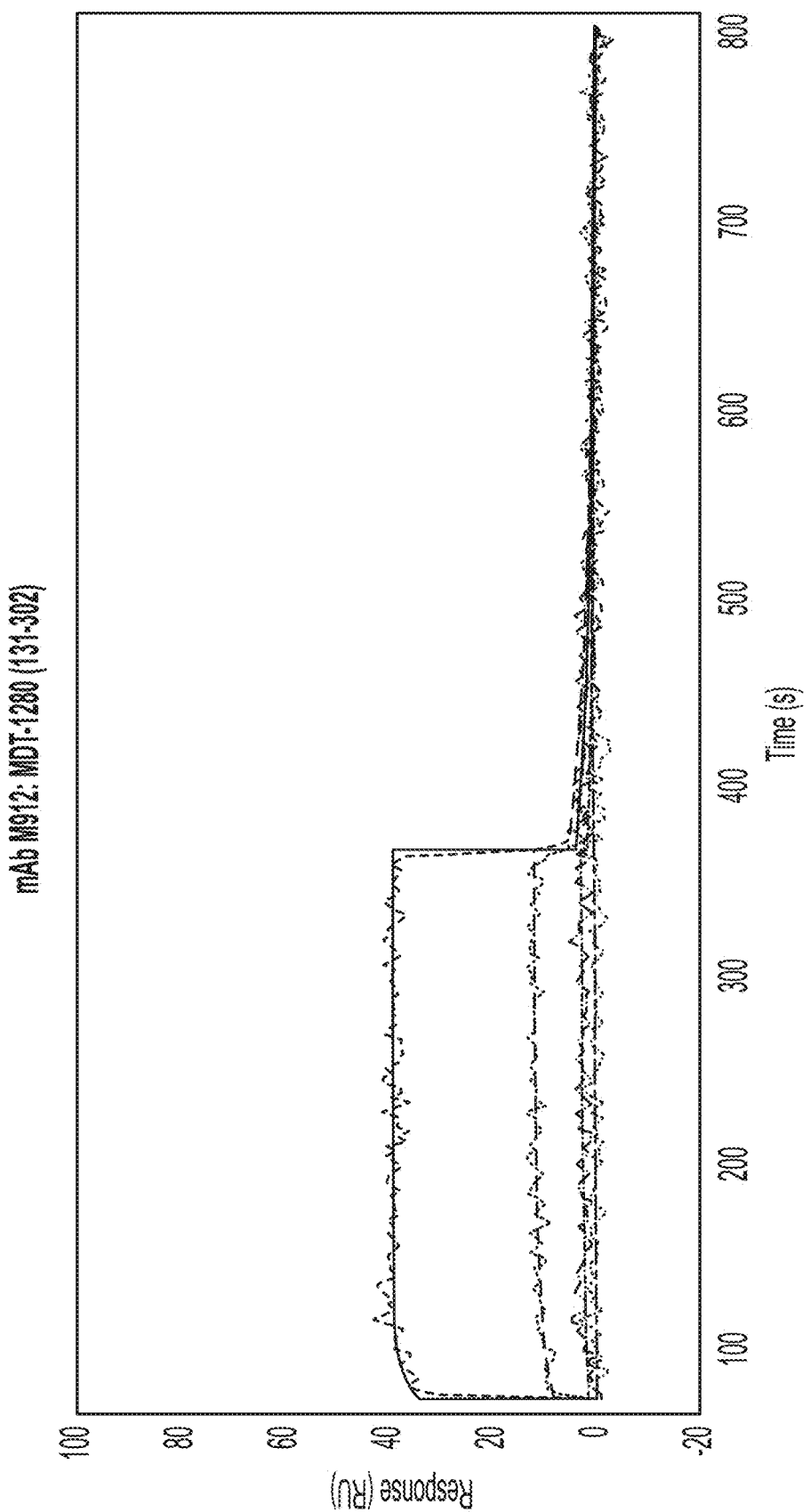
Figure 19C:
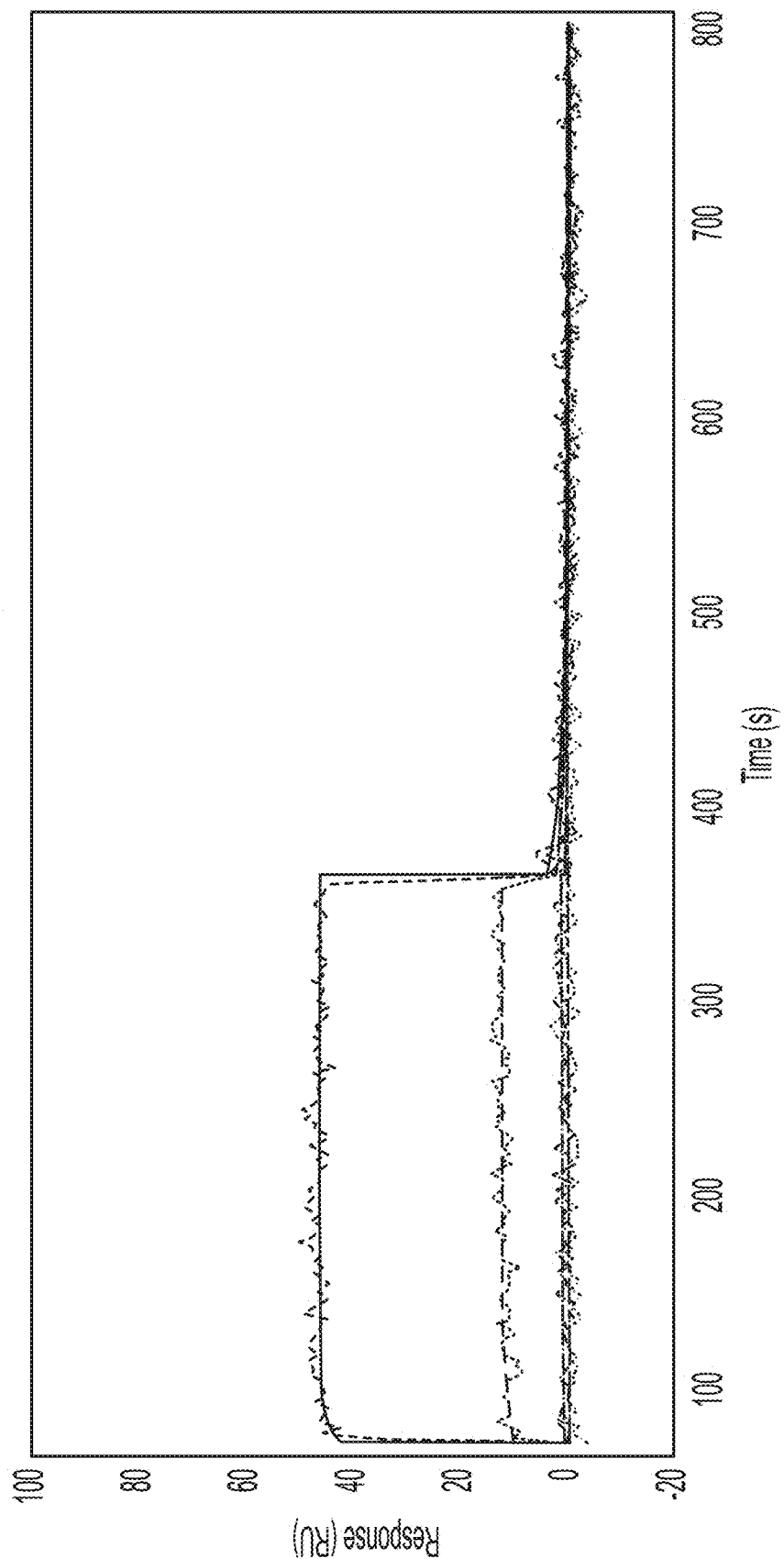
Figure 19D:
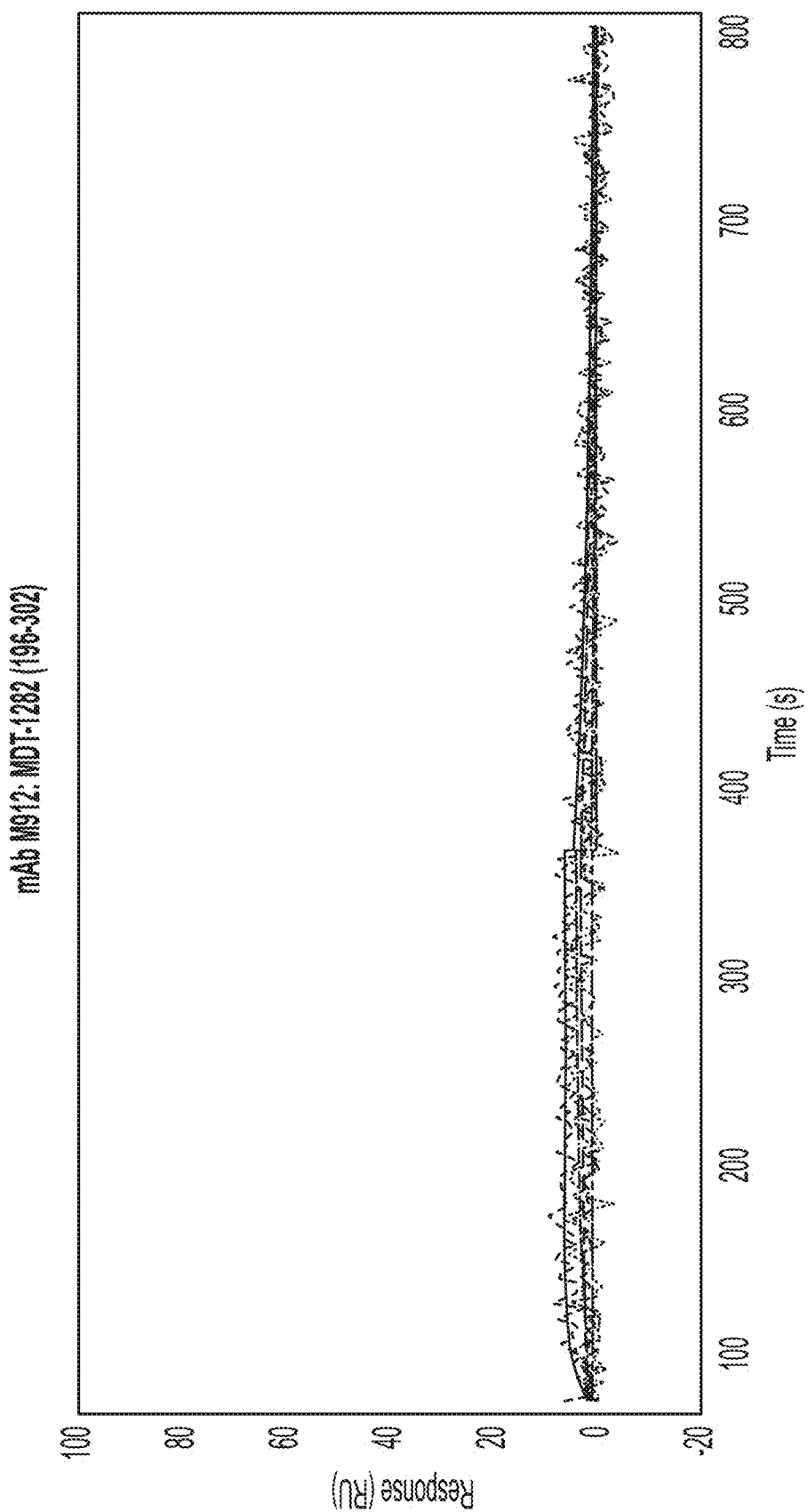
Figure 20A:
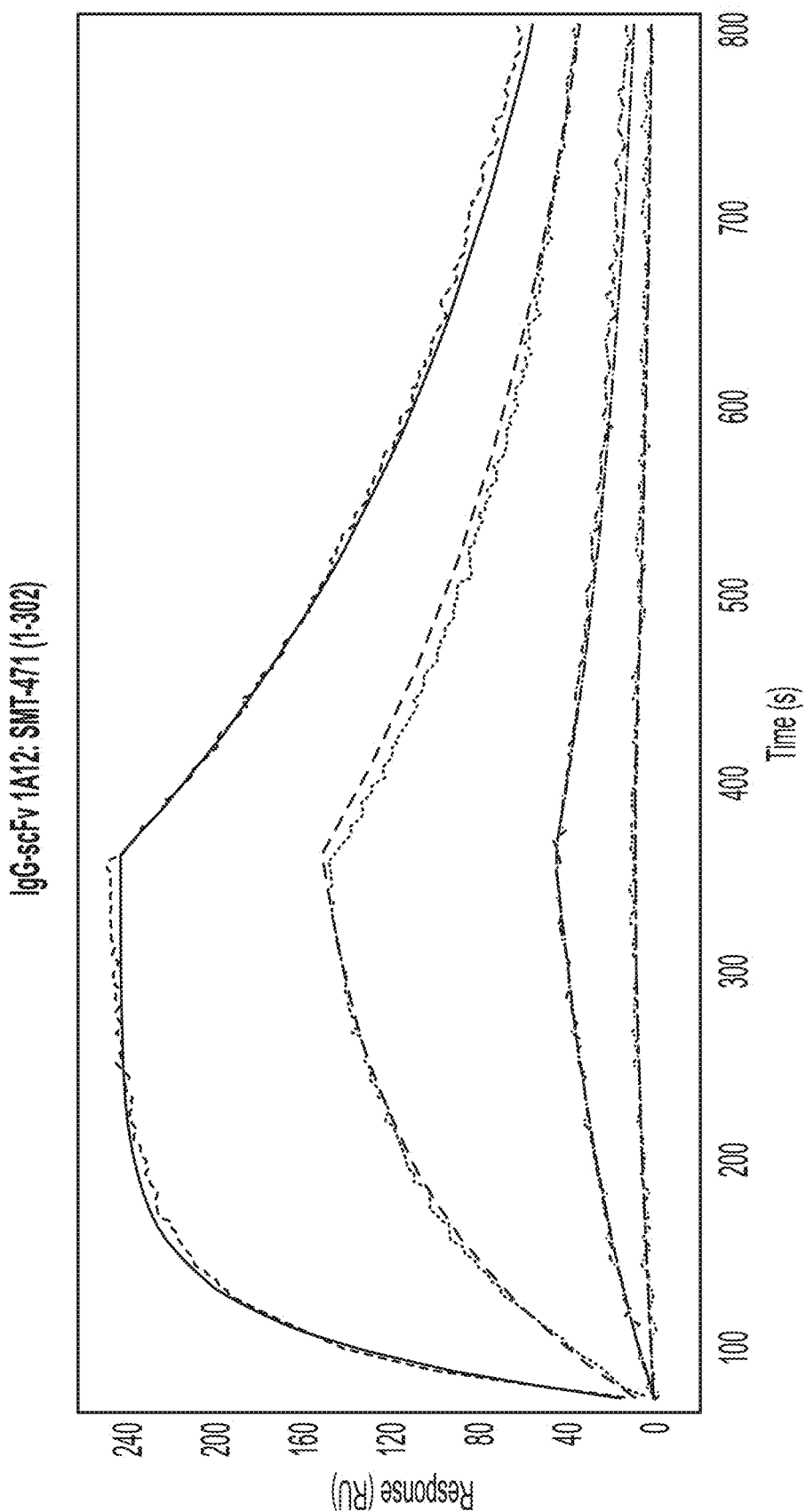
Figure 20B:
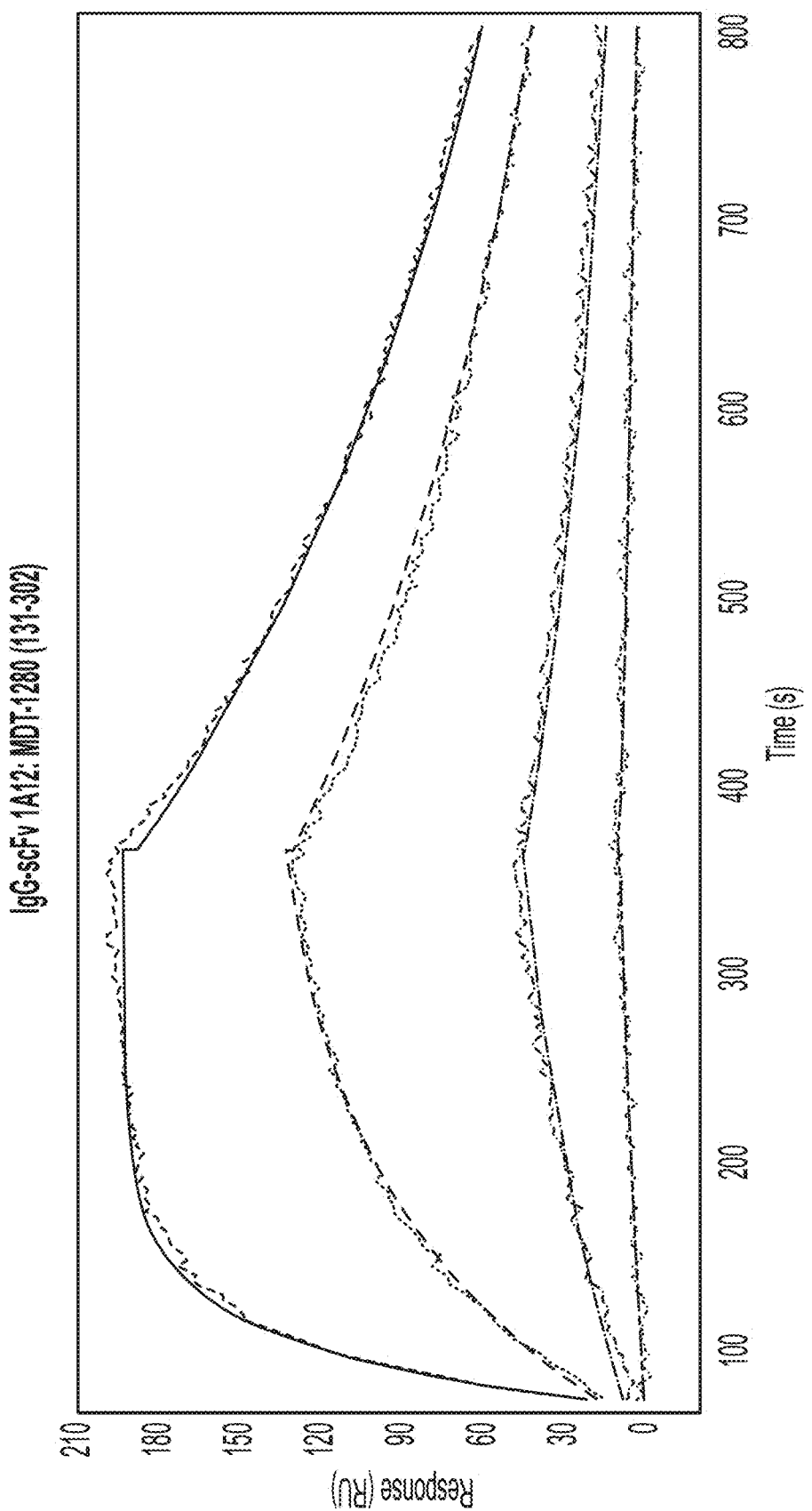
Figure 20C:
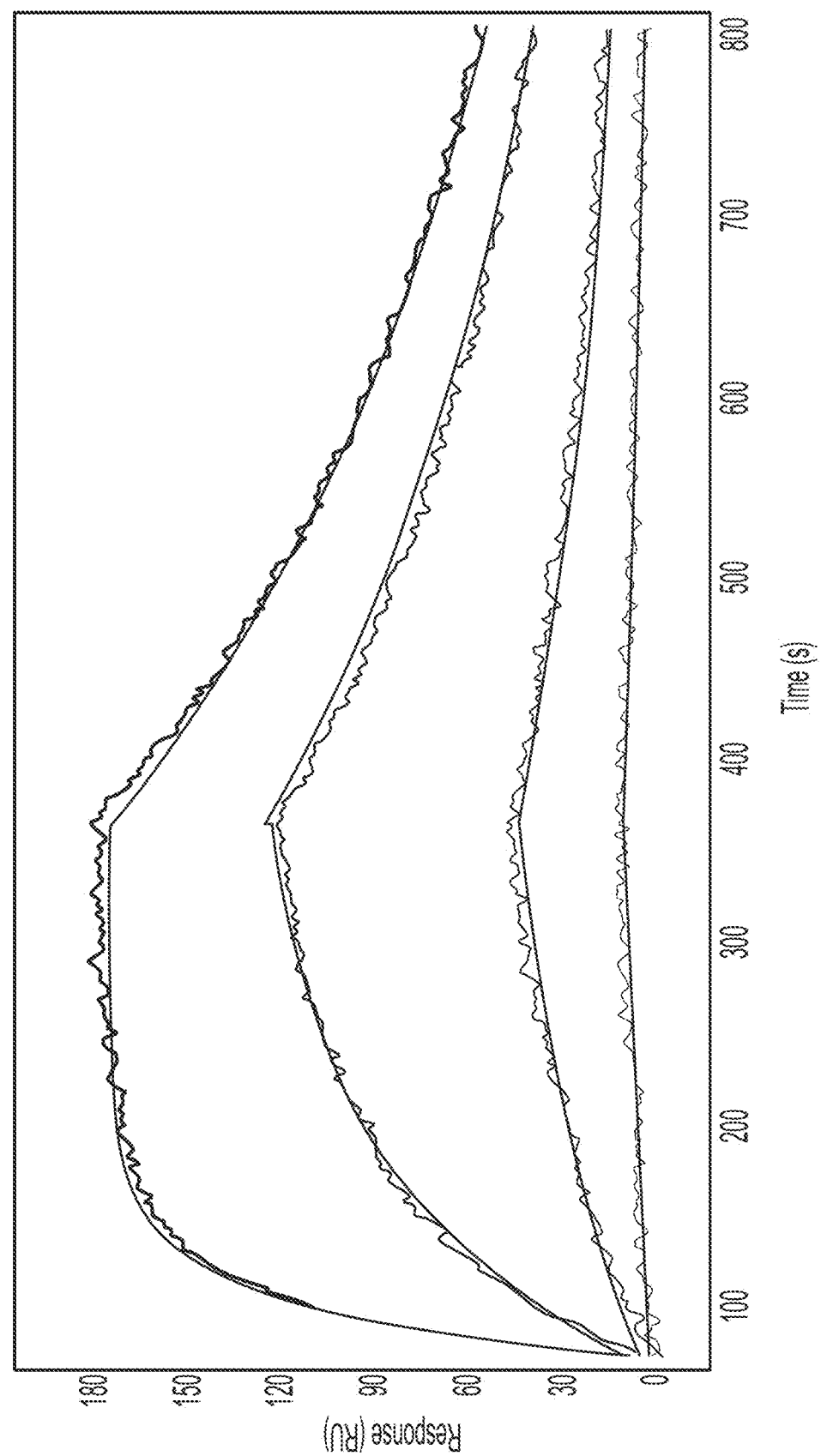
Figure 20D:
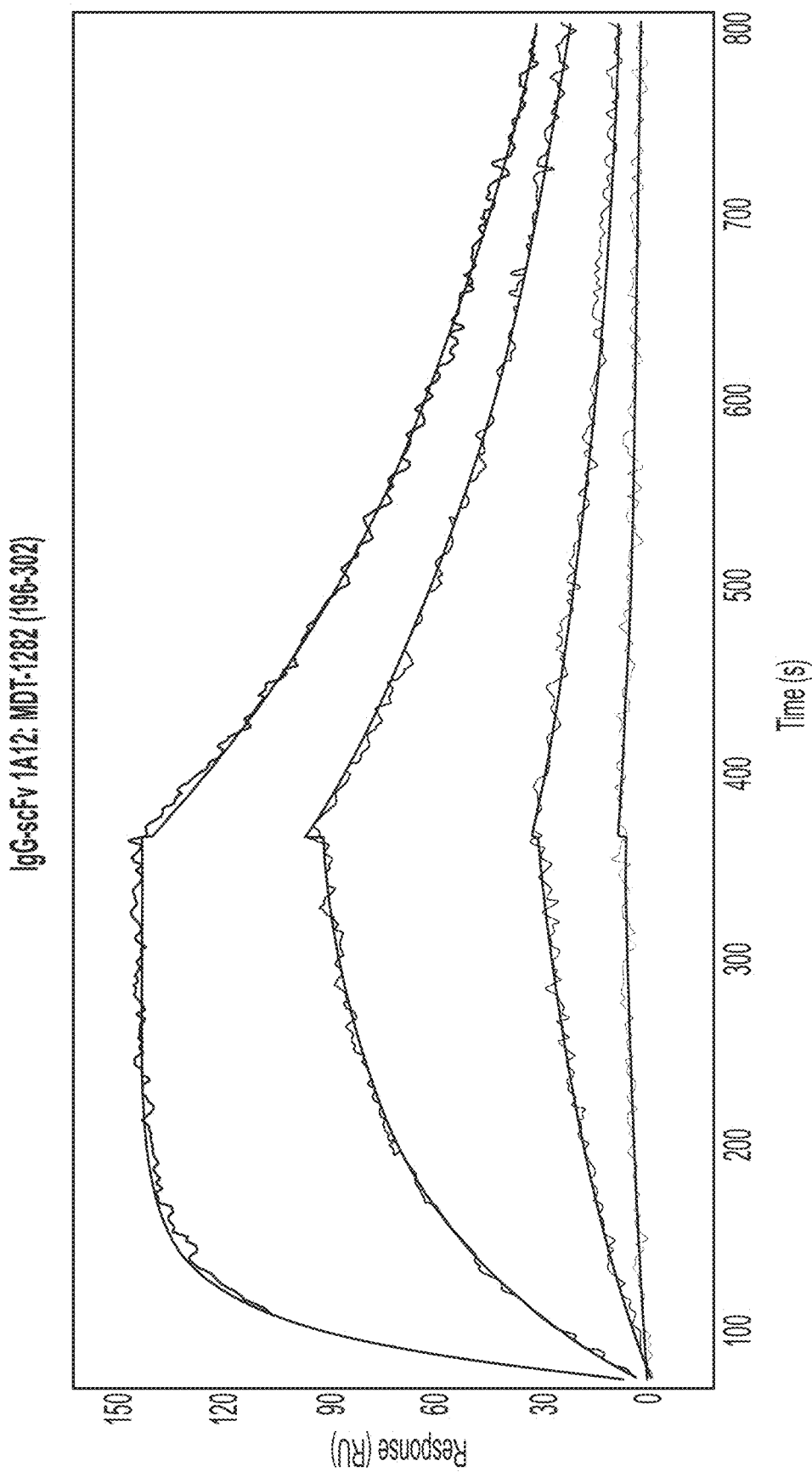
Figure 21:
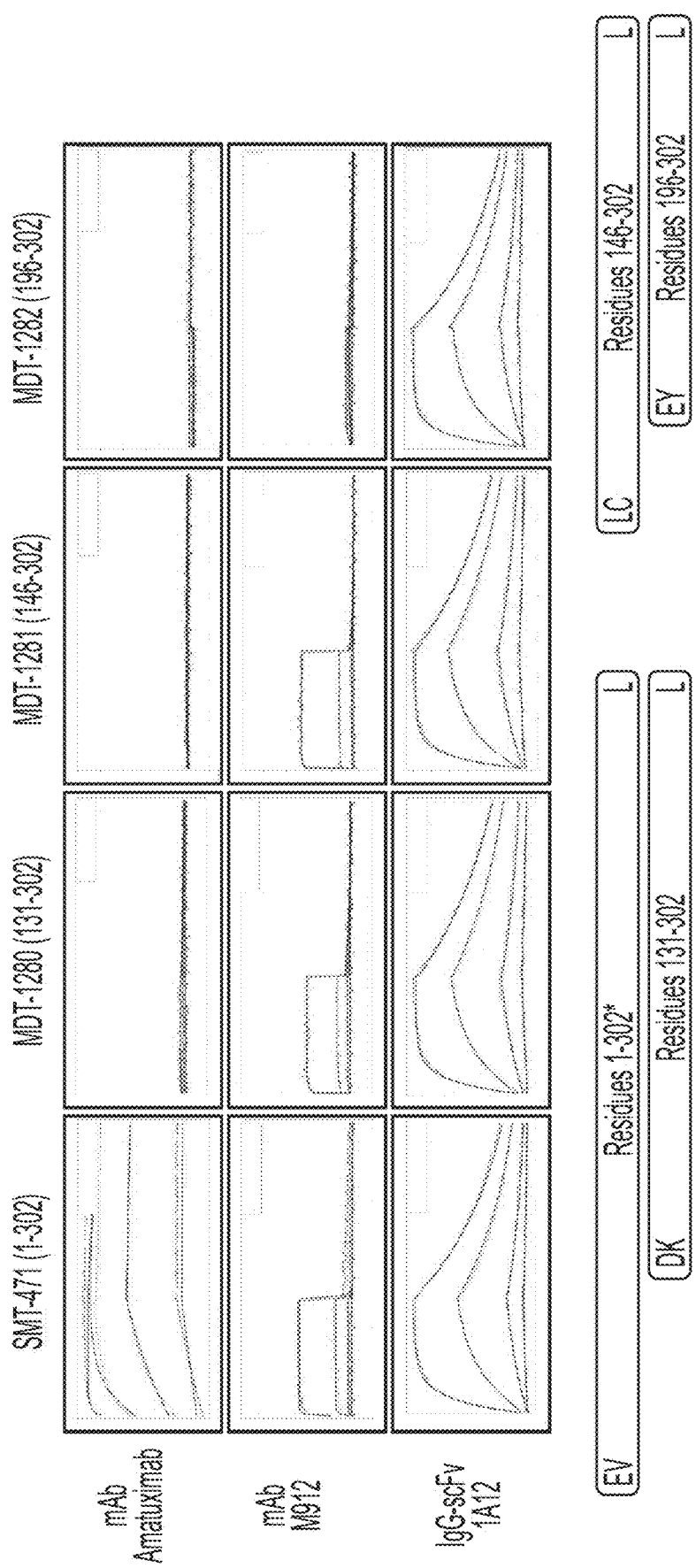

FIG. 21 depicts all of the data of FIGS. 18A, 18B, 18C, 18D, 19A, 19B, 19C, 19D, 20A, 20B, 20C and 20D.

Figure 22:
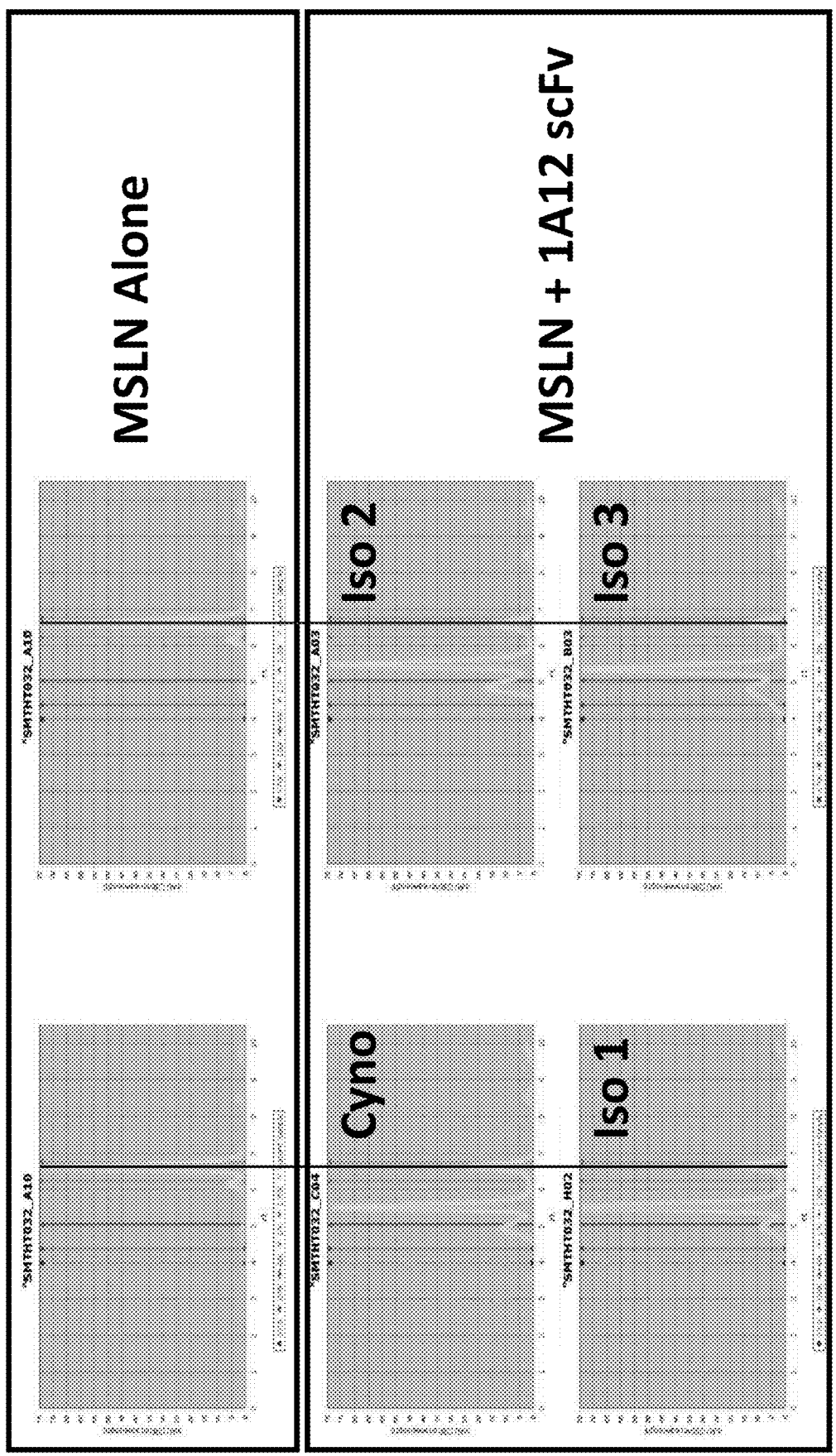

FIG. 22 illustrates size exclusion chromatography (SEC) analysis of pull-down experiments using various human isoforms (Iso 1, Iso 2, Iso 3) and the cynomolgus monkey form of MSLN with an scFV derived from the 1A12 sequence. The scFV binds to all three human isoforms of MSLN and cross-reacts with cynomolgus MSLN epitope.

Figure 23:
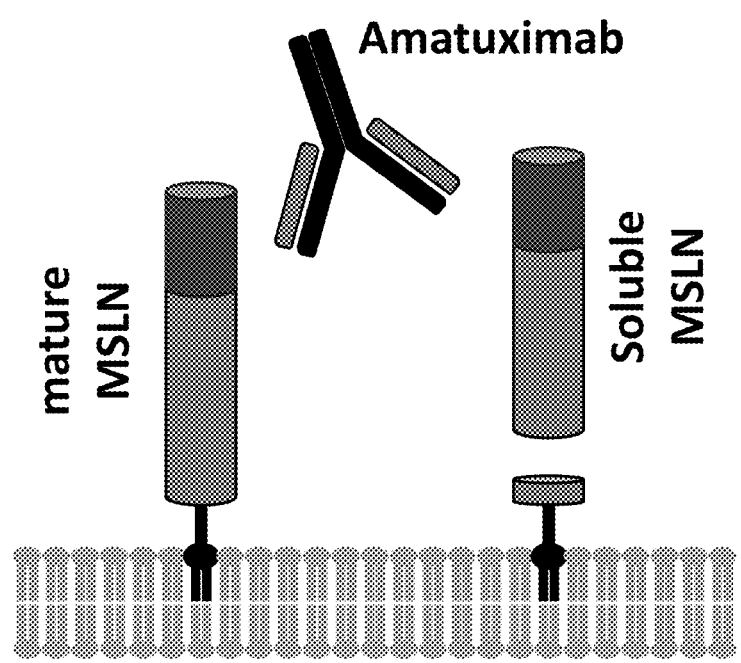

FIG. 23 schematically illustrates that antibodies like amatuximab, which bind to membrane distal epitopes with high affinity, will also bind to soluble mesothelin-related proteins (SMRPs) with high affinity.

Figure 24B:
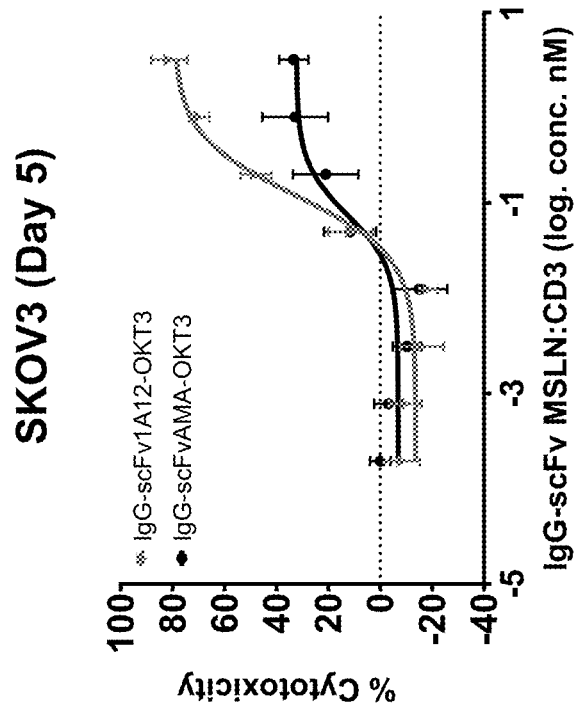
Figure 24A:
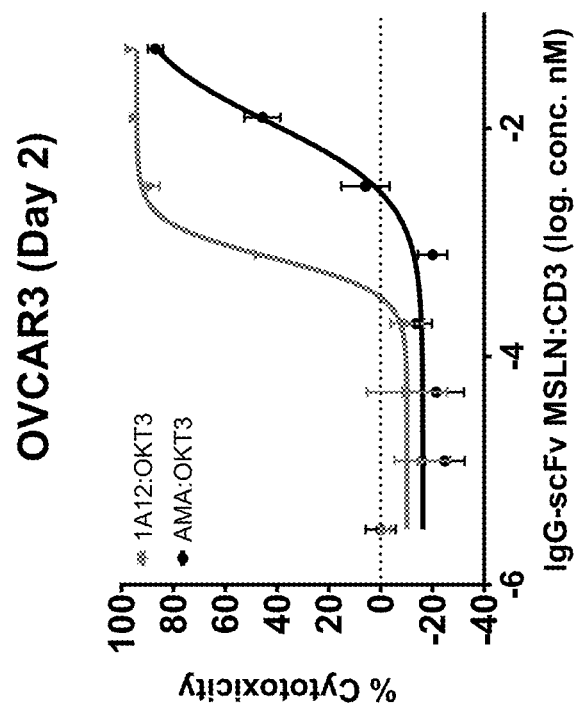

FIGS. 24A and 24B illustrate the results of a cytotoxicity assay comparing the cytotoxic potency of the IgG-scFv molecule having the structure of FIG. 3A (pMSLN:CD3) and anti-MSLN antigen-binding domains derived from the 1A12 anti-MSLN antibody and humanized OKT3 antigen-binding domains in the scFv portion of the molecule, relative to the same molecule comprising anti-MSLN antigen-binding domains derived from amatuximab (dMSLN:CD3). As shown, the IgG-scFv molecule with binding domain derived from the 1A12 antibody is much more potent relative to the amatuximab version of the molecule even though amatuximab has higher affinity for MSLN. MSLN-expressing cells used for the cytoxicity assays were OVCAR3 (FIG. 24A) and SKOV3 (FIG. 24B).

Figure 25B:
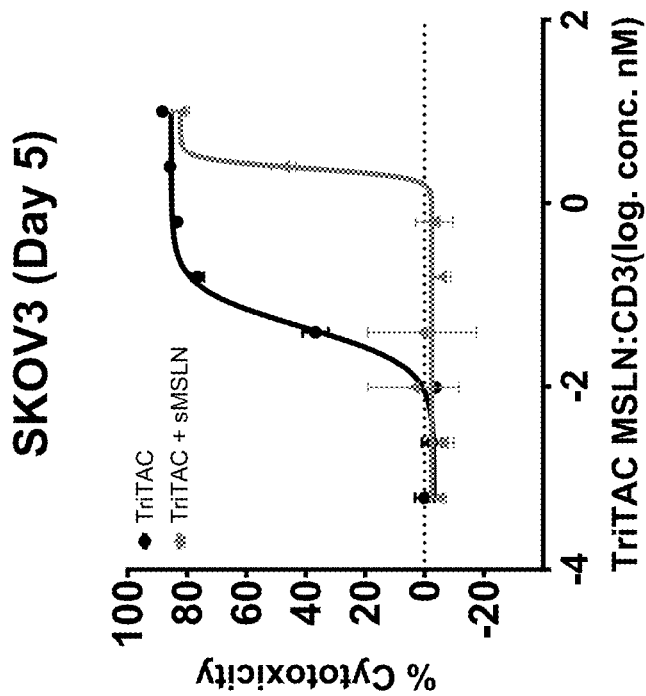
Figure 25A:
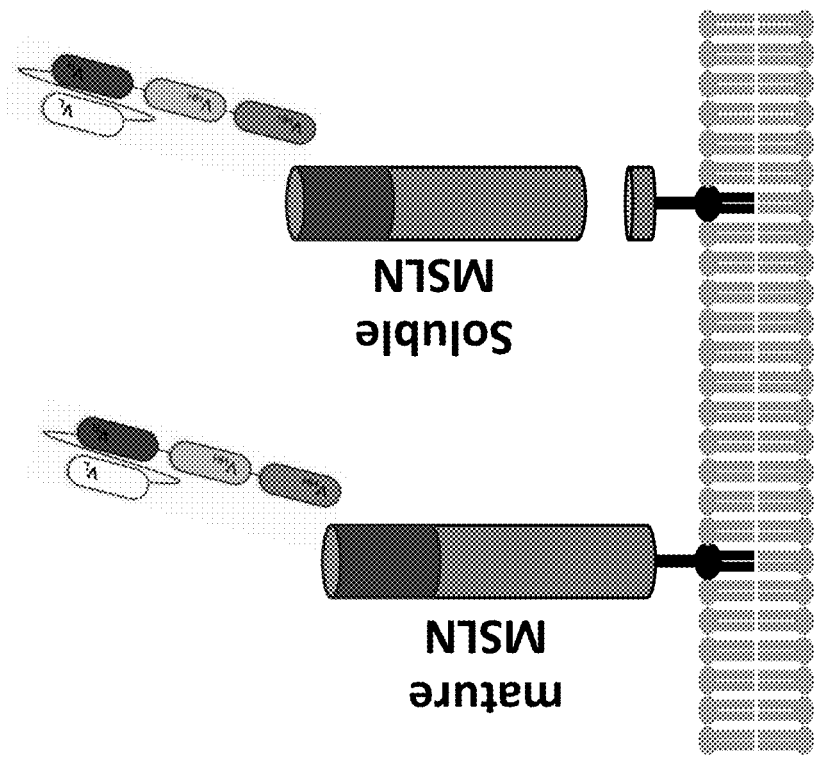

FIGS. 25A and 25B illustrate results of a cytotoxicity assay (FIG. 25B) comparing cytoxic potency of a MSLN:CD3 TriTAC molecule (FIG. 25A) in the presence and absence of soluble mesothelin. As illustratively depicted in FIG. 25A, the TriTAC molecule binds to soluble mesothelin with the same affinity as cell-surface mesothelin which makes it susceptible to a mesothelin antigen sink (FIG. 25B), which is a hallmark of mesothelin-expressing cancers.

Figure 26A:
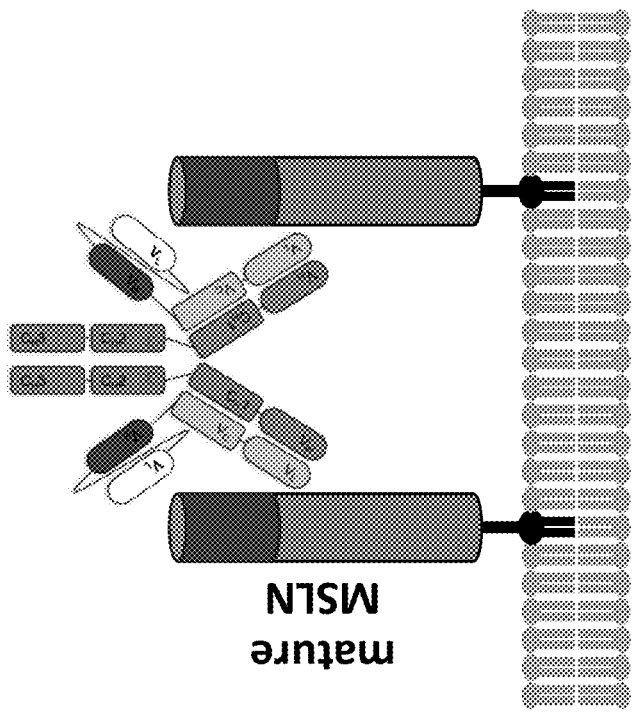
Figure 26B:
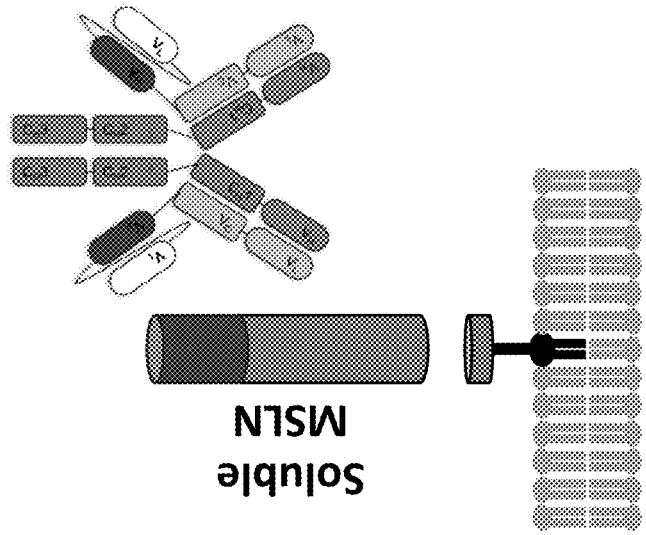
Figure 26C:
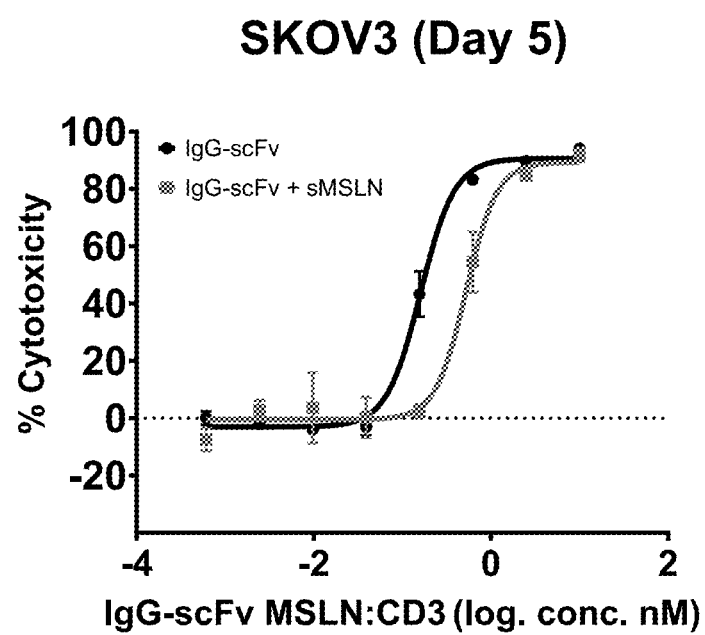

FIGS. 26A, 26B and 26C illustrate results of a cytotoxicity assay (FIG. 26C) comparing the cytotoxic potency of the IgG-scFv molecule having the structure of FIG. 3A (pMSLN:CD3) in the presence and absence of soluble mesothelin. As illustratively shown, the IgG-scFv molecule binds with high avidity to cell-surface MSLN (FIG. 26A) and low affinity to SMRPs (FIG. 26B), which renders the molecule relatively insensitive to high concentrations of soluble mesothelin.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "CD3," as used herein, refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

The expression "MSLN," as used herein, refers to mesothelin. The amino acid sequence of human mesothelin can be found at accession number Q13421 (UniProtKB). MSLN is a cell surface glycoprotein that is highly expressed in pancreatic cancers, ovarian cancers, mesotheliomas, and some other cancer types. Mesothelin is expressed on normal mesothelial cells lining the pleura, pericardium, and peritoneum, but has limited distribution on normal tissues.

As used herein, "an antibody that binds MSLN" or an "anti-MSLN antibody" includes antibodies and antigen-binding fragments thereof that specifically recognize MSLN.

The term "antigen-binding molecule" includes antibodies and antigen-binding fragments of antibodies, including, e.g., bispecific antibodies and bispecific molecules.

The term "antibody", as used herein, means any antigen-binding molecule or molecular complex comprising six complementarity determining regions (CDRs) that specifically bind to or interact with a particular antigen (e.g., MSLN or CD3). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-MSLN antibody or anti-T cell antigen (e.g., CD3) antibody (or antigen-binding portion thereof) may be identical to the human germline sequences, or may be naturally or artificially modified. An amino acid consensus sequence may be defined based on a side-by-side analysis of two or more CDRs or variable regions.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (Vii) $V_H$-$C_L$; (Viii) $V_L$-$C_H1$; (ix) $V_L$-$C_H2$; (X) $V_L$-$C_H3$; (xi) $V_L$-$C_H1$-$C_H2$; (XII) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antigen-binding molecule formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-MSLN monospecific antibodies or anti-MSLN×anti-T cell antigen (TCA) (e.g., CD3) bispecific antigen-binding molecules of the invention are human antibodies or antigen-binding molecules. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind MSLN. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth herein.

The anti-MSLN or anti-MSLN×anti-TCA (e.g., CD3) antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-MSLN or anti-MSLN×anti-TCA (e.g., CD3) antibodies comprising variants of any of the HCVR, LCVR, and/or CDR amino acid sequences disclosed herein having one or more conservative substitutions. For example, the present invention includes anti-MSLN or anti-MSLN×anti-TCA (e.g., CD3) antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Anti-MSLN Antibodies and Antigen-Binding Fragments Thereof

The present invention includes antibodies that bind human mesothelin, and antigen-binding fragments thereof. In various embodiments, the antibody or antigen-binding fragment is a fully human antibody or antigen-binding fragment. In various embodiments, the anti-MSLN antibodies and antigen-binding fragments bind an epitope of human MSLN within the membrane-proximal half of the mature protein. In some embodiments, the anti-MSLN antibodies and antigen-binding fragments bind to an epitope in SEQ ID NO: 50. In some embodiments, the anti-MSLN antibodies and antigen-binding fragments bind to an epitope on the mature human mesothelin protein that is destroyed by a cleavage event that forms soluble mesothelin. Anti-MSLN antibodies that bind to an epitope that is destroyed by a cleavage event that forms soluble mesothelin will not bind to the soluble form of mesothelin.

In certain embodiments, the antibody or antigen-binding fragment thereof competes for binding to human MSLN with a reference antibody comprising an HCVR/LCVR amino acid sequence pair selected from the group consisting of SEQ ID NOs: 1/2, 9/10, 17/18, 25/26, 33/34, 41/42, 51/52, and 53/54.

In certain embodiments, the antibody or antigen-binding fragment thereof binds to the same epitope on human MSLN as a reference antibody comprising an HCVR/LCVR amino acid sequence pair selected from the group consisting of SEQ ID NOs: 1/2, 9/10, 17/18, 25/26, 33/34, 41/42, 51/52, and 53/54.

In certain embodiments, the antibody or antigen-binding fragment comprises: (a) the complementarity determining regions (CDRs) of a heavy chain variable region (HCVR) having an amino acid sequence selected from the group consisting of SEQ ID NOs: 1, 9, 17, 25, 33, 41, 51, and 53; and (b) the CDRs of a light chain variable region (LCVR) having an amino acid sequence selected from the group consisting of SEQ ID NOs: 2, 10, 18, 26, 34, 42, 52, and 54.

In certain embodiments, the antibody or antigen-binding fragment comprises the heavy and light chain CDRs of a HCVR/LCVR amino acid sequence pair selected from the group consisting of SEQ ID NOs: 1/2, 9/10, 17/18, 25/26, 33/34, 41/42, 51/52, and 53/54.

In certain embodiments, the antibody or antigen-binding fragment comprises HCDR1-HCDR2-HCDR3-LCDR1-LCDR2-LCDR3 domains, respectively, selected from the group consisting of SEQ ID NOs: 3-4-5-6-7-8, 11-12-13-14-15-16, 19-20-21-22-23-24, 27-28-29-30-31-32, 35-36-37-38-39-40, 43-44-45-46-47-48, 55-56-57-58-59-60, and 61-62-63-64-65-66.

In certain embodiments, the antibody or antigen-binding fragment comprises HCDR1-HCDR2-HCDR3-LCDR1-LCDR2-LCDR3 domains, respectively, selected from the group consisting of SEQ ID NOs: 3-4-5-6-7-8, 11-12-13-14-15-16, 19-20-21-22-23-24, 27-28-29-30-31-32, 35-36-37-38-39-40, 43-44-45-46-47-48, 55-56-57-58-59-60, and 61-62-63-64-65-66, and (a) a HCVR with at least 90%, 95%, or 99% sequence identity to an amino acid sequence selected from the group consisting of SEQ ID NOs: 1, 9, 17, 25, 33, 41, 51, and 53, and (b) a LCVR with at least 90%, 95%, or 99% sequence identity to an amino acid sequence selected from the group consisting of SEQ ID NOs: 2, 10, 18, 26, 34, 42, 52 and 54.

In certain embodiments, the antibody or antigen-binding fragment comprises a HCVR/LCVR amino acid sequence pair selected from the group consisting of: SEQ ID NOs: 1/2, 9/10, 17/18, 25/26, 33/34, 41/42, 51/52, and 53/54.

In certain embodiments, the present invention provides an antibody or antigen-binding fragment hereof that is a human, humanized or a chimeric antibody. The antibody or antigen-binding fragment thereof can for instance be an IgG1 or an IgG4 antibody, such as e.g., a human IgG1 or an IgG4 antibody. The constant regions of those antibodies might correspond to wild-type constant regions, or to constant regions into which mutations have been introduced.

As discussed in greater detail below, the present invention also provides a multi-specific antigen-binding molecule comprising a first antigen-binding domain that specifically binds to MSLN and a second antigen-binding domain that specifically binds to a second target antigen or epitope, for example a T cell antigen (e.g., CD3).

The present invention further provides a pharmaceutical composition comprising an anti-MSLN antibody or antigen-binding fragment thereof as discussed herein, and a pharmaceutically acceptable carrier or diluent.

The present invention further provides isolated polynucleotide molecules and vectors comprising polynucleotide sequences of the antibodies or antigen-binding fragments thereof as discussed herein. In certain embodiments, the present invention provides an isolated polynucleotide molecule or molecules, and/or a vector comprising one or more polynucleotide sequences that encode a HCVR and/or LCVR of an antibody or antigen-binding molecule as set forth herein. In certain embodiments, the present invention provides a cell expressing the vectors or polynucleotides discussed above or herein.

Preparation of Anti-Mesothelin Antibodies

Anti-MSLN antibodies and antigen-binding fragments can be prepared by any antibody generating technology known in the art. In certain embodiments, one or more of the individual components (e.g., heavy and light chains) of the antibodies or antigen-binding fragments of the invention are derived from chimeric, humanized or fully human antibodies. Methods for making such antibodies are well known in the art. For example, one or more of the heavy and/or light chains of the antibodies or antigen-binding fragments of the present invention can be prepared using TRIANNI™ technology (Trianni, Inc, San Francisco, Calif.). Using TRI-ANNI™ technology (or any other human antibody generating technology), high affinity chimeric antibodies to a particular antigen to human MSLN are initially isolated having a human variable region and a mouse constant region. The antibodies are characterized and selected for desirable characteristics, including affinity, selectivity, epitope, etc. The mouse constant regions are replaced with a desired human constant region to generate fully human antibodies or fully human antigen-binding fragments of the present invention.

Binding Properties of the Anti-MSLN Antibodies and Antigen-Binding Molecules

As used herein, the term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIACORE™ 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, J Immunol Methods. 1997, 201(2):223-31; Geuijen, C A, et al. J Immunol Methods. 2005, 302(1-2):68-77).

Accordingly, the antibody or antigen-binding protein of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody or bispecific antigen-binding molecule of the invention.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing a T cell antigen (e.g., CD3) or tumor-associated antigen (e.g., MSLN), as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

In another embodiment, the $EC_{50}$ value represents the concentration of an antibody of the invention that elicits half-maximal depletion of target cells by T cell cytotoxic activity. Thus, increased cytotoxic activity (e.g. T cell-mediated tumor cell killing) is observed with a decreased E050, or half maximal effective concentration value.

Bispecific Antigen-Binding Molecules

The antibodies or antigen-binding molecules of the present invention may be monospecific, bispecific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. In some embodiments, the antigen-binding molecules of the present invention are bispecific antigen-binding molecules having the structure of FIG. 3A or FIG. 3B. The molecules having the structure of FIG. 3A are both bispecific and bivalent for each of the target antigens (e.g., MSLN and CD3), and are also referred to herein as IgG-scFv molecules. The molecules having the structure of FIG. 3A comprise a conventional monospecific antibody structure in which the antigen-binding domains are specific for MSLN, but also include two scFv domains covalently linked to the N-terminus of the two light chain constant regions, respectively, in which the scFv domains are oriented in a VH-VL orientation (i.e., the VH portion of each of the two scFv domains is covalently linked to the N-terminus of the respective light chain constant region), and which are specific for a T cell antigen (TCA) (e.g., CD3). As discussed in Example 5, bispecific antigen-binding molecules having the structure of FIG. 3A in which the scFv domains are linked in a VH-VL orientation have superior binding affinity relative to the same structure in which the scFv domains are linked in a VL-VH orientation. The molecules having the structure of FIG. 3B are bispecific but monovalent for each of the target antigens (e.g., MSLN and CD3), and are also referred to herein as Fc-scFv molecules. The molecules having the structure of FIG. 3B comprise scFv domains attached, respectively, to the C-terminus of an immunoglobulin Fc domain. The two Fc domains of this molecule associate with one another as in a conventional antibody molecule e.g., via disulfide bonds) to form the bispecific antigen-binding molecule of FIG. 3B. In any of the bispecific molecules discussed herein, including those having the structures of FIGS. 3A and 3B, the anti-cancer or anti-MSLN antigen-binding domain(s) may be derived from the anti-MSLN antibodies discussed herein. For example, the anti-MSLN antigen-binding domains may comprise the CDRs and/or the variable regions of the anti-MSLN antibodies discussed herein. The anti-MSLN monospecific antibodies or anti-MSLN×anti-TCA (e.g., CD3) bispecific antigen-binding molecules of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second or additional binding specificity.

Use of the expression "anti-MSLN antibody" herein is intended to include both monospecific anti-MSLN antibodies as well as bispecific antibodies and bispecific antigen-binding molecules comprising a MSLN-binding arm or antigen-binding domain. Thus, the present invention includes bispecific antibodies or bispecific antigen-binding molecules wherein one arm of an immunoglobulin binds human MSLN, and the other arm of the immunoglobulin is specific for, e.g., a T cell antigen such as CD3.

According to certain exemplary embodiments, the present invention includes bispecific antigen-binding molecules that specifically bind a T cell antigen (e.g., CD3) and MSLN. Such molecules may be referred to herein as, e.g., "anti-MSLN×anti-TCA" or "anti-TCA/anti-MSLN," or "anti-TCA×MSLN" or "TCA×MSLN" bispecific molecules, or other similar terminology (e.g., anti-MSLN/anti-TCA).

The term "MSLN," as used herein, refers to the human MSLN protein unless specified as being from a non-human species (e.g., "mouse MSLN," "monkey MSLN," etc.).

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., MSLN), and the second antigen-binding domain specifically binds a second, distinct antigen (e.g., CD3).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and D\A1-HCDR3; and the CDRs of the second antigen-binding domain may be referred to herein as A2-HCDR1, A2-HCDR2, and A2-HCDR3.

In certain exemplary embodiments, the isolated bispecific antigen binding molecule comprises a first antigen-binding domain(s) that specifically binds MSLN, and which comprises: (a) three heavy chain complementarity determining regions (HCDR1, HCDR2 and HCDR3) contained within a heavy chain variable region (HCVR) comprising the amino acid sequence of any one of SEQ ID NOs: 1, 9, 17, 25, 33, 41, 51, or 53; and (b) three light chain complementarity determining regions (LCDR1, LCDR2 and LCDR3) contained within a light chain variable region (LCVR) comprising the amino acid sequence of any one of SEQ ID NOs: 2, 10, 18, 34, 42, 52, or 54. In some cases, the isolated bispecific antigen binding molecule comprises a first antigen-binding domain(s) comprising the heavy and light chain CDRs of a HCVR/LCVR amino acid sequence pair selected from the group consisting of SEQ ID NOs: 1/2, 9/10, 17/18, 25/26, 33/34, 41/42, 51/52, and 53/54.

In certain exemplary embodiments, the isolated bispecific antigen binding molecule comprises a first antigen-binding domain(s) that specifically binds MSLN, and which comprises HCDR1-HCDR2-HCDR3-LCDR1-LCDR2-LCDR3 domains, respectively, selected from the group consisting of SEQ ID NOs: 3-4-5-6-7-8, 11-12-13-14-15-16, 19-20-21-22-23-24, 27-28-29-30-31-32, 35-36-37-38-39-40, 43-44-45-46-47-48, 55-56-57-58-59-60, and 61-62-63-64-65-66.

In certain exemplary embodiments, the isolated bispecific antigen binding molecule comprises a first antigen-binding domain(s) that specifically binds MSLN, and which comprises HCDR1-HCDR2-HCDR3-LCDR1-LCDR2-LCDR3 domains, respectively, selected from the group consisting of SEQ ID NOs: 3-4-5-6-7-8, 11-12-13-14-15-16, 19-20-21-22-23-24, 27-28-29-30-31-32, 35-36-37-38-39-40, 43-44-45-46-47-48, 55-56-57-58-59-60, and 61-62-63-64-65-66, and (a) a HCVR with at least 90%, 95%, or 99% sequence identity to an amino acid sequence selected from the group consisting of SEQ ID NOs: 1, 9, 17, 25, 33, 41, 51, and 53, and (b) a LCVR with at least 90%, 95%, or 99% sequence identity to an amino acid sequence selected from the group consisting of SEQ ID NOs: 2, 10, 18, 26, 34, 42, 52 and 54.

In certain exemplary embodiments, the isolated bispecific antigen binding molecule comprises a first antigen-binding domain(s) that specifically binds MSLN, and which comprises a HCVR/LCVR amino acid sequence pair selected from the group consisting of: SEQ ID NOs: 1/2, 9/10, 17/18, 25/26, 33/34, 41/42, 51/52, and 53/54.

In certain exemplary embodiments, the first antigen-binding domain(s) of the isolated bispecific antigen binding molecule competes for binding to human MSLN with a reference antibody comprising an HCVR/LCVR amino acid sequence pair selected from the group consisting of SEQ ID NOs: 1/2, 9/10, 17/18, 25/26, 33/34, 41/42, 51/52, and 53/54.

In certain exemplary embodiments, the first antigen-binding domain(s) of the isolated bispecific antigen binding molecule binds to the same epitope on human MSLN as a reference antibody comprising an HCVR/LCVR amino acid sequence pair selected from the group consisting of SEQ ID NOs: 1/2, 9/10, 17/18, 25/26, 33/34, 41/42, 51/52, and 53/54.

In certain exemplary embodiments, the isolated bispecific antigen binding molecule competes for binding to a human T cell antigen (e.g., CD3), or binds to the same epitope on a human T cell antigen (e.g., CD3) as a reference antibody.

The bispecific antigen-binding molecules discussed above or herein may be bispecific antibodies. In some cases, the bispecific antibody or bispecific antigen-binding molecule comprises a human IgG heavy chain constant region. In some cases, the human IgG heavy chain constant region is isotype IgG1. In some cases, the human IgG heavy chain constant region is isotype IgG4. In various embodiments, the bispecific antibody or bispecific antigen-binding molecule comprises a constant region (e.g., Fc domain) modification that reduces Fcγ receptor binding relative to a wild-type constant region of the same isotype. In some embodiments, the modification is a modification to a glycosylation site.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats).

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. Chimeric Fc domains having these general structural arrangements, and variants thereof, can have altered Fc receptor binding, which in turn affects Fc effector function.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

pH-Dependent Binding

The present invention includes anti-MSLN antibodies, and anti-MSLN×anti-TCA (e.g., CD3) bispecific antigen-binding molecules, with pH-dependent binding characteristics. For example, an anti-MSLN antibody of the present invention may exhibit reduced binding to MSLN at acidic pH as compared to neutral pH. Alternatively, anti-MSLN antibodies of the invention may exhibit enhanced binding to MSLN at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to MSLN at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-MSLN antibodies, and anti-MSLN×anti-TCA (e.g., CD3) bispecific antigen-binding molecules, are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-MSLN antibodies, and anti-MSLN×anti-TCA (e.g., CD3) bispecific antigen-binding molecules, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules The present invention includes antibodies and antigen-binding fragments thereof that bind human MSLN with high affinity (e.g., nanomolar or sub-nanomolar $K_D$ values).

According to certain embodiments, the present invention includes antibodies and antigen-binding fragments of antibodies that bind human MSLN (e.g., at 25° C.) with a $K_D$ of less than about 150 nM as measured by surface plasmon resonance. In certain embodiments, the antibodies or antigen-binding fragments of the present invention bind MSLN with a $K_D$ of less than about 100 nM, less than about 80 nM, less than about 75 nM, or less than about 70 nM.

The present invention also includes antibodies and antigen-binding fragments thereof which bind specifically to human cell lines which express endogenous MSLN, as determined by a FACS binding assay as set forth in the examples or a substantially similar assay.

The present invention includes antibodies and antigen-binding fragments thereof that bind a human T cell antigen (e.g., CD3) with high affinity. The present invention also includes antibodies and antigen-binding fragments thereof that bind a human T cell antigen (e.g., CD3) with medium or low affinity, depending on the therapeutic context and particular targeting properties that are desired.

The present invention includes bispecific antigen-binding molecules (e.g., bispecific antibodies) which are capable of simultaneously binding to a human T cell antigen (e.g., CD3) and human MSLN. The extent to which a bispecific antigen-binding molecule binds cells that express a human T cell antigen (e.g., CD3) and/or MSLN can be assessed by fluorescence activated cell sorting (FACS), as illustrated in the examples herein.

For example, the present invention includes antibodies, antigen-binding fragments, and bispecific antibodies thereof which specifically bind human T cell lines which express an antigen such as CD3 but do not express MSLN (e.g., Jurkat), and/or MSLN-expressing cells.

The present invention includes antibodies, antigen-binding fragments, and bispecific antigen-binding molecules that bind a human T cell antigen (e.g., CD3) and induce T cell activation.

The present invention includes anti-MSLN×anti-TCA (e.g., CD3) bispecific antigen-binding molecules which are capable of depleting or reducing tumor antigen-expressing cells in a subject. For example, according to certain embodiments, anti-MSLN×anti-TCA (e.g., CD3) bispecific antigen-binding molecules are provided, wherein a single administration, or multiple administrations, of the bispecific antigen-binding molecule to a subject causes a reduction in the number of MSLN-expressing cells in the subject (e.g., tumor growth in the subject is suppressed or inhibited).

Epitope Mapping and Related Technologies

The epitope on the T cell antigen (e.g., CD3) and/or MSLN to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a TCA or MSLN protein. Alternatively, the epitope may consist of a plurality of non-contiguous amino acids (or amino acid sequences) of the TCA or MSLN. The antibodies and molecules of the invention may, e.g., interact with amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present invention further includes anti-MSLN antibodies that bind to the same epitope as any of the specific exemplary antibodies described herein (e.g. antibodies comprising any of the amino acid sequences as set forth herein). Likewise, the present invention also includes anti-MSLN antibodies that compete for binding to MSLN with any of the specific exemplary antibodies described herein (e.g. antibodies comprising any of the amino acid sequences as set forth herein).

The present invention also includes bispecific antigen-binding molecules comprising a first antigen-binding domain that specifically binds human MSLN, and a second antigen binding domain that specifically binds a human T cell antigen (e.g., CD3), wherein the first antigen-binding domain competes for binding to MSLN with any of the specific exemplary MSLN-specific antigen-binding domains described herein, and/or wherein the second antigen-binding domain competes for binding to the TCA (e.g., CD3) with any of the specific exemplary TCA-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on MSLN (or CD3) as a reference bispecific antigen-binding molecule of the present invention, the reference bispecific molecule is first allowed to bind to a MSLN protein (or CD3 protein). Next, the ability of a test antibody to bind to the MSLN (or CD3) molecule is assessed. If the test antibody is able to bind to MSLN (or CD3) following saturation binding with the reference bispecific antigen-binding molecule, it can be concluded that the test antibody binds to a different epitope of MSLN (or CD3) than the reference bispecific antigen-binding molecule. On the other hand, if the test antibody is not able to bind to the MSLN (or CD3) molecule following saturation binding with the reference bispecific antigen-binding molecule, then the test antibody may bind to the same epitope of MSLN (or CD3) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, BIACORE™, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a MSLN protein (or CD3 protein) under saturating conditions followed by assessment of binding of the test antibody to the MSLN (or CD3) molecule. In a second orientation, the test antibody is allowed to bind to a MSLN (or CD3) molecule under saturating conditions followed by assessment of binding of the reference antigen-binding molecule to the MSLN (or CD3) molecule. If, in both orientations, only the first (saturating) antigen-binding molecule is capable of binding to the MSLN (or CD3) molecule, then it is concluded that the test antibody and the reference antigen-binding molecule compete for binding to MSLN (or CD3). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and MSLN), can be appropriately arranged relative to one another to produce a bispecific antigen-binding molecule of the present invention using routine methods. (A discussion of exemplary bispecific formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using TRIANNI™ technology (Trianni, Inc, San Francisco, Calif.). Using TRIANNI™ technology (or any other human antibody generating technology), high affinity chimeric antibodies to a particular antigen (e.g., CD3 or MSLN) are initially isolated having a human variable region and a mouse constant region. The antibodies are characterized and selected for desirable characteristics, including affinity, selectivity, epitope, etc. The mouse constant regions are replaced with a desired human constant region to generate fully human antibodies or fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bioequivalents

The present invention encompasses antigen-binding molecules having amino acid sequences that vary from those of the exemplary molecules disclosed herein but that retain the ability to bind to a human T cell antigen (e.g., CD3) and/or MSLN. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary antibodies and bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary antibodies or bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to a human T cell antigen (e.g., CD3) but not to the TCA from other species. Also provided are antigen-binding molecules which bind to human MSLN, but not to MSLN from other species. The present invention also includes antigen-binding molecules that bind to a human T cell antigen (e.g., CD3) and to the TCA from one or more non-human species; and/or antigen-binding molecules that bind to human MSLN and to MSLN from one or more non-human species.

According to certain exemplary embodiments of the invention, antigen-binding molecules are provided which bind to a human T cell antigen (e.g., CD3) and/or human MSLN and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee TCA and/or MSLN. For example, in particular exemplary embodiments of the present invention bispecific antigen-binding molecules are provided comprising a first antigen-binding domain that binds human MSLN and cynomolgus MSLN, and a second antigen-binding domain that specifically binds a human T cell antigen (e.g., CD3), or bispecific antigen-binding molecules comprising a first antigen-binding domain that binds human MSLN and cynomolgus MSLN, and a second antigen-binding domain that specifically binds a human T cell antigen (e.g., CD3).

Therapeutic Formulation and Administration

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When an antibody or a bispecific antigen-binding molecule of the present invention is used for therapeutic purposes in an adult patient, it may be advantageous to intravenously administer the antibody or bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering an antibody or bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or molecule, or its salt, described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-MSLN antibody or antigen-binding fragment thereof, or a bispecific antigen-binding molecule that specifically binds a human T cell antigen (e.g., CD3) and MSLN. The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein), or who otherwise would benefit from an inhibition or reduction in MSLN activity or a depletion of MSLN+ cells (e.g., ovarian cancer cells).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-MSLN antibodies or the anti-MSLN×anti-TCA bispecific antigen-binding molecules of the present invention may be used for the treatment, prevention and/or amelioration of any disease or disorder associated with or mediated by MSLN expression or activity or the proliferation of MSLN+ cells. The mechanism of action by which the therapeutic methods of the invention are achieved include killing of the cells expressing MSLN in the presence of effector cells, for example, by CDC, apoptosis, ADCC, phagocytosis, or by a combination of two or more of these mechanisms. Cells expressing MSLN which can be inhibited or killed using the bispecific antigen-binding molecules of the invention include, for example, ovarian cancer cells.

The antigen-binding molecules of the present invention may be used to treat a disease or disorder associates with MSLN expression including, e.g., a MSLN-positive cancer. According to certain embodiments of the present invention, the anti-MSLN antibodies or anti-MSLN×anti-TCA bispecific antigen-binding molecules are useful for treating a patient afflicted with a MSLN+cancer. According to other related embodiments of the invention, methods are provided comprising administering an anti-MSLN antibody or an anti-MSLN×anti-TCA bispecific antigen-binding molecule as disclosed herein to a patient who is afflicted with a MSLN+cancer. Analytic/diagnostic methods known in the art, such as tumor scanning, etc., may be used to ascertain whether a patient harbors a MSLN+cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with MSLN expression comprising administering one or more of the anti-MSLN or bispecific antigen-binding molecules described elsewhere herein to a subject after the subject has been determined to have, e.g., a MSLN+cancer. For example, the present invention includes methods for treating a MSLN+cancer comprising administering an anti-MSLN antibody or an anti-MSLN×anti-TCA bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other immunotherapy or chemotherapy.

Combination Therapies and Formulations

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an anti-tumor agent (e.g., chemotherapeutic agents). In certain embodiments the second therapeutic agent is a regimen comprising radiotherapy. In certain embodiments, the second therapeutic agent may be an immunomodulatory agent. In certain embodiments, the second therapeutic agent may be a monoclonal antibody, an antibody drug conjugate, a bispecific antibody conjugated to an anti-tumor agent, a checkpoint inhibitor, or combinations thereof. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-MSLN×anti-TCA bispecific antigen-binding molecule as disclosed herein) may also be administered as part of a therapeutic regimen comprising one or more therapeutic combinations selected from a monoclonal antibody other than those described herein, which may interact with a different antigen on the tumor cell, a bispecific antibody or bispecific antigen-binding molecule, which has one arm that binds to an antigen on the tumor cell surface and the other arm binds to an antigen on a T cell, an antibody drug conjugate, a bispecific antibody or bispecific antigen-binding molecule conjugated with an anti-tumor agent, a checkpoint inhibitor or combinations thereof.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-MSLN antibody or a bispecific antigen-binding molecule that specifically binds MSLN and a human TCA) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-MSLN antibody or a bispecific antigen-binding molecule that specifically binds MSLN and a human TCA). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 1 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-MSLN antibodies of the present invention may also be used to detect and/or measure MSLN, or MSLN-expressing cells in a sample, e.g., for diagnostic purposes. For example, an anti-MSLN antibody, or fragment thereof, may be used to diagnose a condition or disease characterized by aberrant expression (e.g., over-expression, under-expression, lack of expression, etc.) of MSLN. Exemplary diagnostic assays for MSLN may comprise, e.g., contacting a sample, obtained from a patient, with an anti-MSLN antibody of the invention, wherein the anti-MSLN antibody is labeled with a detectable label or reporter molecule. Alternatively, an unlabeled anti-MSLN antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Another exemplary diagnostic use of the anti-MSLN antibodies of the invention includes $^{89}$Zr-labeled, such as $^{89}$Zr-desferrioxamine-labeled, antibody for the purpose of noninvasive identification and tracking of tumor cells in a subject (e.g. positron emission tomography (PET) imaging). (See, e.g., Tavare, R. et al. Cancer Res. 2016 Jan. 1; 76(1):73-82; and Azad, B B. et al. Oncotarget. 2016 Mar. 15; 7(11):12344-58.) Specific exemplary assays that can be used to detect or measure MSLN in a sample include enzyme-linked immunosorbent assay (ELISA), radioimmunoassay (RIA), and fluorescence-activated cell sorting (FACS).

Samples that can be used in MSLN diagnostic assays according to the present invention include any tissue or fluid 49). The genetically modified mouse comprises DNA encoding human immunoglobulin heavy and kappa light chain variable regions.

Chimeric antibodies to MSLN were initially isolated having a human variable region and a mouse constant region. The antibodies were characterized and selected for desirable characteristics, and the mouse constant regions were replaced with a desired human constant region, for example wild-type or modified IgG1 or IgG4 constant region, to generate fully human anti-MSLN antibodies.

Table 1 sets forth the amino acid sequence identifiers of the heavy and light chain variable regions and CDRs of anti-MSLN antibodies of the disclosure.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 1A12b | 1 | 3 | 4 | 5 | 2 | 6 | 7 | 8 |
| 1E1e | 9 | 11 | 12 | 13 | 10 | 14 | 15 | 16 |
| 4B12a | 17 | 19 | 20 | 21 | 18 | 22 | 23 | 24 |
| 3G2b | 25 | 27 | 28 | 29 | 26 | 30 | 31 | 32 |
| 3F11f | 33 | 35 | 36 | 37 | 34 | 38 | 39 | 40 |
| 2F1a | 41 | 43 | 44 | 45 | 42 | 46 | 47 | 48 | sample obtainable from a patient which contains detectable quantities of MSLN protein, or fragments thereof, under normal or pathological conditions. Generally, levels of MSLN in a particular sample obtained from a healthy patient (e.g., a patient not afflicted with a disease or condition associated with abnormal MSLN levels or activity) will be measured to initially establish a baseline, or standard, level of MSLN. This baseline level of MSLN can then be compared against the levels of MSLN measured in samples obtained from individuals suspected of having a MSLN related disease (e.g., a tumor containing MSLN-expressing cells) or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Anti-MSLN Antibodies

Figure 1:
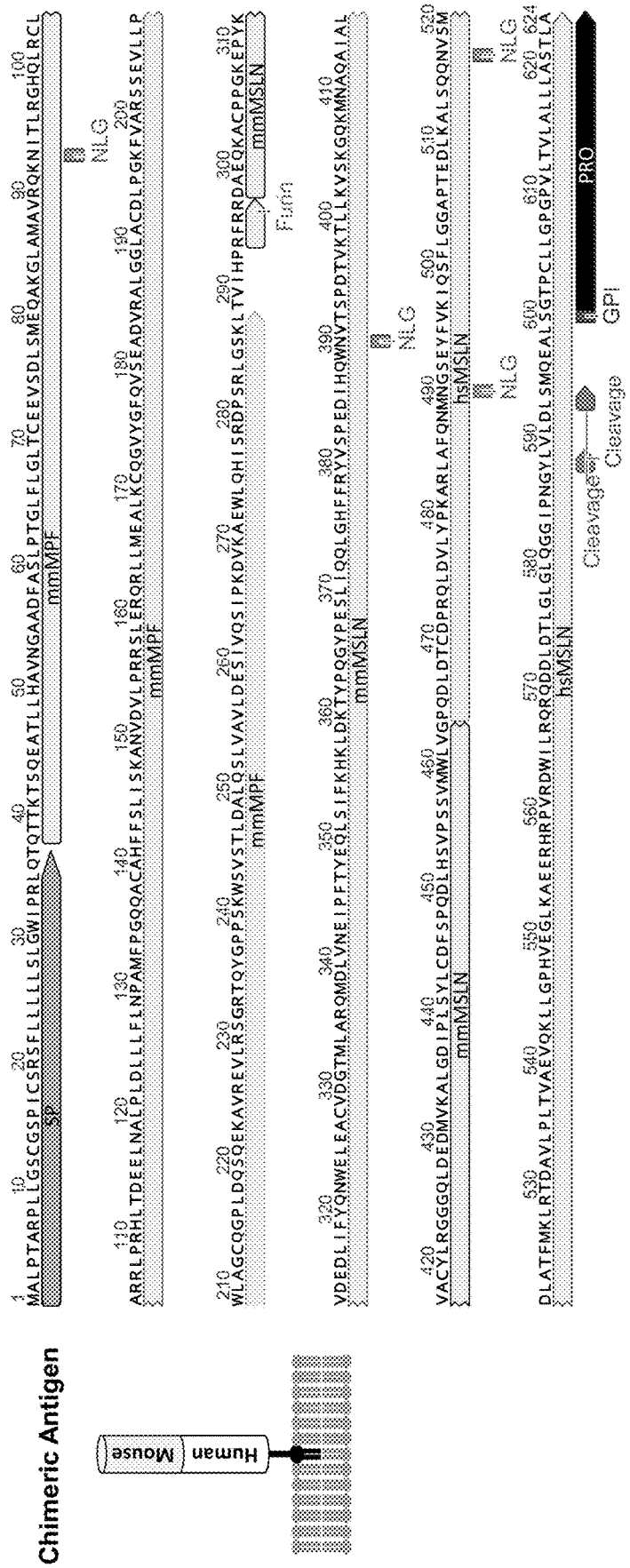
FIG. 1 illustrates a chimeric antigen designed to produce antibodies against the C-terminal portion of human mesothelin. The amino acid sequence illustrated in this figure is set forth in SEQ ID NO: 49.
Figure 2A:
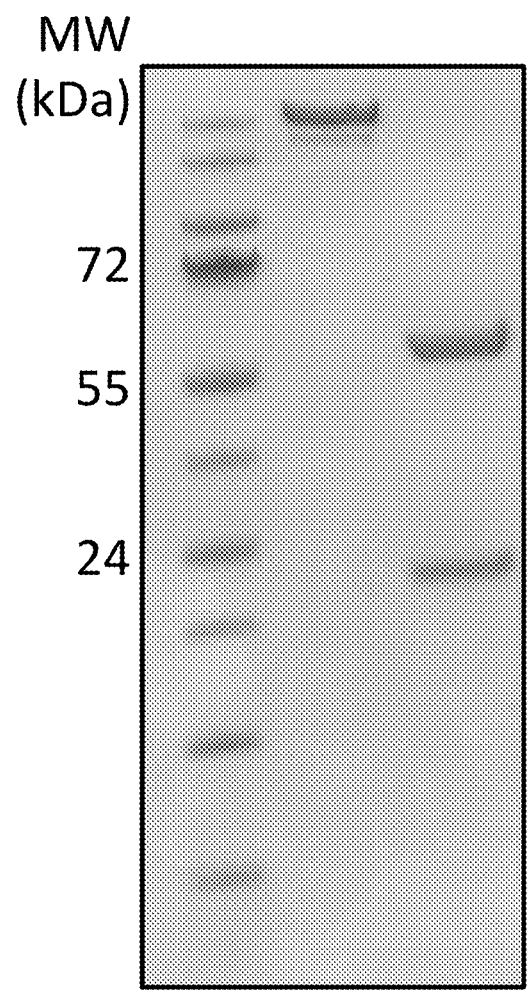
FIGS. 2A, 2B and 2C illustrate an SDS-PAGE gel showing reducing and non-reducing samples of a recombinant anti-MSLN antibody designated 1A12 (FIG. 2A), quantitation and dynamic light scattering data showing a recombinant antibody (FIG. 2B), and binding of the 1A12 anti-MSLN antibody assessed by flow cytometry (FIG. 2C).
Figure 2B:
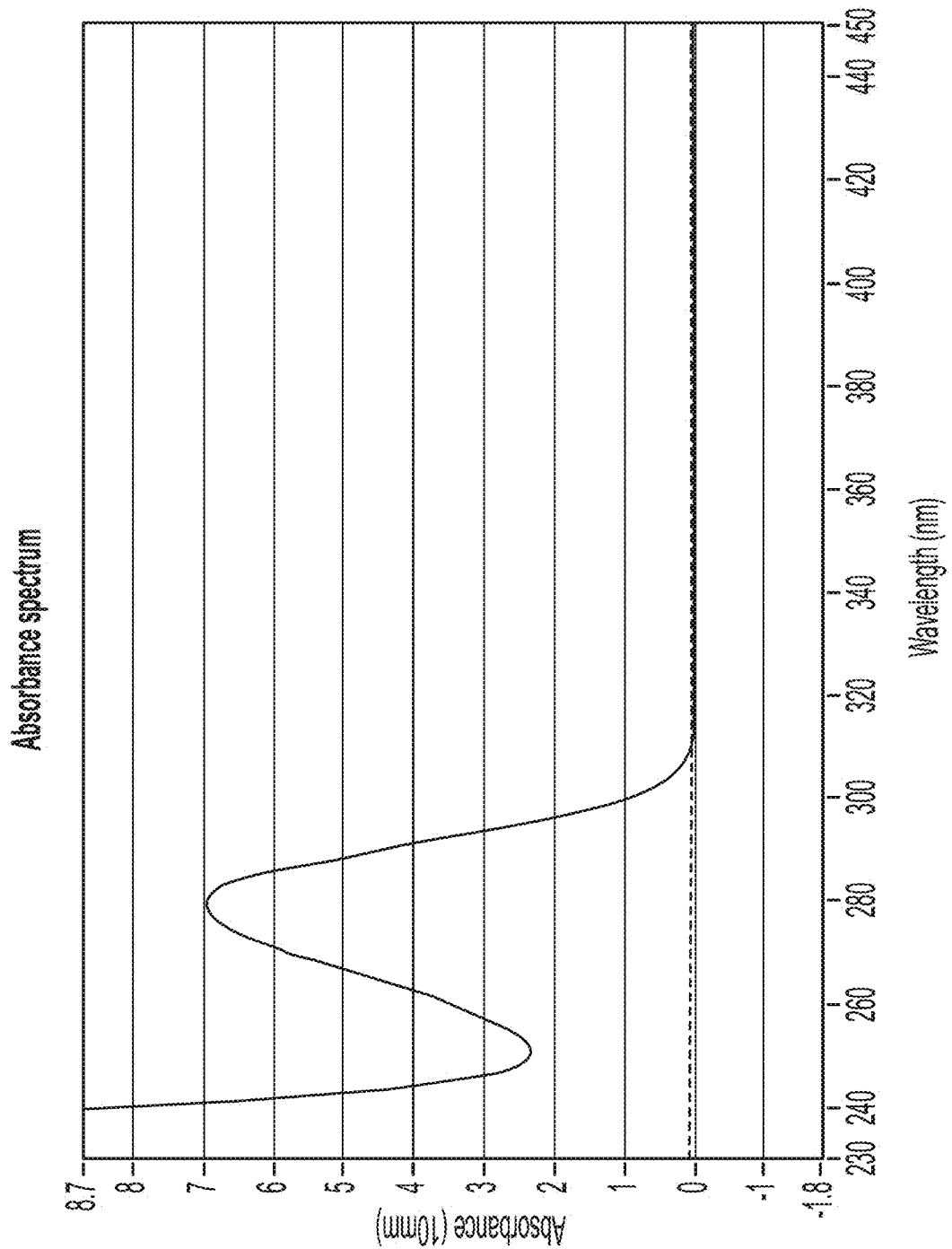
Figure 2C:
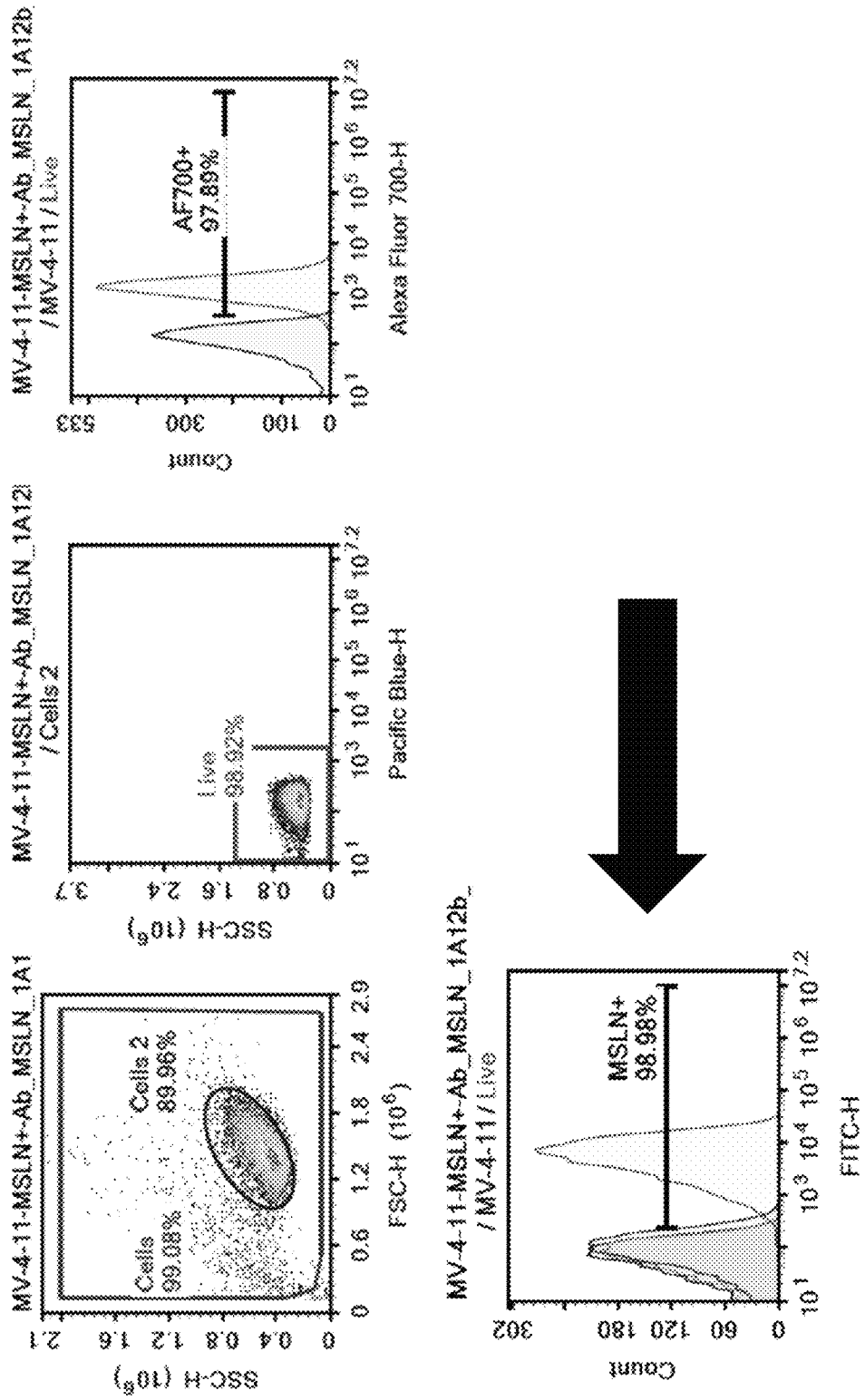

Anti-MSLN antibodies were obtained by immunizing a genetically modified mouse with murine 3T3 cells (ATCC: CRL-1658) transduced with a lentivirus encoding a chimeric MSLN antigen comprising the extracellular domain (ECD) of membrane-bound mesothelin in which the N-terminal portion of the ECD is murine and the C-terminal portion of the ECD is human, as shown in FIG. 1 (e.g., SEQ ID NO:

Recombinant anti-MSLN antibodies with a human IgG1 heavy chain constant region were expressed in 293-F cells, purified using HITRAP™ MABSELECTSURE™ columns (GE: 28408255) and subsequently polished using size exclusion chromatography on a SUPERDEX™ 200 Increase 10/300 GL (GE: 28990944). UV/Vis concentration and Dynamic Light Scattering (DLS) size measurements were collected on a Stunner instrument (Unchained Labs). The results shown in FIGS. 2A-2C demonstrate the successful production and purification of anti-MSLN antibodies (data shown is for the 1A12 anti-MSLN antibody).

Example 2: Generation of Bi-Specific Antigen-Binding Molecules

Bispecific antigen-binding molecules that specifically bind MSLN and human CD3 were prepared in the structural formats illustrated in FIGS. 3A (IgG-scFv) and 3B (Fc-scFv) using the Fab domains or variable regions of the 1A12 anti-MSLN antibody (HCVR/LCVR=SEQ ID NOs: 1/2), and a humanized version of the OKT3 antibody variable domains (HCVR/LCVR=SEQ ID NOs: 76/77) linked to a human IgG1 Fc domain with a glycosylation mutation (N297A) to reduce binding to Fcγ receptors. The mutation at the glycosylation site prevents unwanted antibody cross-linking and T cell activity. In addition, a variant of the IgG-scFv molecule was prepared in which the orientation of the anti-CD3 binding domains was reversed (i.e., VL-VH, rather than VH-VL), which is discussed further in Example 5. The methods for producing these molecules followed standard protein expression protocols that are described in various references. Briefly, the "Daedalus" human cell line expression platform was employed for the production and purification of secreted proteins. The expression system made use of suspension adapted HEK293 Freestyle cells and a highly optimized lentiviral transduction protocol to generate cell lines that secrete proteins at high levels. The lentiviral vector contained a cis-linked fluorescent protein reporter driven by an internal ribosome entry site (IRES) that allowed for tracking of relative protein expression levels. All mammalian proteins described were purified directly from conditioned media using HisTrap FF Crude columns (GE #17528601) and subsequently polished on a Superose 6 10/300 GL SEC column (GE #17517201) using an AKTA pure 25 instrument.

The bispecific antigen-binding molecules were purified and characterized using standard techniques. Representative chromatograms and gels showing the purification of the IgG-scFv molecule with the structure of FIG. 3A are shown in FIGS. 4A-4D, confirming successful production with minimal aggregates.

Figure 5C:
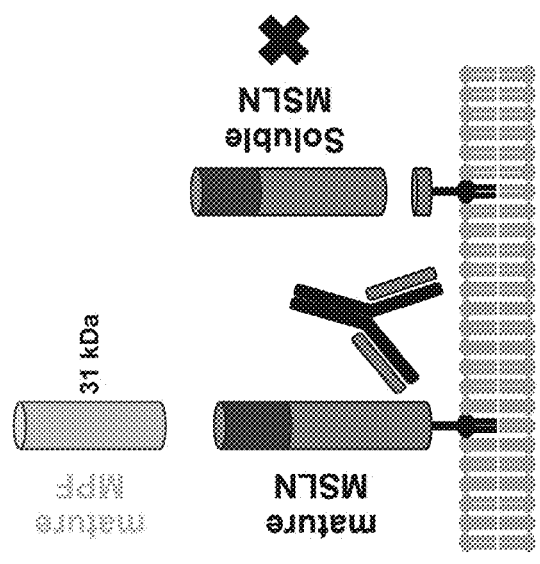
Figure 5D:
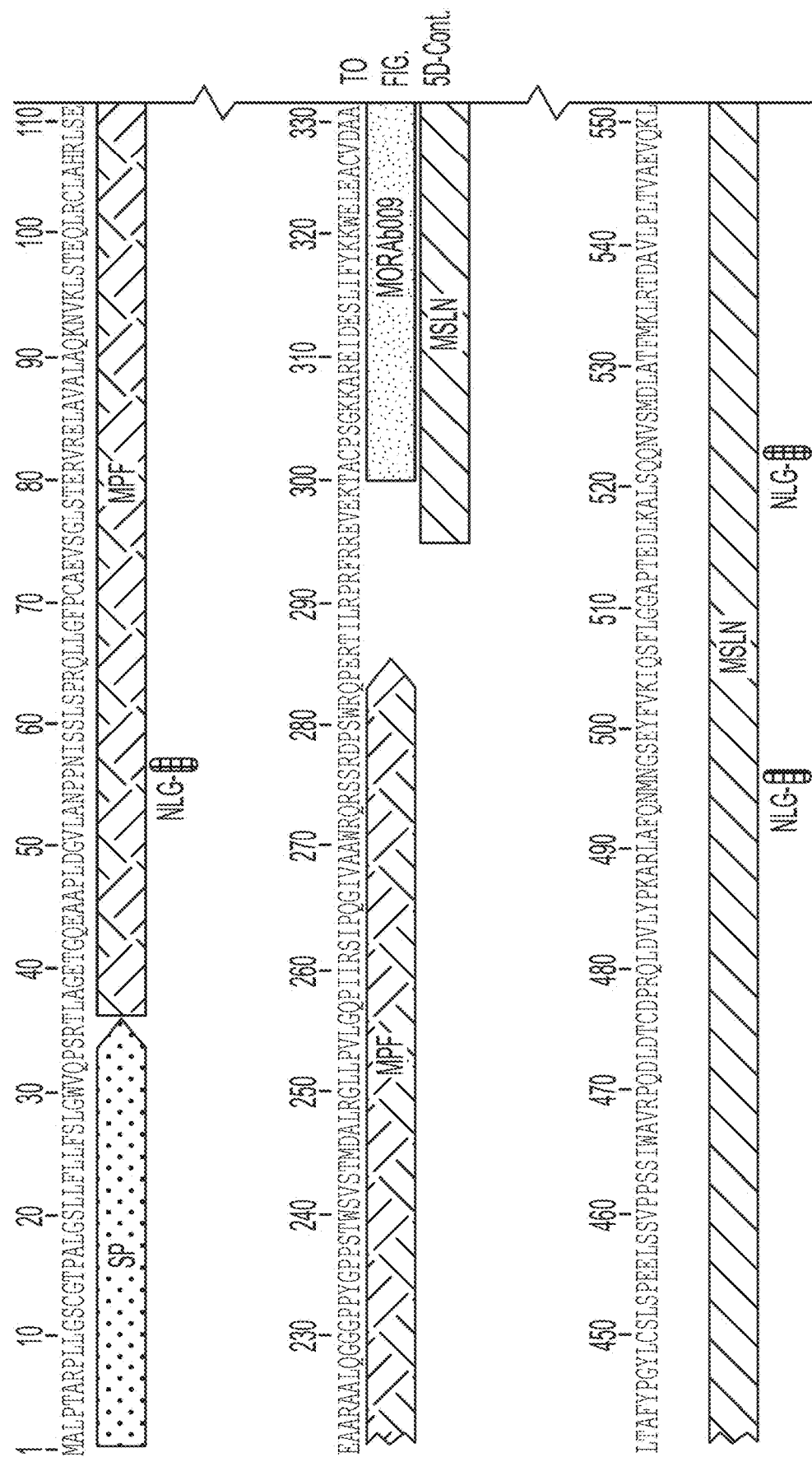
Figure 6:
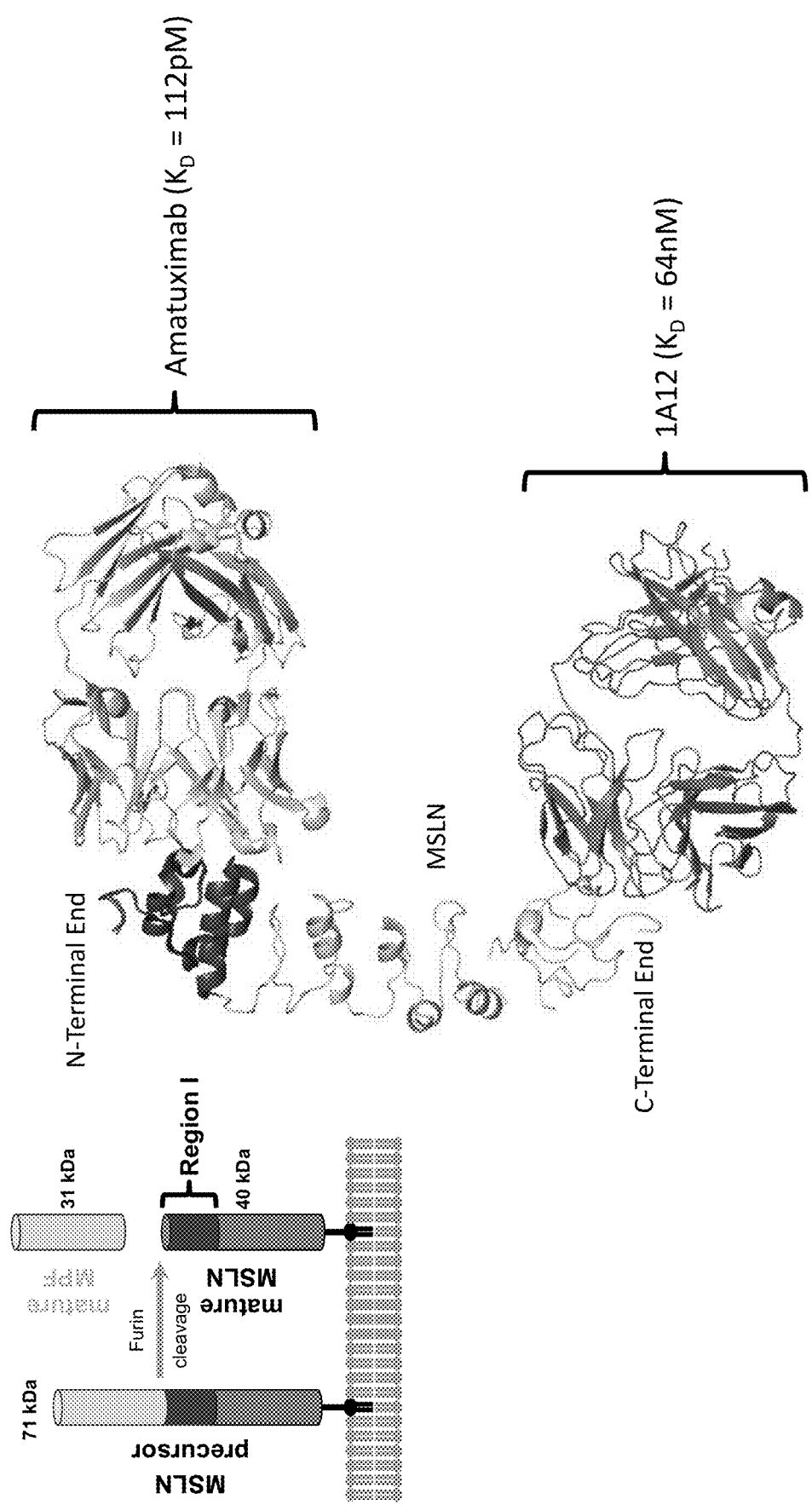
FIG. 6 illustrates the crystal structure of the 1A12 anti-MSLN antibody (as a Fab fragment) bound to MSLN at an epitope distinct from that of amatuximab and other known anti-MSLN antibodies. The crystal structure of amatuximab (PDB ID: 4F3F) has been aligned to the experimentally determined structure to highlight the differences between the two antibodies.

Example 3: Crystal Structure and Surface Plasmon Resonance Derived Binding Affinities to Mesothelin Mature mesothelin is a membrane-bound protein, as illustrated in FIG. 5A. The antigen-binding domains of amatuximab, a known anti-MSLN antibody, bind near the N-terminus of mesothelin, as shown in the crystal structure of FIG. 5B, and in the schematic of FIG. 5D (MORAb009 is amatuximab). The mature form of mesothelin is also susceptible to cleavage near the C-terminus, which produces a soluble form of the protein, as illustrated in FIG. 5C. The anti-mesothelin antibodies of the present disclosure bind to the C-terminus of membrane-bound mesothelin, but not to the soluble form of the cleaved protein. As shown in the crystal structure of FIG. 6, the 1A12 anti-MSLN antibody binds to the membrane proximal C-terminus of mesothelin, wherein amatuximab binds to the membrane distal N-terminus of mesothelin. The anti-MSLN antibodies used for the co-crystallization discussed above and for the surface plasmon resonance experiments discussed below were expressed from 293-F cells and purified using HITRAP™ MABSELECTSURE™ columns (GE 28408255). Fab fragments were generated using immobilized papain (ThermoFisher: 20341) and Fab:MSLN complexes were purified using size exclusion chromatography. The human ectodomain of MSLN was also expressed in human 293-F cells (ThermoFisher: R79007) as a fusion protein with Siderocalin. The sFlag-His-Scn-tev-MSLN-Avi fusion protein was purified from conditioned media using immobilized metal affinity chromatography on a HisTrap FF Crude column (GE: 17528601) and cleaved using TEV protease. The MSLN-Avi ectodomain was then purified using size exclusion chromatography on a SUPERDEX™ 200 Increase 10/300 GL (GE: 28990944).

Surface plasmon resonance (SPR) experiments were performed at 25° C. on a BIACORE™ T100 instrument (GE Healthcare) with a Series S CM4 chip using a running buffer of 10 mM HEPES, pH 7.4, 150 mM NaCl, 3 mM EDTA, 0.05% surfactant P20 with 0.1 mg/mL bovine serum albumin. Goat anti-human Fc antibody (Jackson Labs: 109005098) was amine coupled to the CM4 chip (~2800 RUs) and each antibody was then captured on a single flow cell of immobilized goat anti-human Fc. The purified MSLN-Avi (discussed above) was run as a concentration series at 50 uL/min over the captured antibodies and the goat anti-human Fc reference surface. CM4 chip was regenerated with 10 mM glycine, pH1.5 for 30 sec at 50 uL/min. Data was double referenced and analyzed in BiaEval 2.0.4. Data and 1:1 binding model fits are shown in FIGS. 7A-7D for the 1A12 anti-MSLN antibody, an IgG-scFv anti-MSLN bispecific molecule comprising the anti-MSLN antigen binding domains from the 1A12 antibody, an Fc-scFv anti-MSLN bispecific molecule comprising the anti-MSLN antigen binding domains from the 1A12 antibody, and amatuximab, respectively.

As shown in FIGS. 7A-7D, incorporation of the anti-MSLN antigen-binding domains of the 1A12 anti-MSLN antibody into the bispecific molecular formats did not significantly change the binding affinity to MSLN for the IgG-scFv molecule, and only slightly lowered the binding affinity for the Fc-scFv molecule, while amatuximab was shown to have a binding affinity for MSLN that is about 600-fold higher (lower $K_D$) than the 1A12 anti-MSLN antibody.

Example 4: Pharmacokinetic Analysis of Anti-MSLN Molecules

Mice were dosed as shown in Table 2, below, using the following parameters: 1.42 nmole/mouse, which equates to 75 μg/mouse of the scFv-scFv; 200 μL dosing solution/20 g mouse; and all proteins formulated in PBS and dosed IV tail. Blood was collected via the saphenous vein into a heparinized tube, and 2 μL whole blood analyzed by LSC. Blood was collected as follows: 3 minutes, 30 minutes, 1 hour, 2 hours, 6 hours, 24 hours, 3 days, and 7 days.

TABLE 2

| | PK Dosing | | |
|---|---|---|---|
| Protein | MDT-481 (scFv-scFv) | MDT-619/620 (IgG-scFv) | MDT-604/402 (IgG) |
| Final mg recovered | 4.27 mg | 5.84 mg | 7.87 mg |
| Concentration | 2.28 mg/mL | 2.59 mg/mL | 2.62 mg/mL |
| Specific Activity | 13.54 μCi/mg | 17.24 μCi/mg | 15.66 μCi/mg |
| Activity of 1.42 nMol | 1.02 μCi | 4.91 μCi | 3.21 μCi |
| Dose/mouse (1.42 nmole) | 3 mg/kg 75 μg/25 g mouse 0.3 mg/mL dosing | 11.4 mg/kg 285 μg/25 g mouse 1.14mg/mL dosing | 8.2 mg/kg 205 μg/25 g mouse 0.82 mg/mL dosing |
| Dilution for Dosing | 237 μL in 1.8 mL | 792 μL in 1.8 mL | 563 μL in 1.8 mL |

Figure 8A:
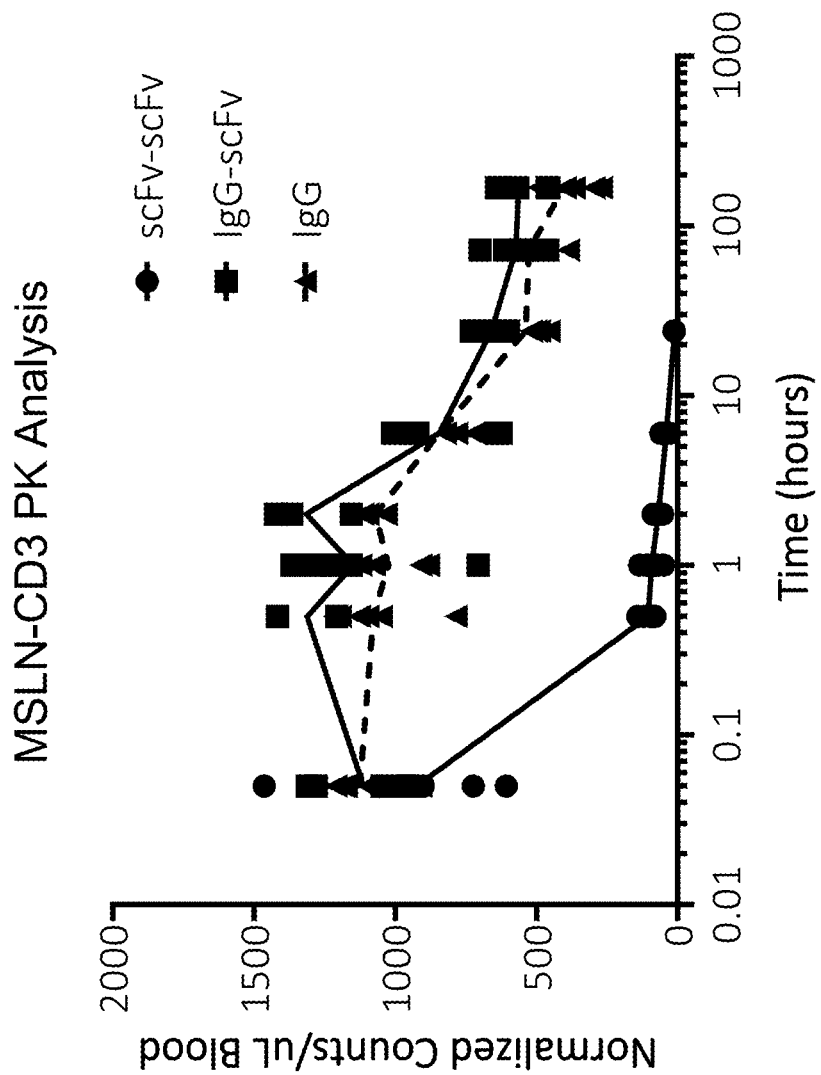
FIGS. 8A and 8B illustrate the radioactive counts in blood of three different molecular formats, a canonical BiTE® (Amgen), an IgG-scFv molecule with the structure of FIG. 3A, and an IgG antibody (FIG. 8A), and a pharmacokinetic analysis showing that the IgG-scFv molecule has a serum half-life similar to that of an IgG antibody (FIG. 8B).
Figure 8B:
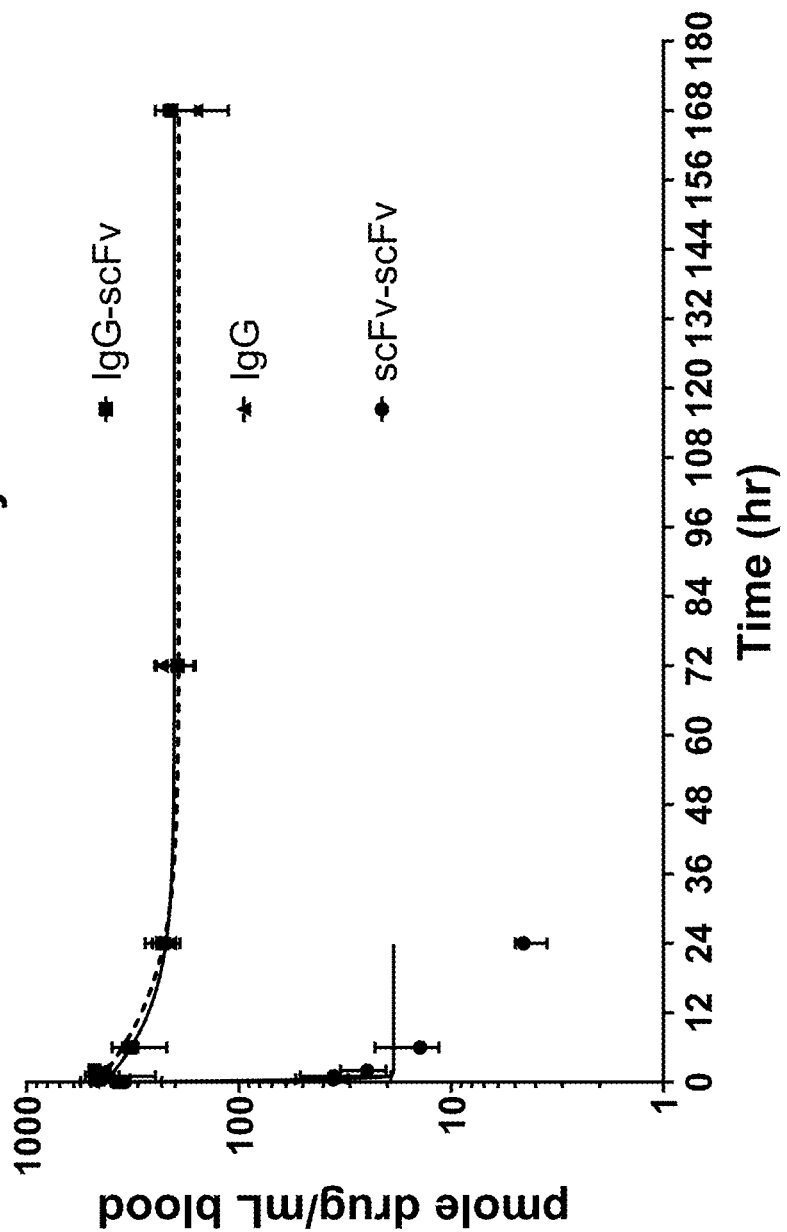

As shown in FIGS. 8A and 8B, the anti-MSLN antibody amatuximab (IgG) and the IgG-scFv bispecific molecule (with amatuximab anti-MSLN binding domains) showed comparable pharmacokinetics in the mice, and had a significantly longer half-life than the canonical BiTE molecule (with amatuximab anti-MSLN binding domains).

Example 5: Surface Expression and FACS Binding to Mesothelin+ and CD3+ Cells

Figure 9A:
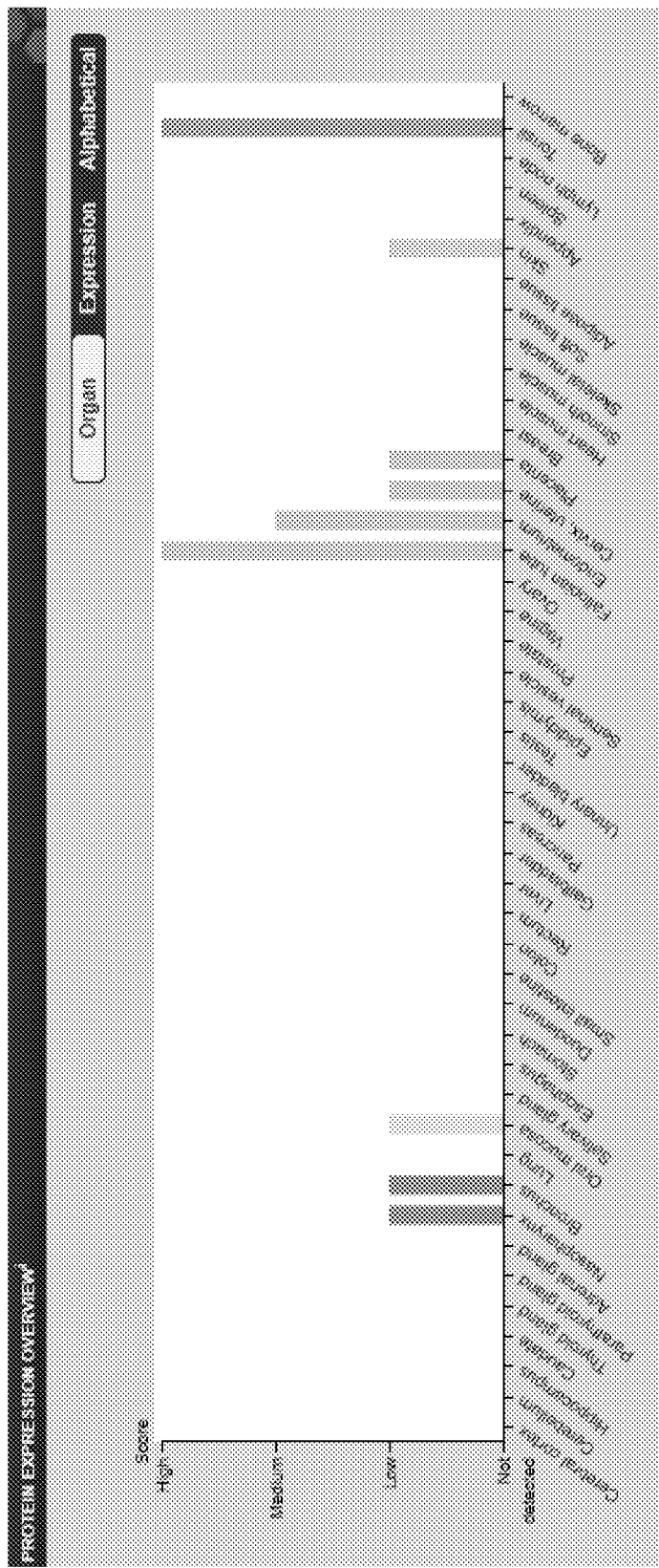
FIG. 9A illustrates the expression levels of MSLN in various healthy tissues. Data is from www.proteinatlas.org/ENSG00000102854-MSLN.
Figure 9A:
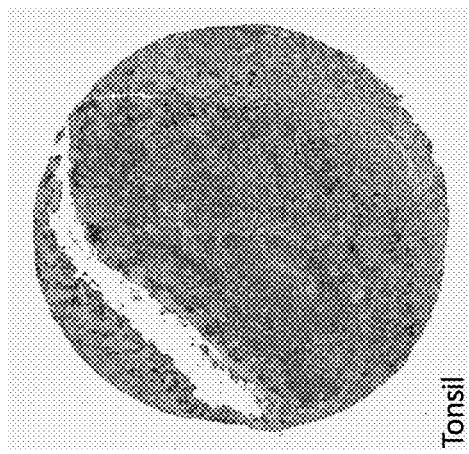
Figure 9A:
Figure 9C:
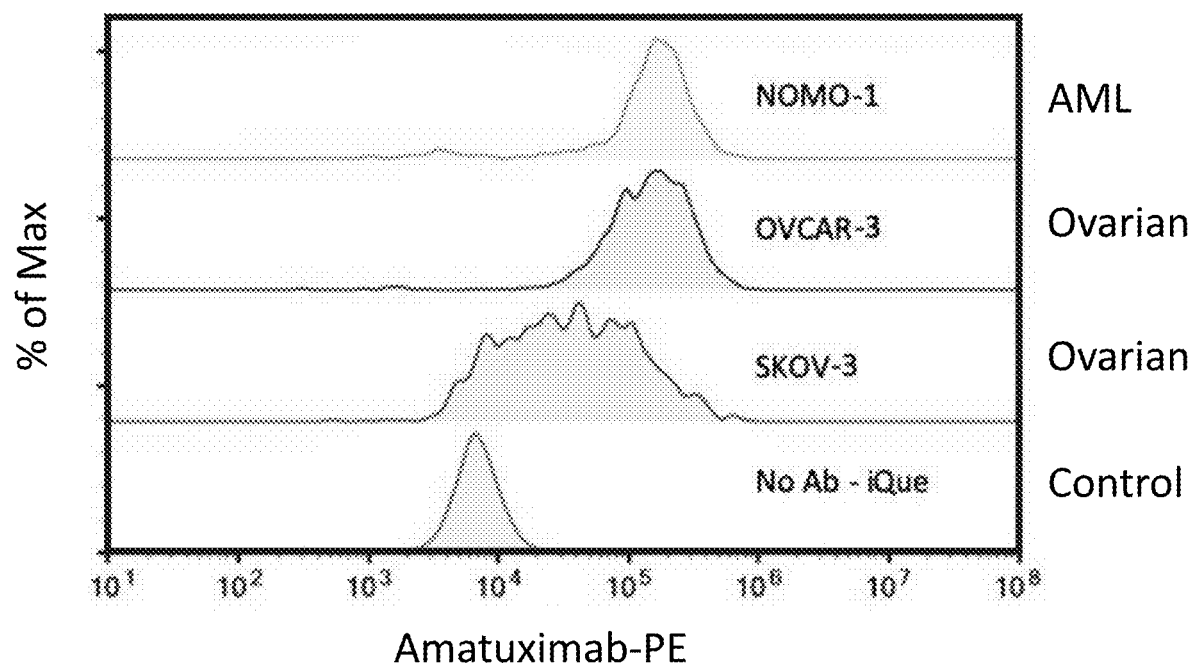
Figure 9C:
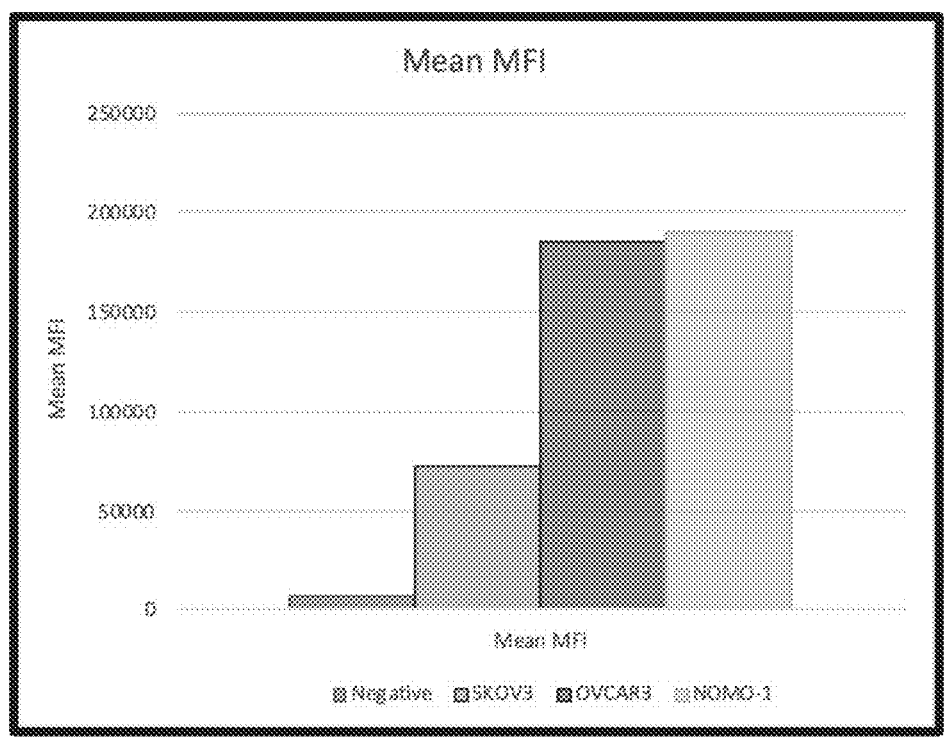

Mesothelin is normally expressed in a number of healthy tissues, as shown in FIG. 9A. To evaluate the binding of the molecules of the present disclosure to MSLN-expressing cells, MSLN expression on various AML cell lines and cancer cell lines was determined using flow cytometry. Briefly, adherent lines were dissociated with TRYPLE™ Express (ThermoFisher) and washed with staining buffer (1×PBS+2% FBS+1 mM EDTA). In a 96-well plate, cells were seeded at $5 \times 10^5$ in 50 µL of staining buffer. Primary antibody was added at a concentration of 2 µg/mL and incubated for 30 min on ice in the dark. Cells were then washed 3× with staining buffer and resuspended in 50 µL total volume. Fluor-conjugated secondary antibody (THE His Tag Antibody (IFLUOR™ 647), Genscript) was added at 2 µg/mL and incubated similarly as primary antibody. Cells were then washed 3× with staining buffer and resuspended in 50 µL total volume of staining buffer+1× DAPI and analyzed on INTELLICYT™ IQUE™ Screener with ForeCyt software (Sartorius). Fluor-conjugated primary antibodies of the target(s) of interest (Biolegend) were used as controls. The results are shown in FIGS. 9B and 9C. As shown in FIG. 9B, the MV4;11+MSLN cell line has very high surface expression of MSLN, while the Nomo-1-MSLN$^{KO}$ cell line has very low surface expression of MSLN.

Figure 10:
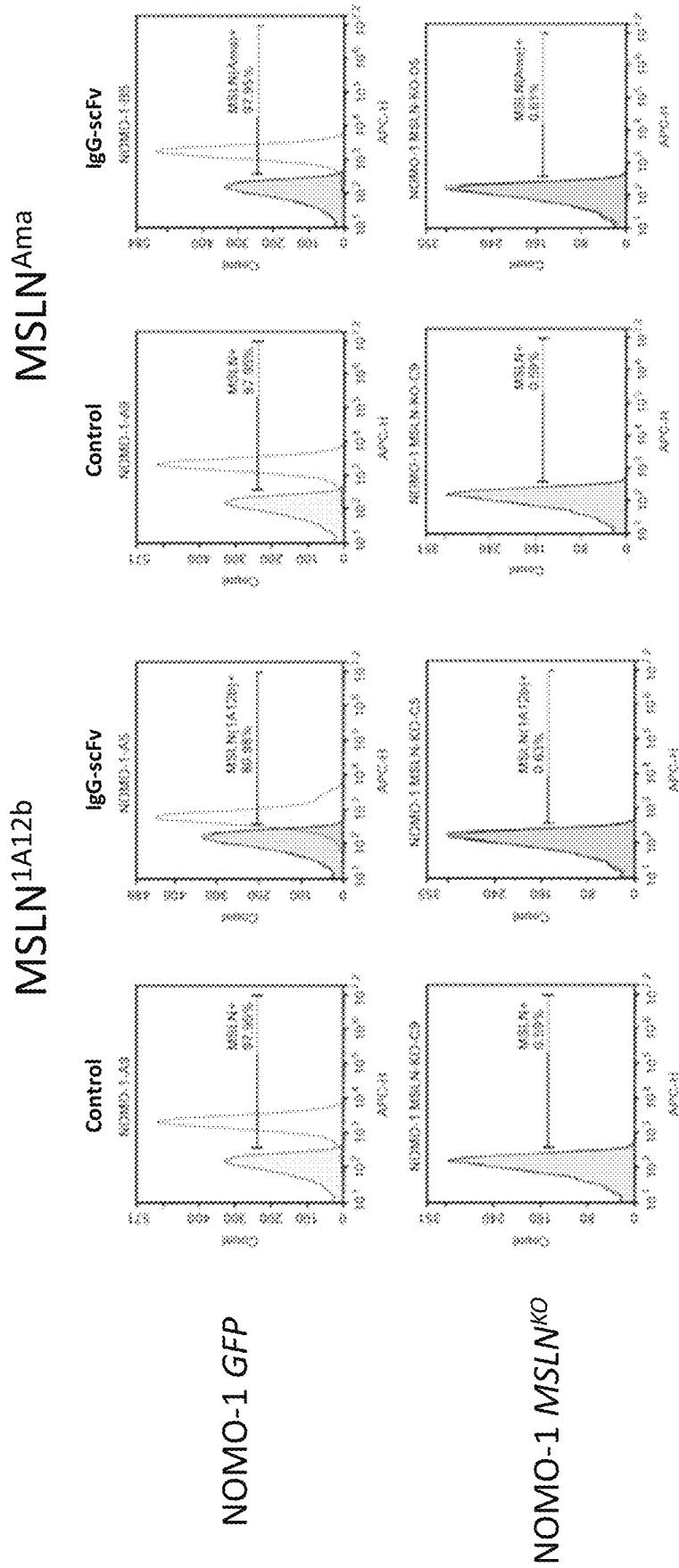
FIG. 10 illustrates FACS binding data showing the binding of a bispecific molecule with the structure of FIG. 3A and comprising anti-MSLN binding domains of the 1A12 anti-MSLN antibody or amatuximab, relative to the amatuximab antibody control. The NOMO-1 cell line is a low MSLN-expressing cell line, as shown in FIG. 9B, but both IgG-scFv molecules bound to the MSLN-expressing cells, and failed to bind to the MSLN-knock out cells.
Figure 11:
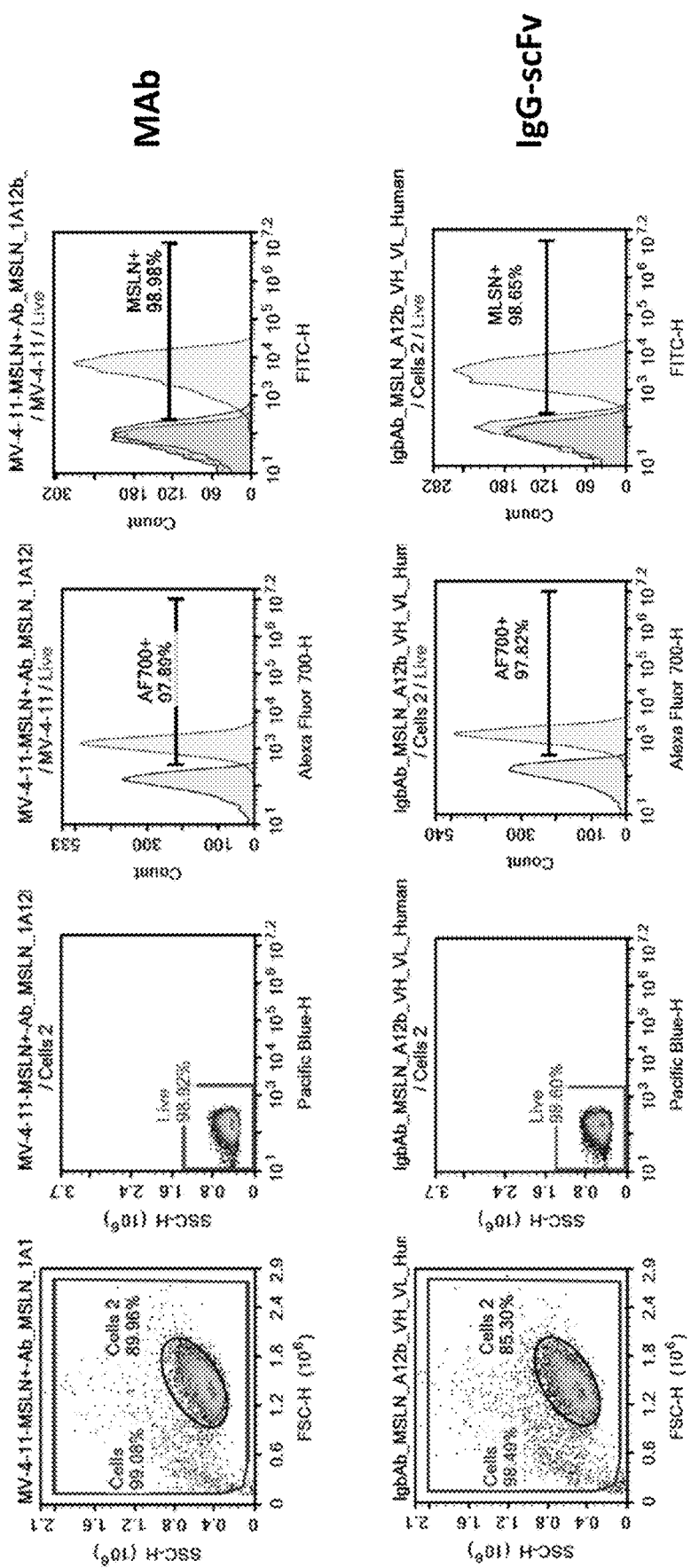
FIG. 11 illustrates FACS binding data showing comparable binding, to high MSLN-expressing cells (as shown in FIG. 9B), of the 1A12 anti-MSLN antibody and the IgG-scFv bispecific molecule (of FIG. 3A) with anti-MSLN binding domains from the 1A12 antibody
Figure 12:
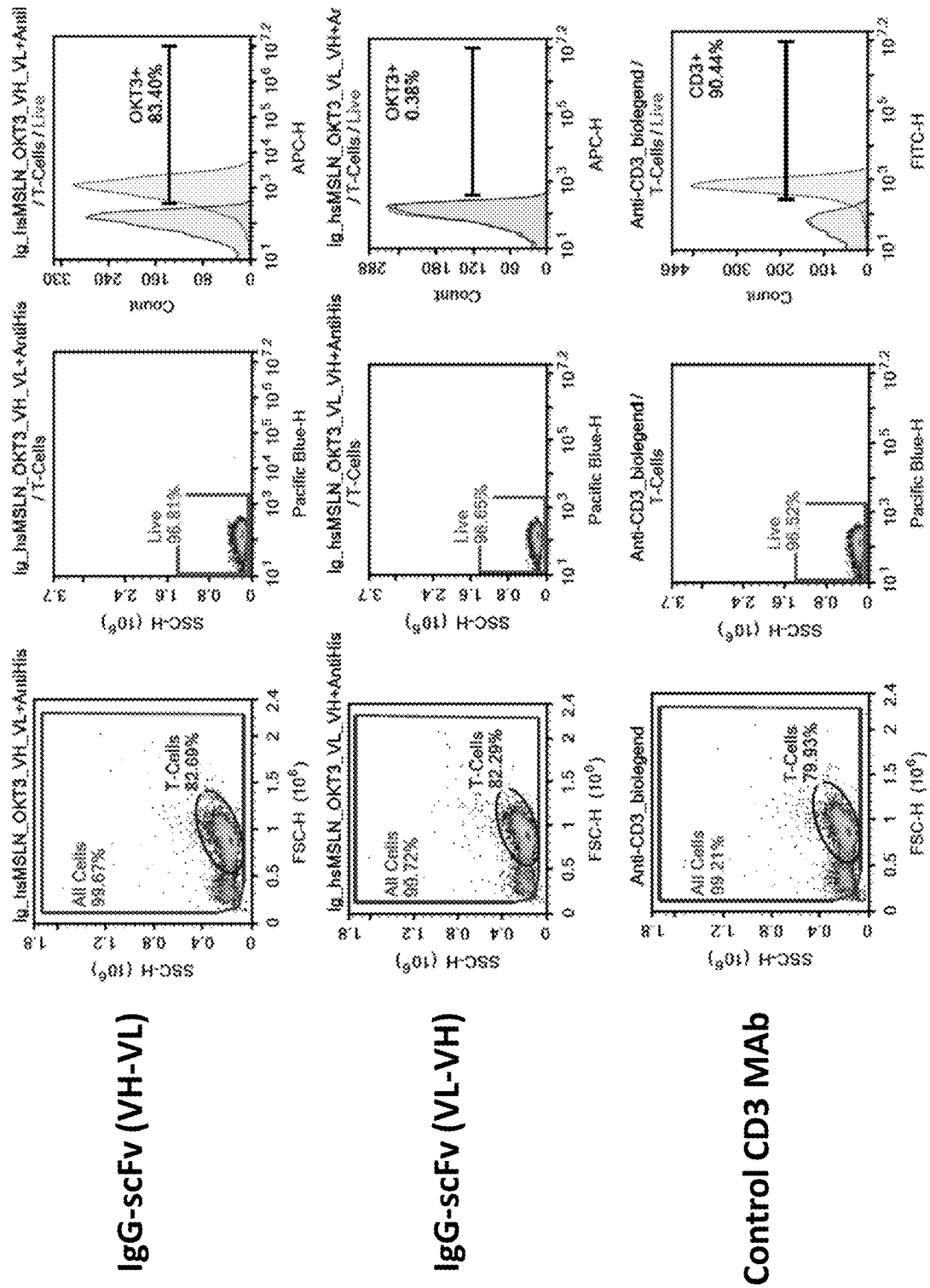
FIG. 12 shows FACS binding data comparing the relative binding of the IgG-scFv molecule in which the anti-CD3 antigen-binding domains are a humanized version of the OKT3 anti-CD3 antibody. As shown, the orientation of the scFv portion of the molecule determines binding to CD3+ cells. When the orientation of the scFv portion is VH-VL, as illustrated in FIG. 3A, the molecule shows good binding to CD3+ cells, but when the orientation of the scFv portion is reversed to VL-VH, the molecule no longer shows binding to CD3+ cells.

The ability of an anti-MSLN antibody (1A12), and an anti-MSLN×CD3 bispecific molecule in the IgG-scFv format of FIG. 3A (with the 1A12 anti-MSLN antigen-binding domains), to bind the surface of MSLN positive AML cells (MV4-11, and NOMO-1), MSLN knock down (NOMO-1-MSLN$^{KO}$ cells, and CD3-positive cells was determined via flow cytometry. As shown in FIG. 10, the bispecific molecule (IgG-scFv) with anti-MSLN antigen-binding domains from the 1A12 antibody or amatuximab bound comparably to the moderately MSLN-expressing NOMO-1 cell line, while no binding was detected to the NOMO-1-MSLN$^{KO}$ knock-down cell line. As shown in FIG. 11, comparable binding to high MSLN-expressing MV4-11 cells was observed with the anti-MSLN 1A12 antibody and the IgG-scFv bispecific molecule (with the 1A12 anti-MSLN antigen-binding domains). As shown in FIG. 12, the orientation of the anti-CD3 scFv domains of the IgG-scFv molecule determined the binding to CD3-positive T cells. When the molecule contained the VH-VL orientation, as shown in FIG. 3A, binding to T cells was comparable to the positive control. In contrast, when the orientation of the anti-CD3 scFv was reversed (VL-VH), poor binding to CD3-positive T cells was observed. In each of the IgG-scFv molecules discussed in this example, the anti-CD3 antigen-binding regions were derived from a humanized version of the OKT3 antibody.

Example 6: FACS Based Cytotoxicity Assay to Assess T Cell-Mediated Killing of MSLN-Expressing Cells in the Presence of Anti-MSLN×Anti-CD3 Bispecific Molecules In order to monitor the specific killing of MSLN-expressing cells by flow cytometry, cells with moderate surface expression of MSLN (NOMO-1 cells) were used in T cell killing assays. Briefly, a NOMO-1 cytotoxicity assay was conducted using an automated platform programmed to simultaneously conduct unbiased 96 well assays in which 100,000 T cells (obtained from healthy donors, qualified by flow cytometry for CD3, CD28, CD4, CD8 pre- and post-Easysep no-touch purification) were mixed with 20,000 Luc-iRFP cancer cells (5:1 E:T ratio) in the presence or absence of bispecific molecules (8 concentrations, ranging from 0-1 mg/ml) for 48 hour flow cytometry based readouts.

Figure 7A:
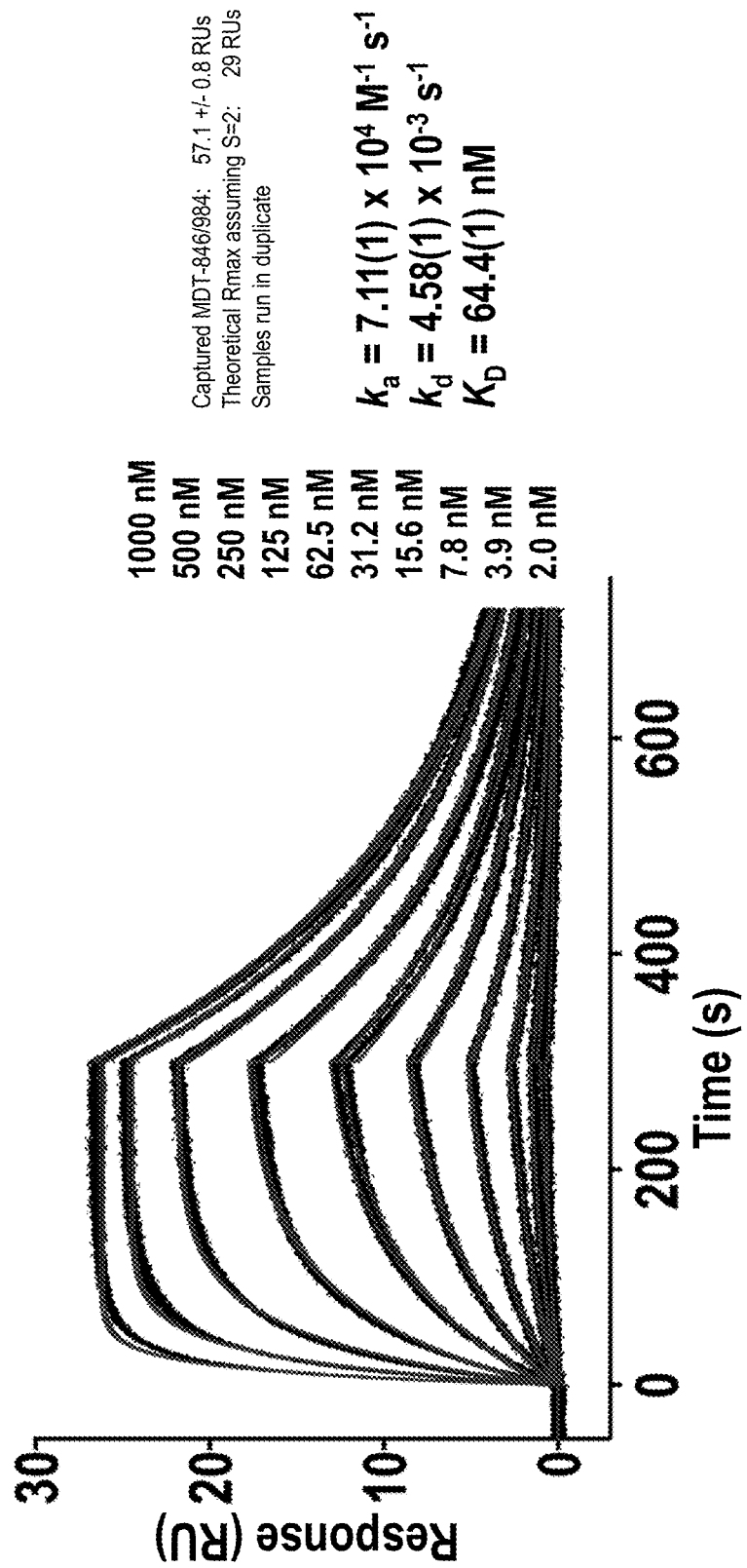
FIGS. 7A 7B, 7C and 7D illustrate the surface plasmon resonance data showing the binding kinetics of the 1A12 anti-MSLN antibody (FIG. 7A), a bispecific anti-MSLN× anti-CD3 molecule having the structure of FIG. 3A (FIG. 7B), a bispecific anti-MSLN×anti-CD3 molecule having the structure of FIG. 3B (FIG. 7C), and the amatuximab antibody (FIG. 7D).
Figure 7B:
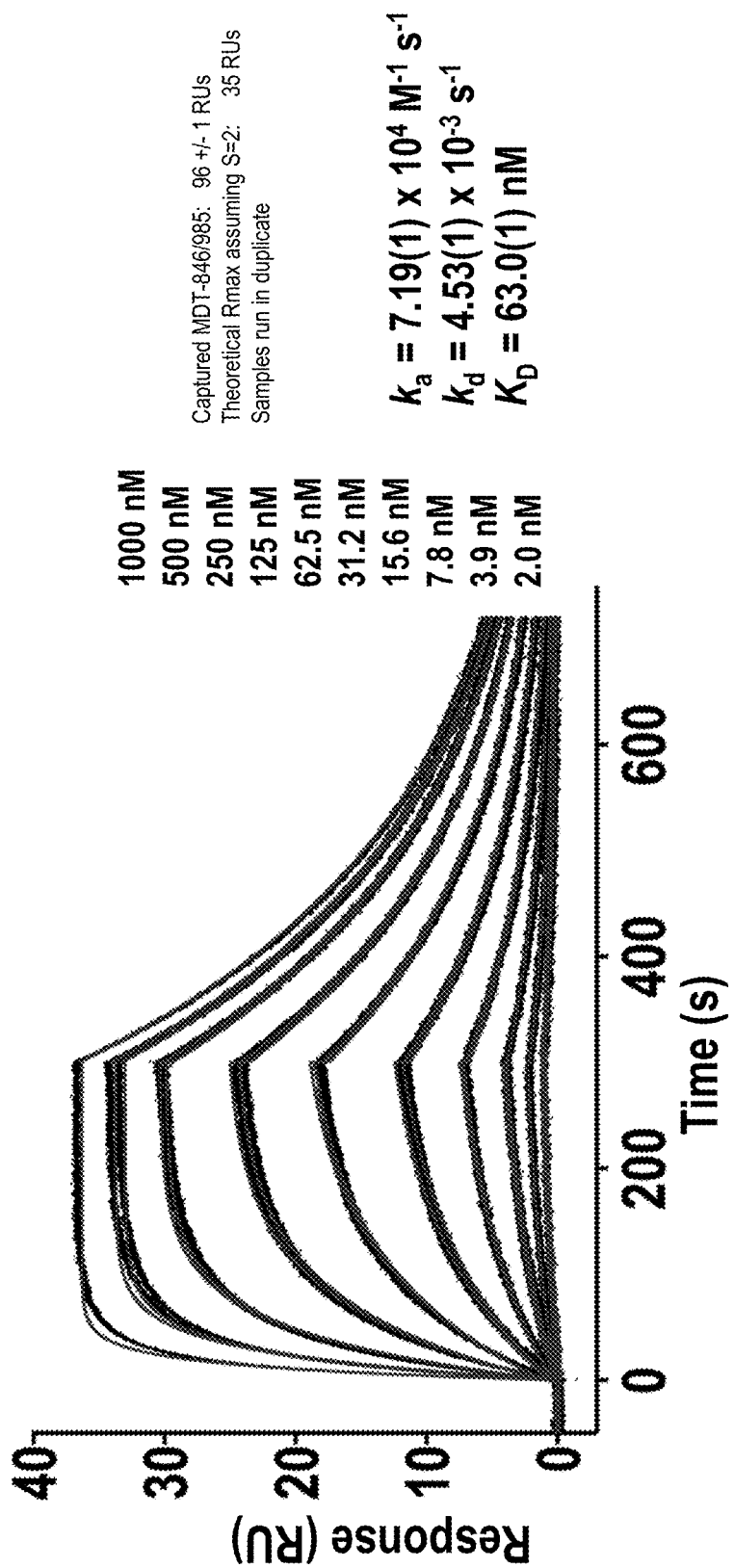
Figure 7C:
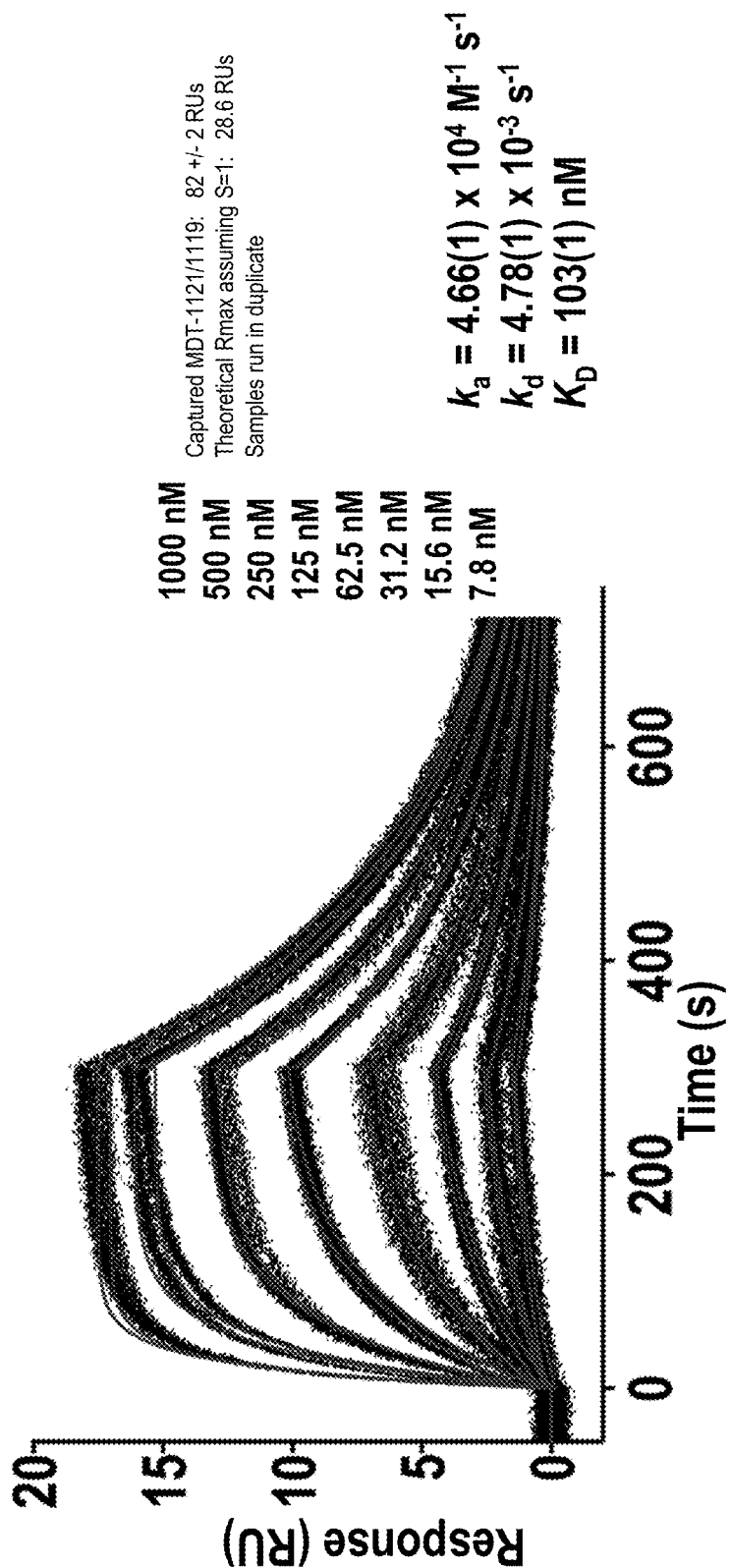
Figure 7D:
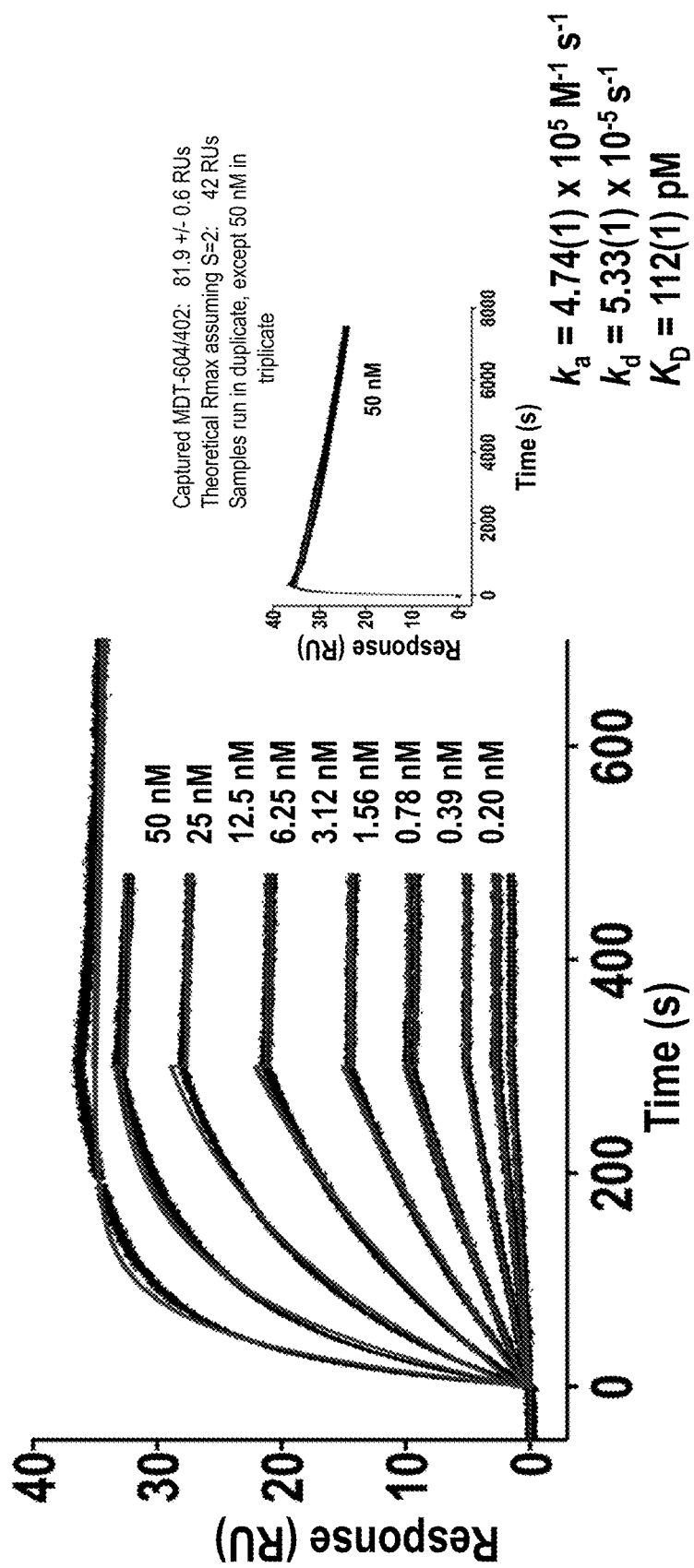

As shown in FIG. 13, the IgG-scFv molecule with the structure of FIG. 3A (with the 1A12 anti-MSLN antigen-binding domains and anti-CD3 antigen-binding domains of a humanized version of the OKT3 antibody) (labeled pMSLN:CD3) was much more potent than the same molecular structure having the anti-MSLN antigen-binding domains of the amatuximab antibody (labeled dMSLN:CD3), in spite of the greater binding affinity to MSLN of amatuximab relative to the 1A12 anti-MSLN antibody of the present disclosure (as shown in FIGS. 7A and 7D). Similarly, the IgG-scFv formatted molecule (FIG. 3A) had a relatively greater cytotoxic potency than the Fc-scFv formatted molecule (FIG. 3B), as shown in FIG. 14.

Example 7: T Cell Activation Via Bispecific Anti-MSLN×Anti-CD3 Molecules in the Presence of MSLN-Expressing Cells T cell activation by the bispecific molecules of the present disclosure was assessed via cytokine quantitation. Briefly, cytokine analysis was carried out using an automated platform programmed to use the MULTICYT™ QBEADS™ PlexScreen Secreted Protein Assay Kit (Sartorius). A bead cocktail containing antibody-coated beads against IL-2, IL-6, IFNγ, and TNFα was incubated with cell culture supernatants collected at 24 hours post-assay setup. Captured analytes were then detected using a fluor-conjugated antibody. The analytes were quantified by interpolation from a standard curve. The beads were analyzed using the IQUE™ Screener Plus flow cytometer in 384 well format and analytes were quantified using Forecyt or Prism software.

As shown in FIG. 15, the IgG-scFv molecule with the structure of FIG. 3A (with the 1A12 anti-MSLN antigen-binding domains and anti-CD3 antigen-binding domains of a humanized version of the OKT3 antibody) (labeled pMSLN:CD3) more potently induced T cell activation than did the same molecular structure having the anti-MSLN antigen-binding domains of the amatuximab antibody (labeled dMSLN:CD3). In addition, an experiment with both wild-type (WT) and knock-down (KO) versions of the NOMO-1 cell line, which has moderate surface expression of MSLN, demonstrated that little to no T cell activation is observed in the absence of the target antigen (MSLN), as shown in FIG. 16.

Example 8: Epitope Mapping of Antibodies that Recognize MSLN and Cross-Reactivity of scFv:MSLN Ectodomain Pairs Physiologic processing of MSLN, as previously discussed and as depicted at FIG. 5A, is shown again for reference (FIG. 17A). Various antibodies bind to different epitopes of MSLN (FIG. 17B). Specifically FIG. 17B illustrates a crystal structure of MSLN, and a general vicinity of where various antibodies bind thereto. The antibodies depicted include MF-T (Bayer), M912 (National Cancer Institute), 79D (Roche), MED1382 (Medarex), MORAb009 (Morphotek, Inc.), HPN536 (Harpoon Therapeutics), and 1A12 (Link Immunotherapeutics, Inc.).

Figure 18A:
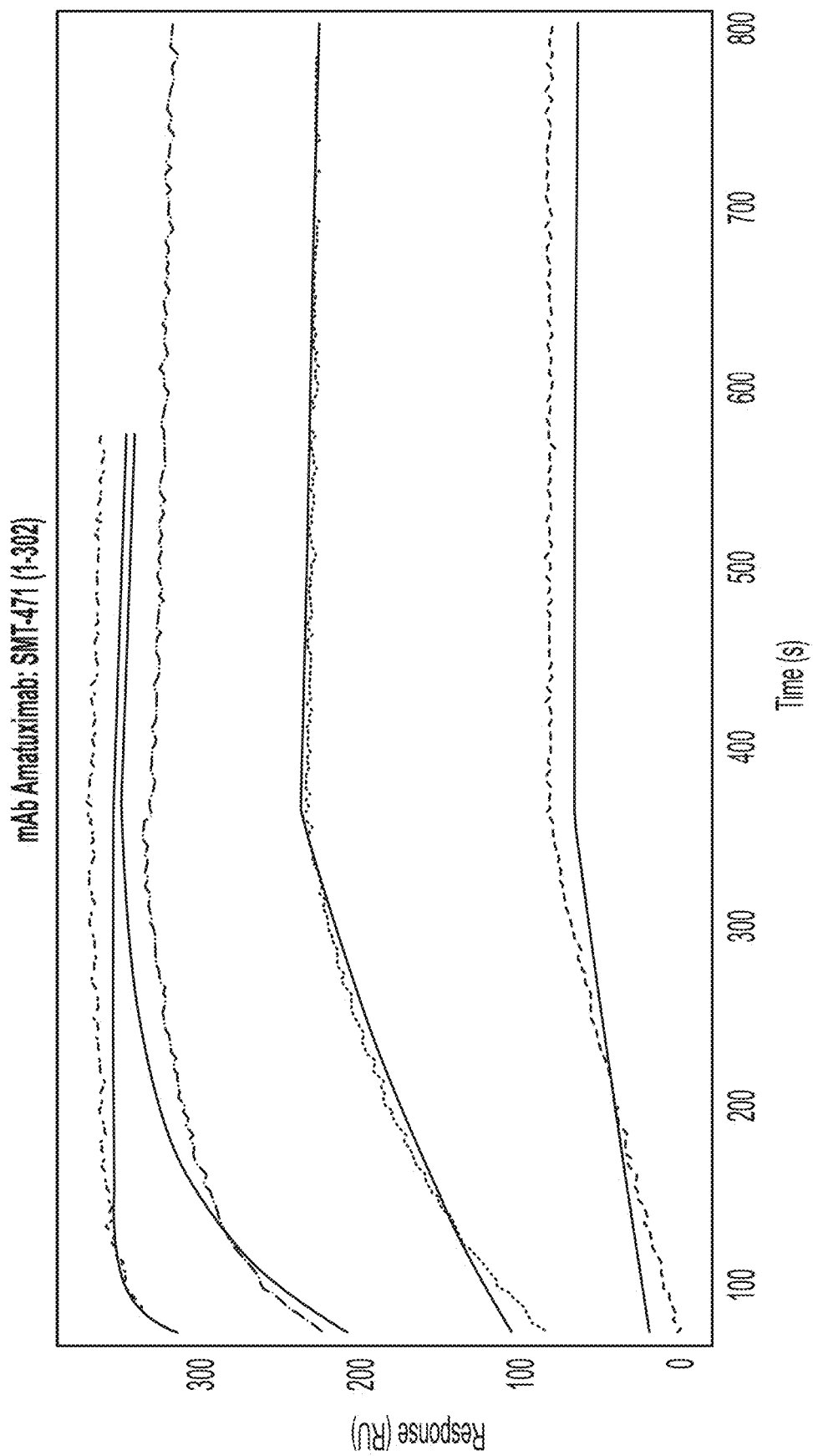
Figure 18B:
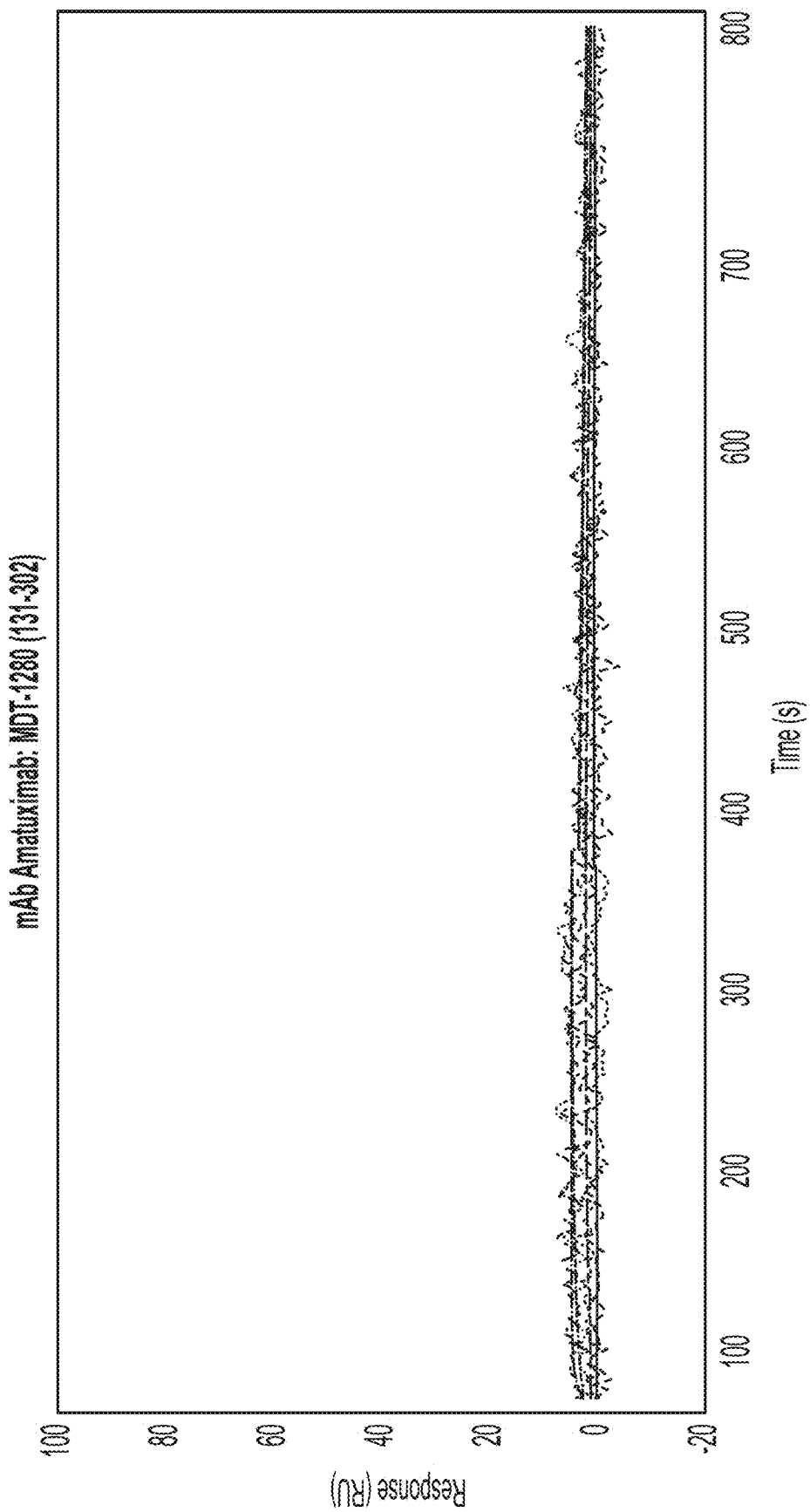
Figure 18C:
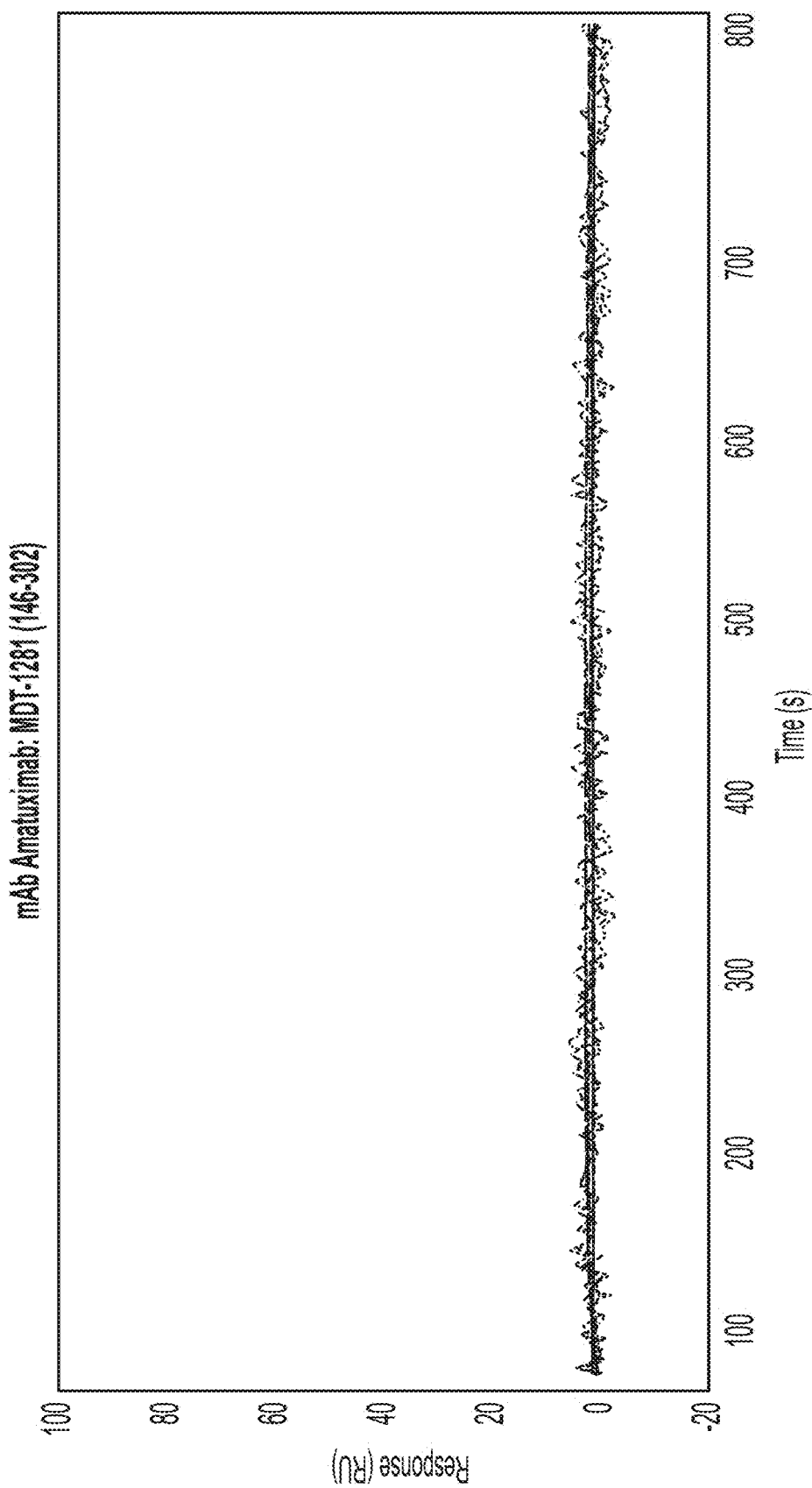
Figure 18D:
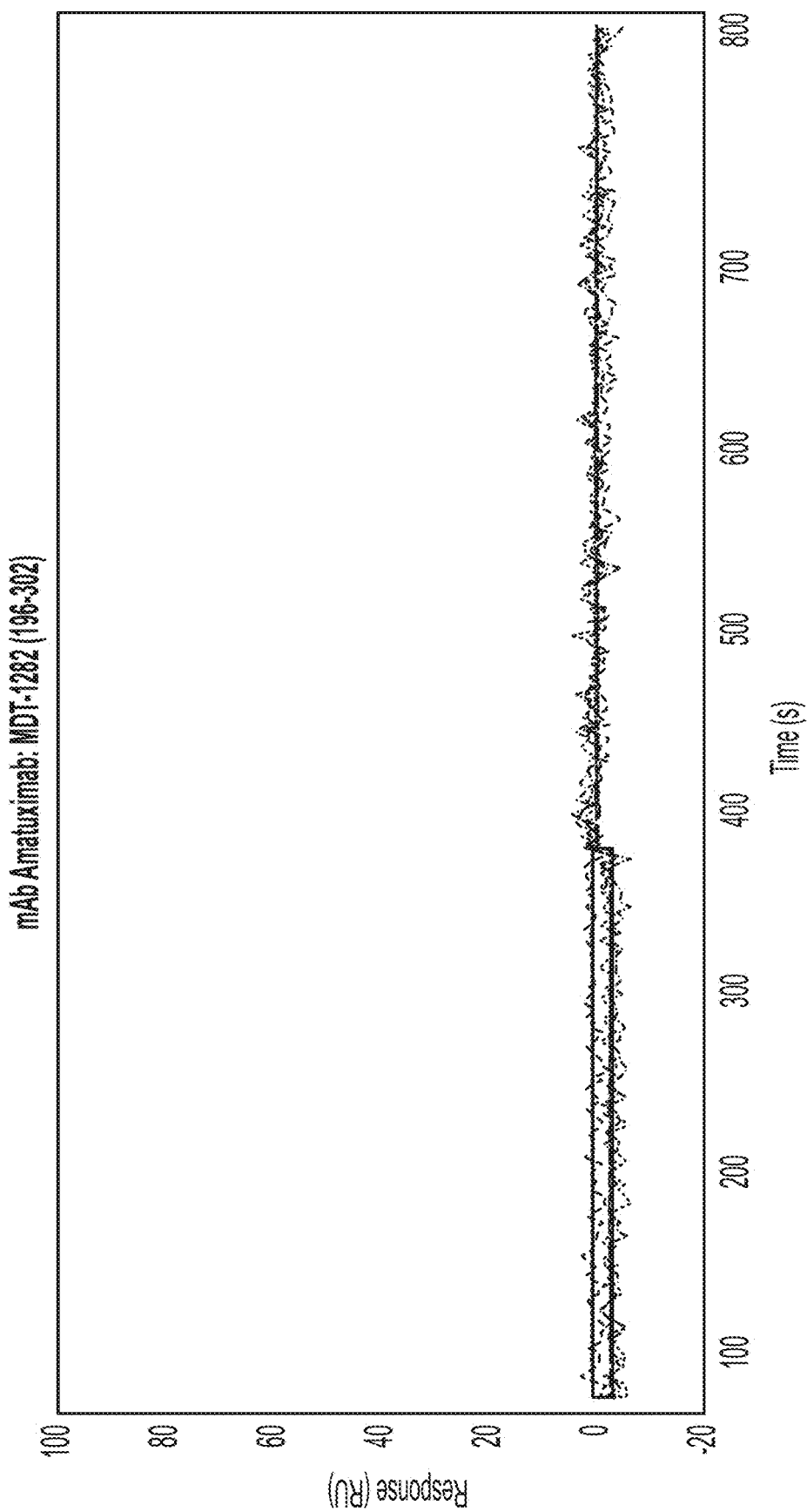

Epitope mapping and cross-reactivity studies were conducted by expressing and purifying discrete subdomains of the MSLN ectodomain, spanning residues 1-302 (SMT-471), 131-302 (MDT-1280), 146-302 (MDT-1281), 196-302 (MDT-1282), 131-187 (not shown but binding has been confirmed), as well as mouse, human and cynomolgus monkey isoforms of the MSLN protein, in human 293-F cells (ThermoFisher: R79007), as described previously (refer to Example 3). For epitope mapping studies, binding of the individual subdomains to antibodies (e.g., 1A12, amatuximab, M912, anetumab, HPN536, etc.) was assessed using SPR methods described previously (refer to Example 3). Representative examples of the binding data are shown at FIGS. 18A-20D. Specifically, shown are binding results of three antibodies, amatuximab (FIGS. 18A-18D), M912 (FIGS. 19A-19D), and IgG-scFv 1A12 (FIGS. 20A-20D), with respect to each of subdomains SMT-471 (FIGS. 18A, 19A, and 20A), MDT-1280 (FIGS. 18B, 19B, and 20B), MDT-1281 (FIGS. 18C, 19C, and 20C), and MDT-1282 (FIGS. 18D, 19D, and 20D). For reference, all of the data depicted at FIGS. 18A-20D are presented together at FIG. 21. At FIG. 21, the labels "EV", "DK", "LC", "EY", and "L" refer to the amino acids at the N and C terminal ends of the particular subdomains (for clarity because the residue labeling used to describe each subdomain is somewhat arbitrary relative to the UNIPROT annotation).

Binding was also assessed using pull-down studies where the scFv:ectodomain pairs were co-expressed in the same cell, and then purified using immobilized metal affinity chromatography. Briefly, the various MSLN isoforms and homologs were expressed as His-tagged proteins with the 1A12 scFv lacking an affinity tag. The MSNL proteins were then pulled down using NiNTA beads. Successful complexation was confirmed using a combination of size exclusion chromatography (SEC) (i.e. supershift assay) as shown at FIG. 22, and SDS-PAGE under non-reducing conditions (not shown). Specifically, the top panel of FIG. 22 shows chromatographs of MSLN alone, and the middle and bottom panels depict chromatographs of MSLN+1A12 scFv complexed with a MSLN cynomolgus monkey isoform and an MSLN human isoform 2, and MSLN+1A12 scFv complexed with MSLN human isoforms 1 and 3, respectively. The 1A12 scFV also was observed to complex with mouse isoforms of MSLN (data not shown).

Example 9: FACS Based Cytotoxicity Assays to Assess Susceptibility of T Cell-Mediated Killing of MSLN-Expressing Cells in the Presence of Anti-MSLN×Anti-CD3 Bispecific Molecules to Soluble MSLN In this Example, mesothelin-expressing ovarian cancer cell lines SKOV3 and OVCAR3 were used in cytotoxicity assays using an automated platform programmed to simultaneously conduct unbiased 96 well assays in which 22,500 T cells were mixed with 4500 Luc-iRFP cancer cells (5:1 E:T ratio) in the presence or absence of bispecific candidate molecules. The T cells were obtained from healthy donors, qualified by flow cytometry for CD3, CD28, CD4, CD8 pre- and post-Easysep no-touch purification. 8 concentrations were tested at 48/72 hour flow cytometry based readouts.

Antibodies like amatuximab, which bind to membrane distal epitopes with high affinity, are also expected to bind to soluble mesothelin-related proteins (SMRPs) with high affinity (FIG. 23). FIGS. 24A and 24B depict cytotoxicity assays comparing the cytotoxic potency of the IgG-scFv molecule having the structure of FIG. 3A (pMSLN:CD3) and anti-MSLN antigen-binding domains derived from the 1A12 anti-MSLN antibody and humanized OKT3 antigen-binding domains in the scFv portion of the molecule, relative to the same molecule comprising anti-MSLN antigen-binding domains derived from amatuximab (dMSLN:CD3). The MSLN-expressing cells in FIG. 24A were OVCAR3 cells, and the MSLN-expressing cells in FIG. 24B were SKOV3 cells. As illustrated, the IgG-scFv molecule with binding domain derived from the 1A12 antibody is much more potent relative to the amatuximab version of the molecule even though amatuximab has higher affinity for MSLN.

Tri-specific T cell activating constructs (TriTACs) such as HPN536, which can bind to MSLN and CD3, have high affinity for soluble MSLN-related proteins and high affinity for cell surface MSLN, as illustratively depicted at FIG. 25A. This can result in therapies that are susceptible to soluble MSLN, as soluble MSLN is a hallmark of MSLN-expressing cancers. To assess the effect of soluble mesothelin on the potency of TriTACs (e.g., HPN536), cytotoxicity assays as described above were conducted in the presence and absence of 30 nM soluble MSLN (FIG. 25B). As illustrated, potency of TriTAC in terms of T-cell mediated killing of MSLN-expressing cells was found to be significantly reduced in the presence of soluble MSLN, as compared to the absence of soluble MSLN.

Hence, therapies susceptible to soluble MSLN, such as the use of TriTac MSLN:CD3 molecules, may exhibit reduced effectiveness as compared to a therapy that not susceptible, or is less susceptible, to soluble MSLN. Turning to FIGS. 26A-26B, depicted is the IgG-scFv molecule having the structure of FIG. 3A (pMSLN:CD3) interacting with cell surface MSLN (FIG. 26A) as compared to soluble MSLN (FIG. 26B). FIG. 26A illustratively depicts that pMSLN:CD3 has high avidity for cell surface MSLN, and FIG. 26B illustratively depicts that pMSLN:CD3 has a low affinity for soluble MSLN-related proteins. To assess the effect of soluble mesothelin on the potency of pMSLN:CD3, cytotoxicity assays as described above were conducted in the presence and absence of 30 nM soluble MSLN (FIG. 26C). As shown, potency of pMSLN:CD3 in terms of T-cell mediated killing of MSLN-expressing cells is reduced to a much lesser extent than the reduction seen for TriTac HPN536 (refer to FIG. 25B) in the presence of 30 nM soluble MSLN. Thus, therapeutic effectiveness to MSLN-expressing cancers may be improved by the use of therapeutic molecules that are less susceptible to soluble MSLN, such as pMSLN:CD3.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. An antigen-binding molecule comprising an antigen-binding domain that specifically binds human mesothelin (MSLN), wherein the antigen-binding domain comprises three heavy chain complementarity determining regions (HCDRs) contained within a heavy chain variable region (HCVR), and three light chain complementarity determining regions (LCDRs) contained within a light chain variable region (LCVR), wherein the HCVR and the LCVR are selected from a HCVR/LCVR amino acid sequence pair selected from the group consisting of: SEQ ID NOs: 1/2, 9/10, 17/18, 25/26, 33/34, and 41/42.

2. The antigen-binding molecule of claim 1, wherein the three HCDRs, HCDR1, HCDR2, and HCDR3, and the three LCDRs, LCDR1, LCDR2, and LCDR3, comprise the amino acid sequences, respectively, of SEQ ID NOs: 3, 4, 5, 6, 7, and 8; 11, 12, 13, 14, 15, and 16; 19, 20, 21, 22, 23, and 24; 27, 28, 29, 30, 31, and 32; 35, 36, 37, 38, 39, and 40; or 43, 44, 45, 46, 47, and 48.

3. The antigen-binding molecule of claim 1, wherein:
the amino acid sequence of the HCVR has at least 90% sequence identity to an amino acid sequence selected from the group consisting of SEQ ID NOs: 1, 9, 17, 25, 33, and 41; and/or
the amino acid sequence of the LCVR has at least 90% sequence identity to an amino acid sequence selected from the group consisting of SEQ ID NOs: 2, 10, 18, 26, 34, and 42.

4. The antigen-binding molecule of claim 1, wherein the antigen-binding molecule is a monoclonal antibody or antigen-binding fragment thereof.

5. The antigen-binding molecule of claim 1, wherein the antigen-binding molecule is a bispecific antibody or antigen-binding fragment thereof comprising a second antigen-binding domain, optionally wherein:
the bispecific antigen-binding molecule comprises two Fab domains covalently attached, respectively, to two immunoglobulin Fc domains, and two scFv domains covalently attached, respectively, to the two Fab domains, optionally wherein:
the two Fab domains each comprise an antigen-binding domain that specifically binds human MSLN, and the two scFv domains each comprise a second antigen-binding domain;
the scFv domains are covalently attached, respectively, via a linker between the heavy chain portion of each of the two scFv domains and the C-terminus of the light chain portion of each of the two Fab domains;
the immunoglobulin Fc domains have reduced binding to Fcγ receptors relative to a wild-type Fc domain of the same isotype; and/or
the immunoglobulin Fc domains are human immunoglobulin Fc domains of isotype IgG1, IgG2, IgG3 or IgG4; or
the bispecific antigen-binding molecule comprises two scFv domains, and the two scFv domains are covalently attached to two immunoglobulin Fc domains, optionally wherein:
the immunoglobulin Fc domains have reduced binding to Fcγ receptors relative to a wild-type Fc domain of the same isotype; and/or
the immunoglobulin Fc domains are human immunoglobulin Fc domains of isotype IgG1, IgG2, IgG3 or IgG4.

6. The antigen-binding molecule of claim 5, wherein the second antigen-binding domain specifically binds a T cell antigen, optionally wherein the T cell antigen is selected from CD3, CD27, CD28, 4-1BB, OX40, and CD2.

7. A pharmaceutical composition comprising the antigen-binding molecule of claim 1, and a pharmaceutically acceptable carrier or diluent.

8. An isolated polynucleotide molecule comprising:
a polynucleotide sequence that encodes a HCVR of an antigen-binding molecule according to claim 1; and/or
a polynucleotide sequence that encodes a LCVR of an antigen-binding molecule according to claim 1,
optionally wherein the polynucleotide molecule is comprised within an expression vector.

9. A host cell comprising the polynucleotide molecule or the expression vector of claim 8.

10. A host cell comprising:
a first polynucleotide encoding a HCVR of an antigen-binding molecule according to claim 1; and
a second polynucleotide encoding an LCVR of an antigen-binding molecule according to claim 1,
optionally wherein the first polynucleotide and the second polynucleotide are comprised within separate expression vectors.

11. A method of producing an antigen-binding molecule that specifically binds human mesothelin (MSLN), the method comprising culturing the host cell of claim 9 under suitable conditions so that the polynucleotide is expressed, and the antigen-binding molecule is produced.

12. A method of producing an antigen-binding molecule that specifically binds human mesothelin (MSLN), the method comprising culturing the host cell of claim 10 under suitable conditions so that the first polynucleotide and the second polynucleotide are expressed, and the antigen-binding molecule is produced.

\* \* \* \* \*